United States Patent
McCormack et al.

(10) Patent No.: US 8,961,754 B2
(45) Date of Patent: Feb. 24, 2015

(54) ELECTROCHEMICAL SENSORS

(71) Applicants: Sean P. McCormack, Summertown (GB); Richard G. Compton, Summertown (GB); Gregory George Wildgoose, Norwich (GB); Nathan Scott Lawrence, Huntingdon (GB)

(72) Inventors: Sean P. McCormack, Summertown (GB); Richard G. Compton, Summertown (GB); Gregory George Wildgoose, Norwich (GB); Nathan Scott Lawrence, Huntingdon (GB)

(73) Assignee: Isis Innovation Ltd (GB)

( * ) Notice: Subject to any disclaimer, the term of this patent is extended or adjusted under 35 U.S.C. 154(b) by 0 days.

(21) Appl. No.: 14/033,871

(22) Filed: Sep. 23, 2013

(65) Prior Publication Data
US 2014/0083853 A1    Mar. 27, 2014

Related U.S. Application Data

(63) Continuation of application No. 13/183,632, filed on Jul. 15, 2011, now Pat. No. 8,562,797, which is a continuation of application No. 10/591,491, filed as application No. PCT/GB2005/000802 on Mar. 4, 2005, now abandoned.

(30) Foreign Application Priority Data

| Mar. 4, 2004 | (GB) | 0404903.7 |
| Mar. 4, 2004 | (GB) | 0404904.5 |
| Oct. 12, 2004 | (GB) | 0422620.5 |

(51) Int. Cl.
| *C25B 11/12* | (2006.01) |
| *G01N 27/30* | (2006.01) |
| *B82Y 15/00* | (2011.01) |
| *B82Y 30/00* | (2011.01) |
| *B82Y 40/00* | (2011.01) |
| *C01B 31/02* | (2006.01) |
| *C01B 31/04* | (2006.01) |

(52) U.S. Cl.
CPC .............. *G01N 27/302* (2013.01); *B82Y 15/00* (2013.01); *B82Y 30/00* (2013.01); *B82Y 40/00* (2013.01); *C01B 31/0273* (2013.01); *C01B 31/04* (2013.01); *G01N 27/308* (2013.01)
USPC ......................................... 204/294; 204/433

(58) Field of Classification Search
USPC ......................................... 204/294, 416, 433
See application file for complete search history.

(56) References Cited

U.S. PATENT DOCUMENTS 5,223,117 A * 6/1993 Wrighton et al. ............. 204/415

* cited by examiner

*Primary Examiner* — J. Christopher Ball
(74) *Attorney, Agent, or Firm* — Renner Kenner Greive Bobak Taylor & Weber

(57) ABSTRACT

An electrode for use in a electrochemical sensor comprises carbon modified with a chemically sensitive redox-active compound, excluding an electrode based on carbon having derivatized thereron two redox-active species wherein at least one of said species is selected from anthraquinone, phenanthrenequinone and N,N'-diphenyl-p-phenylenediamine (DPPD). The invention further provides a pH sensor comprising:
  a working electrode comprising carbon modified with a chemically sensitive redox active material; and
  a counter electrode,
wherein the ratio of the surface area of the working electrode to the surface area of the counter electrode is from 1:10 to 10:1. Also provided is a pH sensor comprising:
  a working electrode comprising carbon modified with a chemically sensitive redox active material, and
  a counter electrode,
wherein the area of the working electrode is from 500 μm$^2$ to 0.1 m$^2$. The uses of these electrodes and sensors are also described.

20 Claims, 61 Drawing Sheets

ELECTROCHEMICAL SENSORS

CROSS-REFERENCE TO RELATED APPLICATIONS

This application is a continuation of U.S. patent application Ser. No. 13/183,632, filed Jul. 15, 2013, which is a continuation of U.S. patent application Ser. No. 10/591,491, filed Sep. 1, 2006, abandoned, which is a national stage application under 35 USC 371 of PCT Application No. PCT/GB2005/000802, filed, Mar. 4, 2005, expired, the disclosures of both of which are incorporated herein by reference.

FIELD OF THE INVENTION

The invention relates to electrochemical sensors for use in various environments, including non-downhole environments. For example, the sensors may be used for the determination of pH of substances in "dirty" environments, such as effluent and other waste streams the invention also relates to various materials, which may be used, for instance, in electrodes forming part of electrochemical sensors.

BACKGROUND OF THE INVENTION

U.S. Pat. No. 5,223,117 relates to self-assembly microelectrodes used in electrochemical sensors. The microelectrodes (which are the working electrode in the sensors) are modified with monolayer coverages of reference and indicator molecules, with both chemically sensitive redox materials and chemically insensitive redox materials being present on the same electrode. It is necessary for the microelectrodes to be significantly smaller than the counterelectrodes, for example the counter electrode area must be at least $10^2$ to $10^3$ times the working electrode area. An advantage of such a small working electrode with an internal reference is that the sensor is minimally invasive, and can therefore be used in biomedical sensing.

UK Patent Application No. 2 391 314 describes electrochemical sensors for measuring the amount of hydrogen sulphide or thiols in a fluid. The sensor comprises a precursor and reaction solution which, together with the hydrogen sulphide or thiols, create a redox reaction. The current produced by this redox reaction is dependent upon the concentration of hydrogen sulphide or thiols. The sensors described in this document are for use in downhole applications, i.e. to extend down boreholes during a drilling operation. Given the size restrictions on apparatus which must extend into a borehole, the sensors must be relatively small.

Carbon-based electrode materials have been in use for many decades. The main forms of carbon in common use are glassy carbon, carbon fibres, carbon black, graphite, carbon paste and carbon epoxy electrode. Carbon is an attractive electrode material as it is relatively chemically inert yet it has a high surface activity and a wide operational potential window (ca. −1.0 V to +1.0 V vs. the saturated calomel electrode in aqueous solution).

However, there remains a need for more robust, reagentless sensors that can provide accurate results in hostile environments or "dirty" media such as effluents or sewage. Furthermore, there is a requirement for sensors to be used under various conditions, such as at temperatures above room temperature. There is renewed interest in developing sensors capable of measuring pH accurately at elevated temperatures. The present invention aims to address these issues.

SUMMARY OF THE INVENTION

According to the present invention, there is provided an electrode for use in a electrochemical sensor, said electrode comprising carbon modified with a chemically sensitive redox active compound which is not anthraquinone, phenanthrenequinone or N,N'-diphenyl-p-phenylenediamine (DPPD).

The present invention also provides a pH sensor comprising:
a working electrode comprising a chemically sensitive redox material; and
a counter electrode,
wherein the ratio of the surface area of the working electrode to the surface area of the counter electrode is from 1:10 to 10:1.

The invention further provides a pH sensor comprising:
a working electrode comprising a chemically sensitive redox material, and
a counter electrode,
wherein the area of the working electrode is from 500 $\mu m^2$ to 0.1 $m^2$.

These pH sensors have an advantage over those in the prior art in that they are less likely to be fouled or clogged by dirt in the fluid being measured, and accordingly they have a longer lifetime before they need to be replaced.

The electrodes of the present invention may be used in an electrochemical sensor, and in particular in a pH sensor. The electrodes of the invention and the pH sensors of the invention are preferably suitable for use in a non-downhole environment.

The invention also provides a method for preparing an electrode for use in an electrochemical sensor, said method comprising modifying carbon with a chemically sensitive redox active material with the proviso that the chemically sensitive redox active material is not anthraquinone, phenanthrenequinone or N,N☐-diphenyl-p-phenylenediamine (DPPD).

Finally, the invention further provides a method for preparing an electrode in situ comprising applying carbon modified with a chemically sensitive redox active material to the surface of a substrate, wherein the chemically sensitive redox active material undergoes an irreversible chemical reaction when subjected to cyclic voltammetry.

DETAILED DESCRIPTION OF THE FIRST PREFERRED ASPECT OF THE INVENTION

Figure 1A:
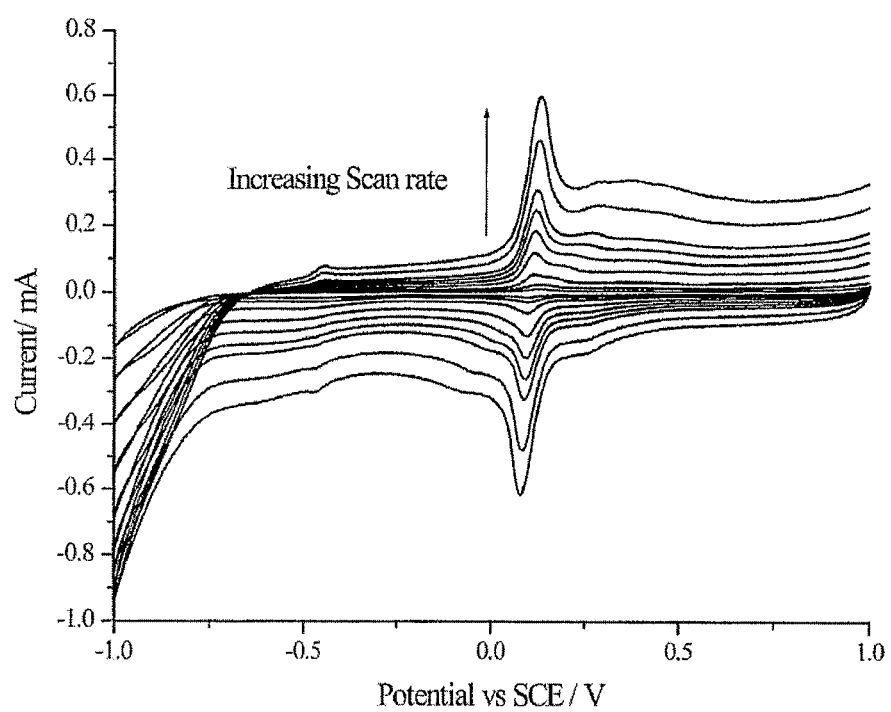
FIG. 1A is the voltammetric response of 6-nitro chrysene carbon immobilised on bppg after the development of the reversible system at pH 1.0 (0.1M HCl+0.1M KCl) varying the scan rate (25, 50, 100, 200, 300, 400, 500, 750, 1000 mV $s^{-1}$)

The pH sensors and electrodes of the first preferred aspect of the present invention are preferably used in a non-downhole environment. The term "non-downhole" means that the sensors are used in environments other than those down boreholes or other subterranean volumes of liquid. Suitable non-downhole applications include pH measurement in environmental, chemical, waste water, industrial and effluent applications. The term "environmental" includes testing such as in rivers and seas. The term "chemical" includes testing during chemical processes in laboratories or factories. The term "industrial" includes waste from industrial processes. The term "effluent" includes discharges of liquid waste, for example sewage. Effluent may be mostly or entirely non-aqueous. Waste water includes liquid waste from domestic and commercial properties. Waste water is predominantly aqueous.

In the following description the term "chemically irreversible behaviour" means that the compounds concerned react via an irreversible chemical reaction to form another species. The compound and the species into which it converts will have different electrochemical profiles. The term "chemically reversible behaviour" means that the compounds undergo reversible reactions when used in the sensors of the invention, and accordingly do not convert into other species which cannot convert back into the original compound.

The term "reversible electrochemistry" is used interchangeably with the phrase "electrochemically reversible behaviour". This means that the compound can gain and lose electrons repeatedly without its electrochemical profile varying over time.

The individual components and aspects of the invention will now be described in more detail.

Carbon

The carbon used in the present invention must be capable of being modified by the chemically sensitive redox active material. Preferably it is in the form of carbon powder. It is particularly preferred that the carbon is in the form of graphite particles having a mean diameter of from 0.1 to 50 μm, preferably from 1 to 30 μm. Alternatively the carbon can be present in the form of carbon nanotubes. These are in effect "rolled up" sheets of graphite. Conventionally they are either single-walled carbon nanotubes or multi-walled carbon nanotubes (MWCNTs).

Chemically Sensitive Redox Active Material

The chemically sensitive redox active material may be any organic material capable of undergoing electron loss and gain. Preferably it is a solid phase material. When immobilised onto a substrate, e.g. glassy carbon or a basal plane pyrolytic graphite (bppg) electrode, it undergoes concomitant proton and electron loss/gain on oxidation/reduction.

This material is described as being "chemically sensitive" because it must show an electrochemical response which is dependent upon the species which is to be detected or measured. For example, in order to be of use in a pH sensor, the chemically sensitive redox active material must have an electrochemical response which is sensitive to a change in hydrogen ion concentration.

This material need not comprise only one compound, but can instead comprise a mixture of different chemically sensitive redox active compounds.

Preferred chemically sensitive redox active materials are those which comprise a) compounds exhibiting chemically and electrochemically reversible behaviour, and b) compounds exhibiting chemically irreversible behaviour leading to electrochemically reversible behaviour. Of the latter category, preferred materials comprise b.1) compounds which form polymers, and b.2) compounds which contain a nitro group. Considering each of these groups in turn:

a) Redox Active Materials Comprising Compounds Exhibiting Chemically and Electrochemically Reversible Behaviour The compounds in these redox active materials produce stable reversible voltammetric peaks when they are subjected to both cyclic voltammetry and square-wave voltammetry. They exhibit Nernstian behaviour. When the sensor in which they are incorporated is intended to measure pH, the plot of peak potential against pH for each compound produces a linear, Nernstian response according to the following equation:

$$E_{peak} = E^0_{formal} - \frac{2.3\,RTm}{nF}pH$$

wherein $E_{peak}$ is the peak potential/V, $E^0_{formal}$/V is the formal potential, R is the universal gas constant/J K$^{-1}$ mol$^{-1}$, T is the temperature/K, F is the Faraday constant/C mol$^{-1}$, and n and m are the number of electrons and protons transferred respectively. In the examples which follow, n and m are both likely to be equal to two as proposed in scheme 1. By monitoring the peak potential of these compounds, the pH can be determined.

SCHEME 1
The proposed redox pathway for DPA, PAQ and anthracene

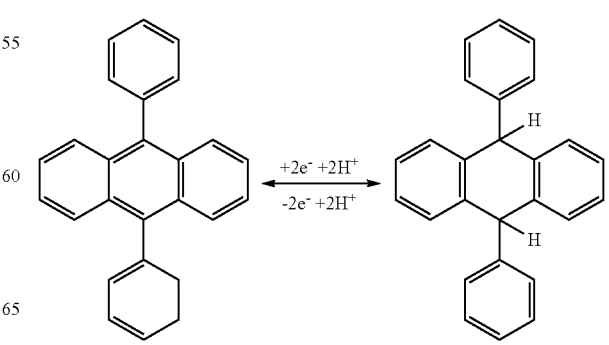

-continued

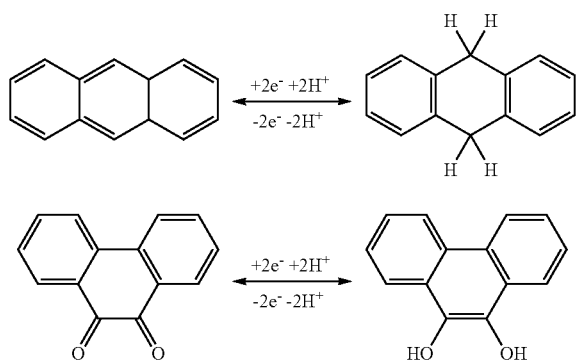

Suitable compounds which exhibit chemically and electrochemically reversible behaviour include quinones and anthracenes. Compounds which will be effective in pH sensors are capable of undergoing a redox reaction that is reversible and involves the uptake and release of protons. The skilled person will be able to determine other compounds which will be suitable in this embodiment of the invention.

b) Redox Active Materials Comprising Compounds Exhibiting Chemically Irreversible Behaviour Leading to Electrochemically Reversible Behaviour The compounds in these redox active materials, when subjected to cyclic voltammetry, undergo an irreversible chemical reaction. The substance formed after as a result of this irreversible chemical reaction (e.g. a different compound or a polymer of the reactant compound) exhibits electrochemically reversible behaviour similar to the compounds described in paragraph a) above. The peak potential of these substances shows a Nernstian response to the species to be measured (the target analyte) and these substances can therefore be used in electrochemical sensors such as pH sensors.

The compounds in this group can be split into a number of subsets, including:

b. 1) Those which Form Polymers

The compounds useful in this aspect of the invention all form polymers via an irreversible chemical reaction. The resulting polymers have peak potentials which exhibit a linear, Nernstian response to the species to be measured when subjected to cyclic voltammetry. Suitable compounds for use in this aspect of the invention include diphenylamine and phenothiazine dyes, with diphenylamine being most preferred. Suitable phenothiazine dyes include toluidine blue, methylene blue and thionin. Of these, methylene blue and thionin are preferred.

In the prior art, the majority of existing amperometric pH sensors are based on the pH-switchable permselectivity of thin films and membranes. One such family of conducting polymeric films is based on polyaniline-like structures formed by electro-oxidative methods. The polymerisation of diphenylamine has been carried out electrochemically in non-aqueous solvents rather than in solution via chemical means due to the poor solubility of polydiphenylamine in most solvents. Much of the discussion in the prior art has focused on the coupling mechanism for the formation of these polymers from diphenylamine in non-aqueous solvents on the surface of gold or platinum electrodes.

However, the present invention differs from the prior art in that the compounds can be used to modify carbon. For example, they can be physisorbed onto the surface of carbon particles. When this occurs, the compounds undergo an oxidative electropolymerisation reaction whilst in contact with aqueous solutions to form polymers, which are themselves sensitive to changes in local pH. To apply this to a particular compound, when diphenylamine is used to modify carbon, the compound can then undergo oxidative electropolymerisation whilst in contact with aqueous solutions to form polydiphenylamine, which is itself useful in sensing changes in local pH.

In general, the behaviour of compounds according to this aspect of the invention is as follows. When subjected to cyclic voltammetry, an initial peak is observed, corresponding to the redox active material in its original form. Gradually this peak disappears as eventually all of the redox active material on the surface of the carbon is polymerised. A new reversible system is then generated, corresponding to the polymeric form of the redox active material. The peak corresponding to this system grows upon repetitive cycling and eventually stabilises.

By monitoring the peak potentials of both the irreversible peak and the reversible peak, the pH can be monitored. Analysis of the gradient of a plot of peak potential vs. pH for both the irreversible system and the reversible system shows a shift in a linear Nernstian fashion.

Thus, these redox active materials not only provide a robust reagentless pH sensor over a wide range, but also provide a technique for preparing an electrode in situ.

b.2) Those which Contain a Nitro Group

Such redox active materials are usually aromatic compounds containing one or more carbocyclic rings and/or heterocyclic rings and are substituted by at least one nitro group. Suitable carbocyclic compounds include phenyl, anthracene, fluoranthene and the like. Suitable heterocyclic compounds include the carbocyclic compounds having one or more carbon atoms in the ring replaced by one or more heteroatoms. The heteroatoms are preferably selected from nitrogen, oxygen and sulphur. Preferably the heterocyclic compounds contain, in the ring, from one to five heteroatoms, preferably from one to three heteroatoms. The compounds should preferably not undergo any other competing chemical transformations or reactions which mask their response to the species which is to be measured by the electrochemical sensors of the invention.

Preferred compounds include nitroanthracene, in particular where the anthracene molecule is substituted by the nitro group in the 9 position; nitrochrysene, in particular where the nitro group is in the 6 position; and nitrofluoranthene, in particular where the nitro group is in the 3 position. Other compounds which can be used include fast black K (FBK).

The electrochemical reductions of aromatic compounds follow complex mechanistic pathways in both aqueous and non-aqueous media, and at the three-phase boundary between microdroplets of oils containing nitro groups, aqueous electrolyte and an electrode. There has been speculation about the exact mechanism of the reduction of nitro groups, with various different pathways being suggested depending on the pH of the solution. However, it is now generally agreed that the pathway shown below in Scheme 2 below is that followed.

This scheme uses nitrobenzene as an example of such a compound, but the general scheme is the same for the other nitro-containing compounds.

SCHEME 2
The general mechanism for the electrochemical reduction of an aryl nitro moiety illustrated here by nitrobenzene

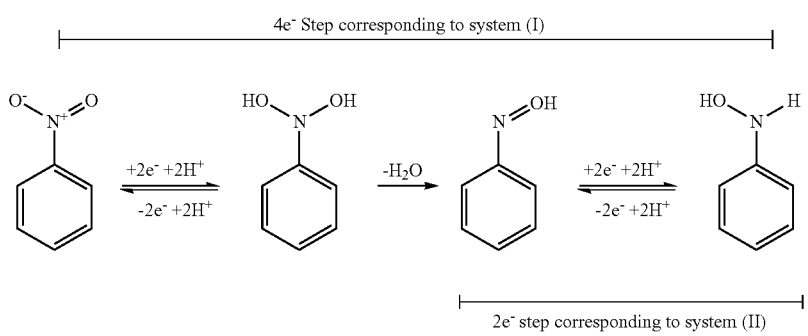

In this mechanism the nitro group undergoes a six-electron, six-proton reduction to form the corresponding aryl amine which is split into two steps: a four-electron, four-proton reduction to the aryl hydroxylamine via the nitroso intermediate, and a further two-electron, two-proton reduction to the aryl amine.

As with the compounds which form polymers, these redox active materials not only provide a robust reagentless pH sensor over a wide range, but also provide a technique for preparing an electrode in situ.

Chemically Insensitive Redox Active Materials

In addition to the chemically sensitive redox active material, the invention may also employ chemically insensitive redox active materials. Thus, a chemically insensitive redox active material may be present on the same substrate as the chemically sensitive redox active material.

A chemically insensitive redox active material may also be present on a separate electrode used in an electrochemical sensor according to the invention.

The chemically insensitive materials may be used to modify carbon, as with the chemically sensitive materials. Alternatively, these materials can be applied directly to the substrate (to bppg, for example). If the material is to be screen printed, then a binder and thinner would also be required.

The chemically insensitive redox active materials are, like the chemically sensitive redox active materials, capable of undergoing repeated electron loss and gain. However, the electrochemical response of these compounds is not dependent on the concentration of the species to be measured by the sensor. For example, if the sensor is a pH sensor, then the electrochemical response of the chemically insensitive redox active material will be insensitive to a change in concentration of hydrogen ions, and will therefore be insensitive to a change in pH.

The choice of the chemically insensitive redox compounds will clearly also depend upon the species which the electrochemical sensor is to detect. In the case of pH sensors, suitable compounds include insoluble ferricyanide or ferrocyanide salts, octacyanomolybdate (IV) salts, or polymers such as polyvinylferrocene. These compounds act as reference materials, which generate their own, reference signals when subjected to cyclic voltammetry. The difference in potential between the peaks of the chemically sensitive redox compounds and the chemically insensitive redox compounds can be used to improve the accuracy of the sensor, as discussed in U.S. Pat. No. 5,223,117.

Substrate

The substrate onto which is applied the modified carbon may be any substrate conventionally used in the manufacture of electrodes. For example, the substrate may be a basal plane pyrolytic graphite (bppg) electrode or glassy carbon, metal electrodes such as gold or platinum, or optically transparent electrodes such as those comprising ITO. The substrate preferably has good electrical contact with the modified carbon, and also has a surface such that good coverage with the modified carbon can be achieved.

The modified carbon may be applied by any known procedure. In particular, screen-printing is a suitable conventional technique.

Working Electrode

The size of the working electrodes of the present invention sensor is such that the surface area is preferably from 10 μm² to 0.1 m², more preferably from 50 μm² to 0.1 m², and more preferably from 500 μm² to 0.1 m²

Another relevant parameter when considering the electrodes of the present invention is the ratio of the surface area of the working electrode to the surface area of the counter electrode. This is preferably from 1:10 to 10:1, more preferably from 1:5 to 3:1.

In contrast to the electrodes of the present invention, those disclosed in the prior art tend to have a much smaller surface area of the working electrode and/or have a counter electrode which is substantially larger in size than the working electrode.

The electrodes of the present invention have the advantage that they are less likely to be fouled by the substances they are being used to analyse. The working life of the sensors is therefore lengthened before the electrode needs to be replaced.

Furthermore, the electrodes of the invention can be made cheaply and can be readily disposed of. While being larger than those discussed in the prior art, they are still small enough to be easily carried and can thus be used in portable electrochemical sensors.

The working electrodes of the present invention may comprise one or more areas of redox active material on the same substrate. These areas are preferably separated from each other, and may thus appear as "spots" on the surface of the substrate. At least one area will comprise carbon modified with a chemically sensitive redox active material. The other area or areas may comprise chemically sensitive redox active materials or chemically insensitive redox active materials.

According to one embodiment, the working electrode comprises two separate areas, one of which comprises carbon modified with a chemically sensitive redox active material, the other of which comprises a chemically insensitive redox active material. According to another embodiment, the working electrode comprises four separate areas, two of which comprise chemically sensitive redox active materials, the other two of which comprise chemically insensitive redox active materials. One advantage of having a number of separate areas of material is that a number of electrodes can be present on one sensor, or a number of different materials can be deposited on different areas of one working electrode. The result of this is that the accuracy and sensitivity of the sensor can be increased pH Sensor The structure of the sensor will depend upon its final application, and hence depends upon the substance which is to be measured and the environment in which measurement will take place. Known sensor structures may be employed in conjunction with the agglomerates and electrodes described herein.

Exemplary sensors may have a two or three terminal arrangement. Thus, they may comprise a working electrode of the invention and a combined counter and reference electrode, or a working electrode, counter electrode and a reference electrode. The reference electrode and counter electrode can be any conventional electrodes known in the art, such as silver electrodes, calomel electrodes or standard hydrogen electrodes. The reference electrode can also be provided by the chemically insensitive redox active material described earlier.

The materials used in the sensor depend upon which species the sensor is intended to measure and the environment in which the sensor is to be used. In order to modify the sensor to be sensitive to a different species it is simply required for the skilled person to substitute the redox active material with a different redox active material sensitive to the species which is to be measured.

Figure 11:
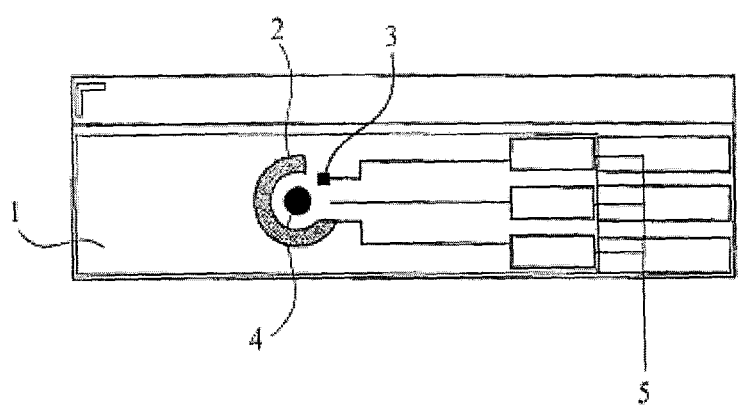
FIG. 11 shows a pH sensor according to the first preferred aspect of the invention.

An exemplary pH sensor according to the invention is shown in FIG. 11. The substrate 1 bears the electrodes 2, 3 and 4. The counter electrode 2 and the reference electrode 3 both comprise silver. In this Figure the working electrode comprises carbon derivatised with N,N'-diphenyl-p-phenylenediamine (DPPD), with the electrode containing 10% by mass of DPPD. The pH sensor is connected to equipment to measure cyclic voltammetry via the three terminals 5.

Figure 12:
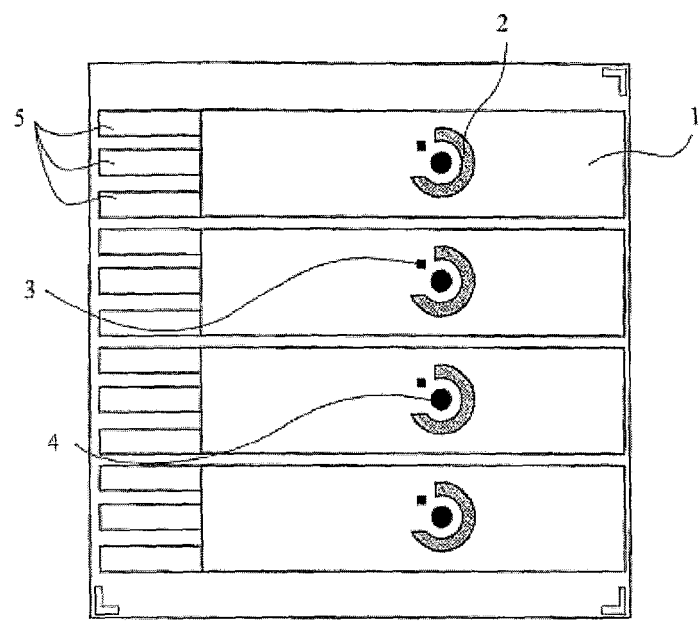
FIG. 12 shows an array of pH sensors according to the first preferred aspect of the invention on a single substrate.
Figure 13:
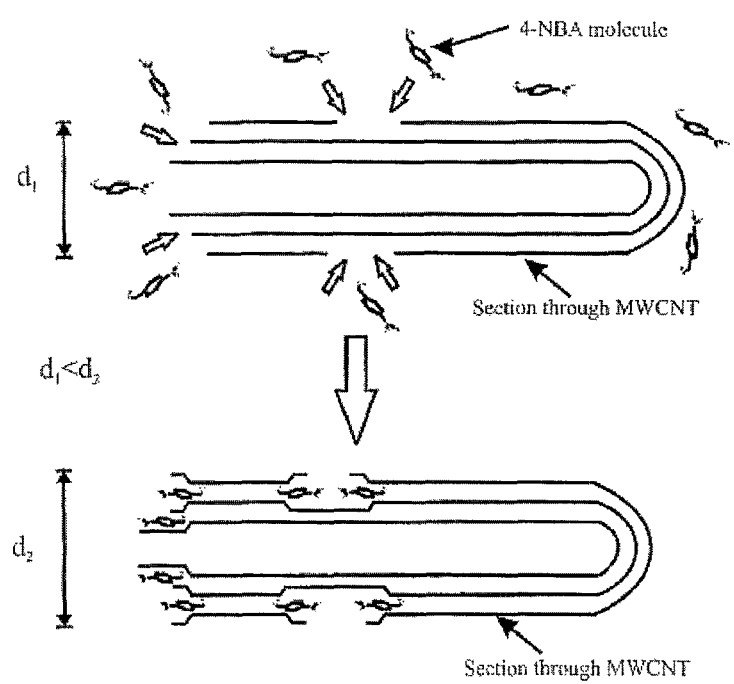
FIG. 13 discloses a schematic diagram illustrating the proposed partial intercalation of 4-NBA into localised edge-plane defect sites along the surface of a MWCNT.

FIG. 12 shows another embodiment of the invention in which four different sensors are present on one base. The sensors are produced by screen printing, and can be cut into individual sensor strips when required. The numerals used in this Figure correspond to those used in FIG. 11 above.

Modification Method

The preferred methods for modifying the carbon used in the present invention are
 a) homogeneous chemical derivatisation with the chemically sensitive redox active material;
 b) derivatisation via physical adsorption of the chemically sensitive redox active material; and
 c) physical mixing with the chemically sensitive active material and a binder.

Homogeneous chemical derivatisation describes a method wherein the carbon and chemically sensitive redox active material are combined in a solvent the presence of a reductant (e.g. hypophosphorous acid) in order to cause chemical bonding of the two species. The term "homogeneous" refers to the fact that all of the reductant (and the reductant only) is in the solution phase. The carbon is dispersed in the solvent while the reductant and the chemically sensitive redox active material (or a precursor thereof) are dissolved in solution. The chemical reaction occurs solely in the solution phase to generate a species which then bonds to the surface of the carbon.

Derivatisation via physical adsorption means that the carbon and chemically sensitive redox active material are combined in such a way as to cause the latter to become physically adsorbed onto the surface of the carbon.

The two processes above differ in that, in the case of physical adsorption, the skilled person relies on relative hydrophobicities to induce derivatisation of the carbon surface. In chemical derivatisation an actual chemical bond is formed between the carbon and the chemically sensitive redox active material.

The physical mixing option simply requires the carbon and chemically sensitive redox active material to be mechanically mixed together in the presence of a binder. This allows the carbon and redox active material to be associated with one another without forming chemical bonds. The choice of binder depends on the conditions to which the electrode will be subjected. Conventional binders and thinners, such as those employed in the screen-printing industry, are possible candidates.

Examples of the First Preferred Aspect of the Invention

Reagents and Equipment

All reagents were obtained from Aldrich (except for methylene blue and thionin which were obtained from British Drug House Chemicals and potassium chloride which was supplied by Riedel de Haën) and were of the highest grade available and used without further purification. All aqueous solutions were prepared using deionised water from an Elgastat (Elga, UK) UHQ grade water system with a resistivity of not less than 18 MΩ cm. All measurements were made after degassing the solution with pure $N_2$ gas (BOC gases, Guildford, Surrey, UK) for 30 minutes and unless stated otherwise results were recorded at a temperature of 22±2° C.

Solutions of known pH in the range pH 1 to 12 were made up in de-ionised water as follows: pH 1, 0.1M HCl; pH 4.6, 0.1M acetic acid+0.1M sodium acetate; pH 6.8, 0.025M $Na_2HPO_4$+0.025M $KH_2PO_4$; pH 9.2, 0.05M disodium tetraborate; pH 12, 0.01M sodium hydroxide. These solutions contained in addition 0.1M KCl as additional supporting electrolyte.

pH measurements were performed on each freshly made solution to ensure it had the correct pH using a Jenway 3030 pH meter.

Electrochemical measurements were recorded using a µAutolab computer controlled potentiostat (Ecochemie, Netherlands) with a standard three-electrode configuration. All room-temperature experiments were carried out in a cell of volume 30 $cm^3$. High-temperature voltammetry (30-70° C.) was undertaken using a double-walled glass cell of volume 25 $cm^3$ thermostatted to the desired temperature through circulation of water from a heated water bath. In all cases a basal plane pyrolytic graphite (bppg, 0.20 $cm^2$, Le Carbone Ltd., Sussex, UK) electrode acted as the working electrode (see below). A platinum rod acted as the counter electrode, and a saturated calomel electrode as the reference electrode (SCE, Radiometer, Copenhagen) completed the cell assembly.

Unless stated otherwise cyclic voltammograms were recorded using the following parameters: step potential 2 mV, scan rate 100 mV s$^{-1}$. Square wave voltammetric parameters were as follows: frequency 12.5 Hz, step potential 2 mV and amplitude 5 mV.

Scanning electron microscopy (SEM) was conducted using a Cambridge stereoscan electron microscope at a magnification of 83×. Initial characterisation of the size of the carbon particles was carried out using scanning electron microscopy (SEM). This involved attaching the carbon particles to a strip of conducting sticky tape, from which the SEM image was taken. Analysis of the image revealed that the carbon particles had a mean diameter of 1.5 µm, consistent with that stated by the manufacturer (Aldrich, graphite powder, 1-2 µm, synthetic).

Example 1

Carbon Powder Derivatisation Methods a) Derivatisation Via Physical Adsorption:

Physical adsorption onto carbon powder was carried out by mixing 2 g of carbon powder with 25 cm$^3$ 0.1M HCl+0.1M KCl and 10 cm$^3$ of a 10 mM solution in acetone of one of the following compounds: anthracene, azobenzene (AB), diphenylamine, 9,10-diphenylanthracene (DPA), 1,3-diphenyl guanidine, fluorescein, methylene blue, 3-nitrofluoranthene (3-NF), 6-nitrochrysene (6-NC), 9-nitroanthracene (9-NA), 9,10-phenanthraquinone (PAQ) or triphenylamine. The reaction mixture was stirred continuously for 2 hours in a beaker and then filtered by water suction after which it was washed with distilled water to remove the acid and salt. It was then air-dried by placing inside a fume hood for 12 hours and finally stored in an airtight container.

b) Homogeneous Chemical Derivatisation

Initially 2 g of carbon powder was mixed with a 10 cm$^3$ solution containing 5 mM Fast Black K (2,5-dimethoxy-4-[(4-nitrophenyl)azo]benzenediazonium chloride; FBK), to which 50 cm$^3$ hypophosphorous acid (H$_3$PO$_2$, 50%; Aldrich) was added. The reaction mixture was then left to stand at 5° C. for 30 minutes with stirring every ten minutes, after which the solution was filtered by water suction in order to remove any unreacted species from the carbon. Further washing with deionised water was carried out to remove any remaining acid and finally with acetonitrile to remove any unreacted diazonium salt from the mixture. The carbon particles were then air-dried by placing inside a fume hood for a period of 12 hours after which they were stored in an airtight container.

Lifetimes of the Derivatised Carbon Powders:

Each compound derivatised using one of the methods given above and stored in an airtight container was studied over a period of several months and was found to produce stable voltammograms after this period of time had elapsed. This shows that there is little or no desorption from the carbon particle surface and that the derivatised carbon powders are stable over time

Example 2

Immobilisation of the Derivatised Carbon onto a Substrate

The newly derivatised carbon powders were characterised by abrasive immobilisation onto the surface of a bppg electrode prior to characterisation. This was done by initially polishing the electrode on glass polishing paper (H00/240) after which they were polished on silicon carbide paper (P1000C) for smoothness. The derivatised carbon was then mechanically immobilised onto the bppg electrode by gently rubbing the electrode surface on a fine filter paper (Whatman) containing the functionalised carbon. It is worth noting that in the case of 3-nitrofluoranthene, 6-nitrochrysene and 9-nitroanthracene derivatised carbon powders, the derivatised carbon was immobilised onto the basal plane at the beginning of each set of experiments as the electro-reduction of the nitro group is chemically irreversible and hence the signal is lost after the first initial scan (see below).

Characterisation Protocol:

In order to verify that each compound studied was attached to the carbon particles, either through physical adsorption or via a covalent bond depending on the derivatisation method, the following protocol was carried out using cyclic voltammetry over the entire pH range studied (pH 1-12) on each newly derivatised carbon immobilised onto a bppg electrode. First ten repetitive scans (not shown) from +1.0 V to −1.0 V were typically conducted to ensure the stability of the species. In each case an electrochemically reversible system could be observed which rapidly stabilised to give a nearly symmetrical wave shape with a separation of ca 20 mV between the oxidative and reductive peaks which is close to the ideal zero peak to peak separation for an immobilised species. Next the electrolyte solution was replaced with fresh solution and the voltammetric response recorded. The corresponding voltammetric response (not shown) was found to overlay the last scan thereby confirming that the electroactive species remains on the electrode surface. Finally the scan rate was varied and a plot of peak current vs. scan rate was found to be linear, consistent with a surface bound species.

Figure 1B:
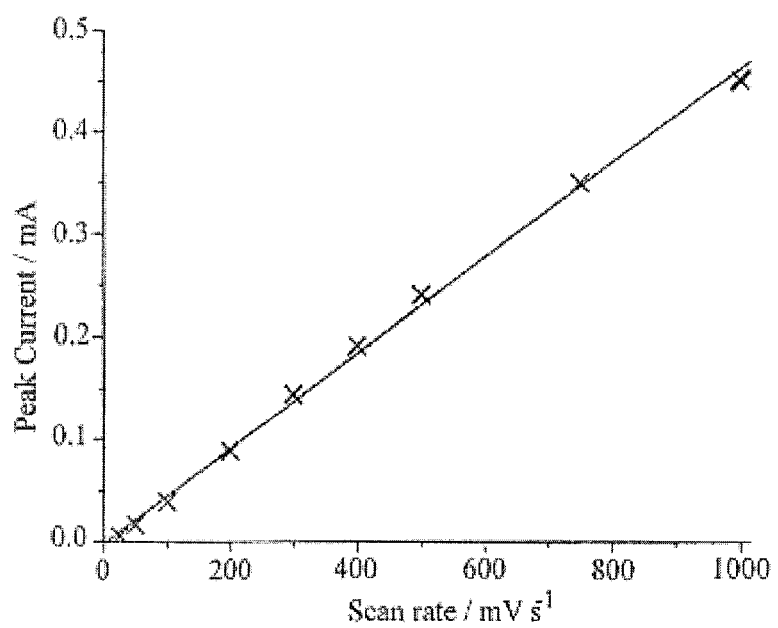
FIG. 1B is the corresponding plot of oxidative peak potential vs. scan rate (insert).

Together these tests each confirm that a particular compound studied is attached to the surface of the carbon particles. By way of an example FIG. 1A shows the voltammetric response of 6-nitrochrysene physically derivatised carbon with varying scan rate (25-1000 mV s$^{-1}$) at pH 1.0 (0.1M HCl+0.1M KCl) after development of the reversible system (see below). FIG. 1B is a plot of the corresponding peak current against scan rate which is linear as expected for a surface bound species.

All of the compounds studied were found to be immobilised and stable between pH 1-12 at room temperature except for thionin and methylene blue which were both found to slowly desorb upon repetitive cycling at pHs greater than 6.8 and 4.6 respectively. Fluorescein, 1,3-diphenyl guanidine and triphenylamine produced very poorly defined voltammetric waves at any pH and as such no further analysis was performed on them.

Example 3

Voltammetric Response of the Derivatised Carbons at 22° C. From pH 1 to 12

The response of the derivatised carbons at each pH was first studied individually using cyclic voltammetry (CV) and then using square wave voltammetry (SWV). SWV was utilised as the electrochemical probe of the system as it has significant advantages to conventional CV, providing well-defined voltammetric peaks in a single sweep due to the reversibility of each redox system studied. The corresponding cyclic voltammograms and square wave voltammograms were recorded in a range of pH solutions (pH 1.0, 0.1M HCl+0.1M KCl; pH 4.6, 0.1M acetic acid+0.1M sodium acetate+0.1M KCl; pH 6.8, 0.025M Na$_2$HPO$_4$+0.025M KH$_2$PO$_4$+0.1M KCl; pH 9.2, 0.05M disodium tetraborate+0.1M KCl; pH 12, 0.01M KOH+0.1M KCl). The voltammetric behaviour of compounds of the invention can be grouped into three types: (1) chemically and electrochemically reversible behaviour, (2) chemically irreversible leading to electrochemically reversible systems involving the formation of polymeric species and (3) chemically irreversible leading to electrochemically reversible systems involving nitro containing compounds.

Example 3.1

Compounds Displaying Chemically and Electrochemically Reversible Behaviour

Figure 2:
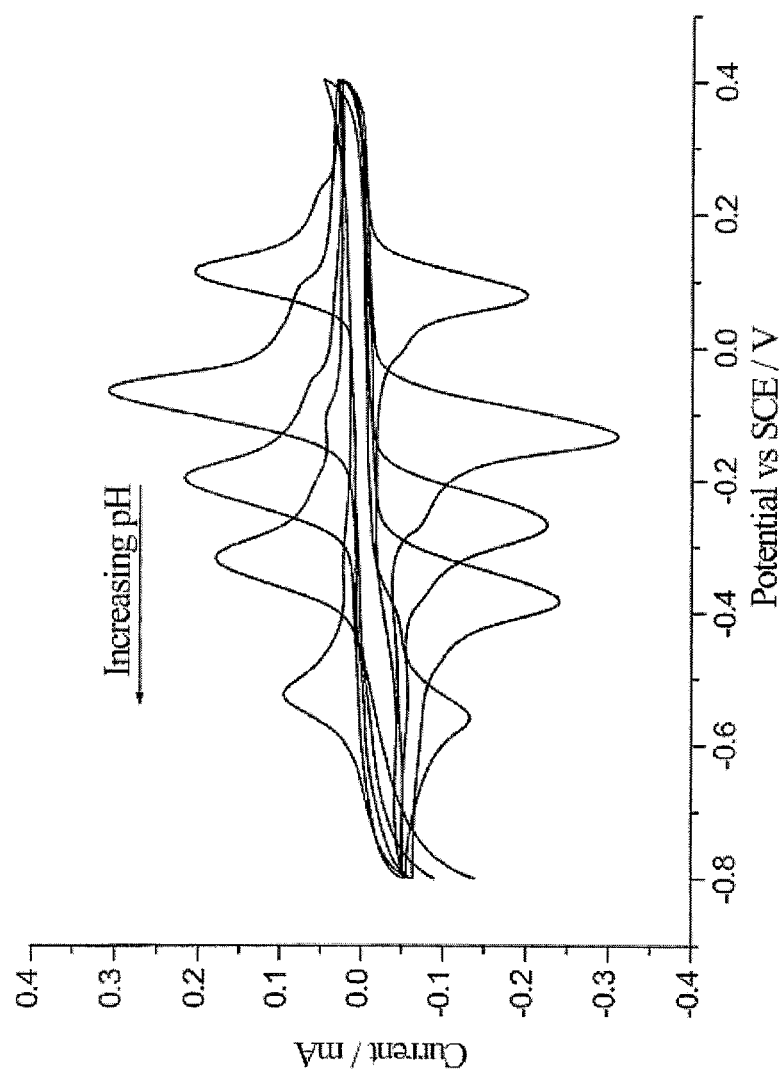
FIG. 2 shows the cyclic voltammograms of PAQ at each pH studied (pH 1, pH 4.6, pH 6.8, pH 9.2 and pH 12). Step potential 2 mV, scan rate 100 mV $s^{-1}$.

The voltammetric response of graphite powder derivatised with PAQ and DPA according to the method in Example 1 was measured. FIG. 2 shows the overlaid cyclic voltammetric responses of PAQ measured over the pH range 1-12. The peak shapes are nearly symmetrical with a slight separation of ca 20 mV between oxidative and reductive peaks at each pH. A slight shoulder at higher potential can be observed on each peak which was not observed with either DPA or anthracene. This is analogous to the voltammetry observed when anthraquinone is derivatised onto carbon powder and can be tentatively attributed to intermediate reduction/oxidation of the quinone/semi-quinone species respectively.

Figure 3A:
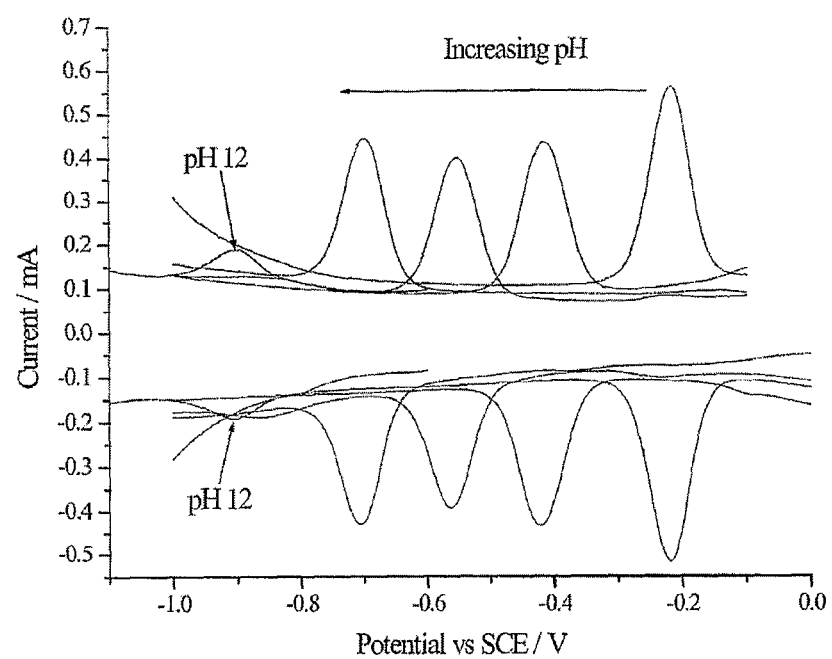
FIG. 3A is the base-line corrected oxidative and reductive square wave voltammograms of DPA at each pH studied (pH 1, pH 4.6, pH 6.8, pH 9.2 and pH 12).
Figure 3B:
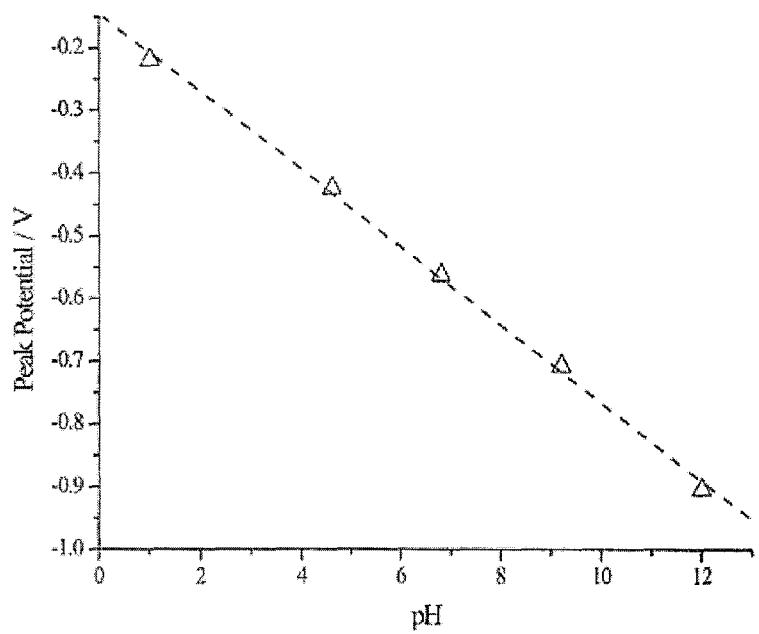
FIG. 3B is the corresponding plot of oxidative peak potential vs. pH.

FIG. 3A shows the overlaid oxidative and reductive SWV response of DPA over the pH range 1-12 and FIG. 3B shows the corresponding plot of peak potential against pH. This plot clearly shows a linear response to pH with a gradient of 61 mV/pH unit which is in excellent agreement with theory (equation 1). A comparison of the experimentally obtained potential shifts with pH for each compound with theory is given in Table 1 for each compound in this class.

TABLE 1

Comparison between theoretically calculated shift in peak potential with pH (58.1 mV/pH unit, equation 1) and experimentally determined shifts of peak potential with pH for anthracene, DPA and PAQ taken from oxidative SWV scans at 22 ± 2° C.

| Compound | Experimental Shift ± 2 (mV/pH unit) |
|---|---|
| Anthracene | 57.5 |
| 9,10-Diphenylanthracene | 61.6 |
| 9,10-Phenanthraquinone | 56.3 |

Example 3.2

Figure 4:
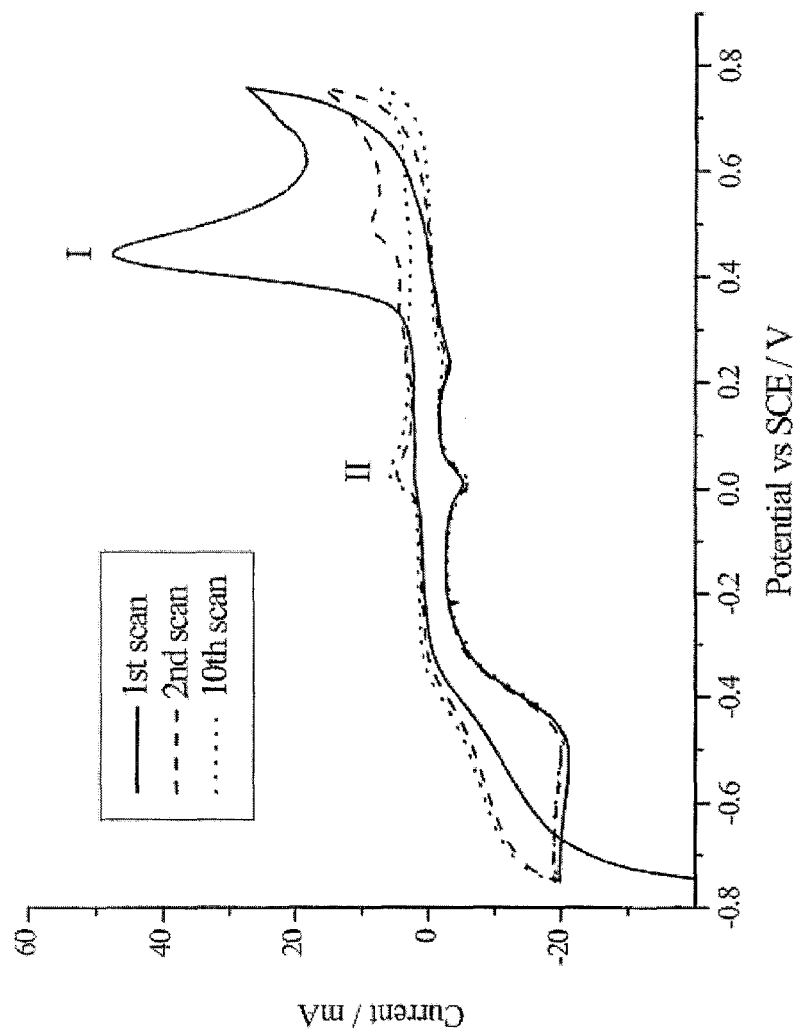
FIG. 4 shows cyclic voltammograms of diphenylamine derivatised carbon in pH 6.8 buffer showing the first, second and tenth scans.

Compounds Displaying Chemically Irreversible Behaviour Leading to Electrochemically Reversible Behaviour—Compounds which Form Polymers Cyclic voltammetry of carbon powder derivatised with diphenylamine revealed that upon first scanning in an oxidative direction a large electrochemically irreversible wave is observed at ca +0.45 V vs. SCE at pH 6.8 (FIG. 4). Upon reversing the scan direction at +1.0 V a new wave is observed at ca +0.03 V vs. SCE which upon repetitive cycling grew to give a stable, reversible redox system, whilst the large peak at +0.45 V died away after 4 cycles. This behaviour is analogous to that reported in the literature for electropolymerisation of diphenylamine in solution except that in this case the polymerisation occurs for diphenylamine physisorbed onto the surface of carbon particles in contact with an aqueous solution. The large electrochemically irreversible peak labelled (I) in FIG. 4 can be attributed to the oxidation of diphenylamine to its corresponding radical cation and subsequent polymerisation via a mechanism involving concomitant proton loss and gain as shown in scheme 3.

Scheme 3
The proposed electropolymerisation mechanism for diphenylamine

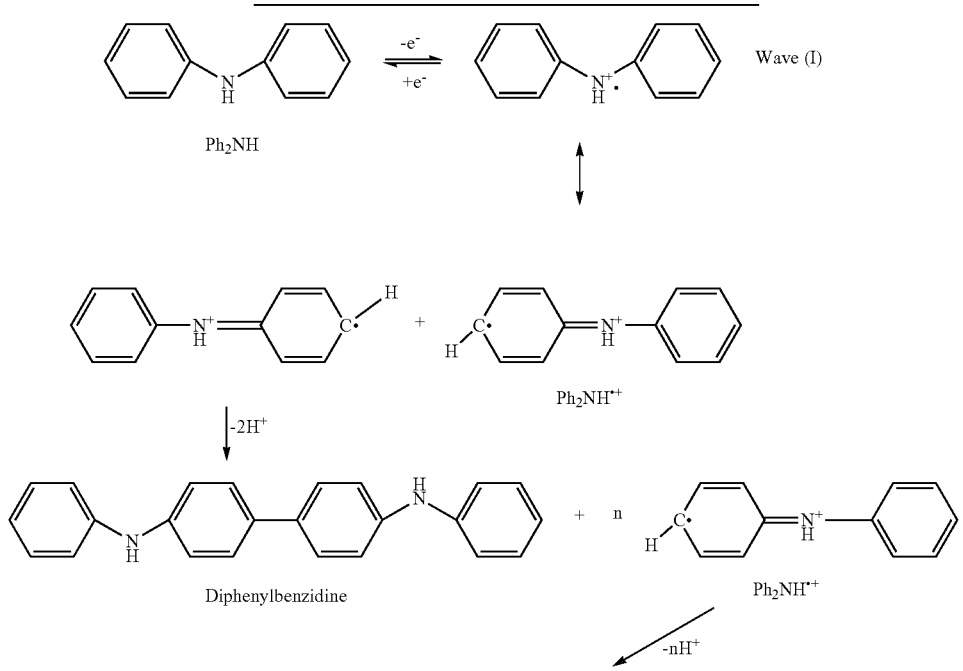

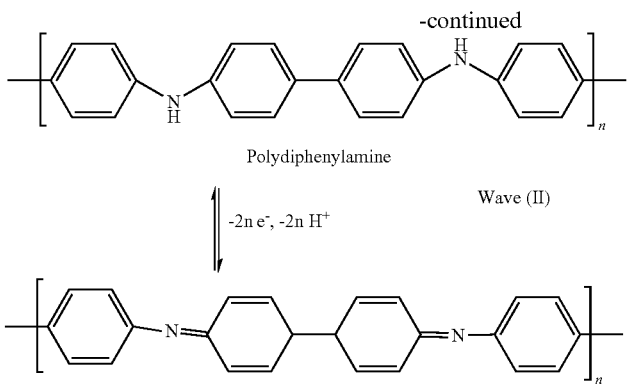

Polydiphenylamine

Wave (II)

$-2n\, e^-,\, -2n\, H^+$

Upon repetitive cycling peak (I) disappears as eventually all the diphenylamine on the surface of the carbon is polymerised. A new reversible system, labelled as (II) in FIG. 4, grows upon repetitive cycling and stabilises. This can be tentatively attributed to the redox response of the polydiphenylamine involving subsequent oxidation/reduction of the imine linkages in the polymer structure and subsequent proton loss/gain (scheme 3). It is worth noting that in non-aqueous media the polymerisation is thought to begin with the dimerisation of diphenylamine to form diphenylbenzidine and two corresponding reversible waves were reported at a higher potential than those corresponding to the polymeric species. In the present case two small reversible waves are observable at ca +0.25 V for the first few scans. These are tentatively attributed to oxidation/reduction of diphenylbenzidine, but these too die away and by the tenth scan they can hardly be observed as the dimer is further polymerised to form polydiphenylamine (scheme 3).

It was found that this voltammetric response was characteristic of diphenylamine derivatised carbon at each pH studied from pH 1-12 and that the peak potentials of both peak (I) and peaks (II) shifted in a negative direction as predicted from equation (1). Analysis of the gradient of a plot of peak potential for both the irreversible system (1) and the reversible system (II) against pH (not shown) found that each system shifted by 56 mV/pH unit and 66 mV/pH unit respectively in a linear, Nernstian fashion over the entire pH range. This suggests that carbon particles derivatised with diphenylamine which subsequently undergoes electropolymerisation to form polydiphenylamine provide not only a robust reagentless pH sensor over the pH range 1-12, but also a novel technique to prepare an electrode in situ in an aqueous environment.

Example 3.3

Compounds Displaying Chemically Irreversible Behaviour Leading to Electrochemically Reversible Behaviour—Compounds which Form Polymers Another class of polymeric films is derived from phenothiazine dyes such as toluidine blue, and importantly in the present context, methylene blue and thionin. These molecules are often used as mediators in amperometric sensors coated in Nafion films that detect biologically active molecules and enzymes such as nicotinamide adenine dinucleotide (NADH) and β-d-glucose. The redox properties of methylene blue and thionin derivatised carbon particles are more complicated than that of diphenylamine-carbon and very much dependent on pH. In solution the number of electrons transferred (n) for both methylene blue and thionin is reported to always be equal to two but the number of protons transferred (m) is reported to vary with pH such that m=3 at pH<5.4, m=2 at pH 5.4<6.0 and m=1 at pH>6.0.

Figure 5:
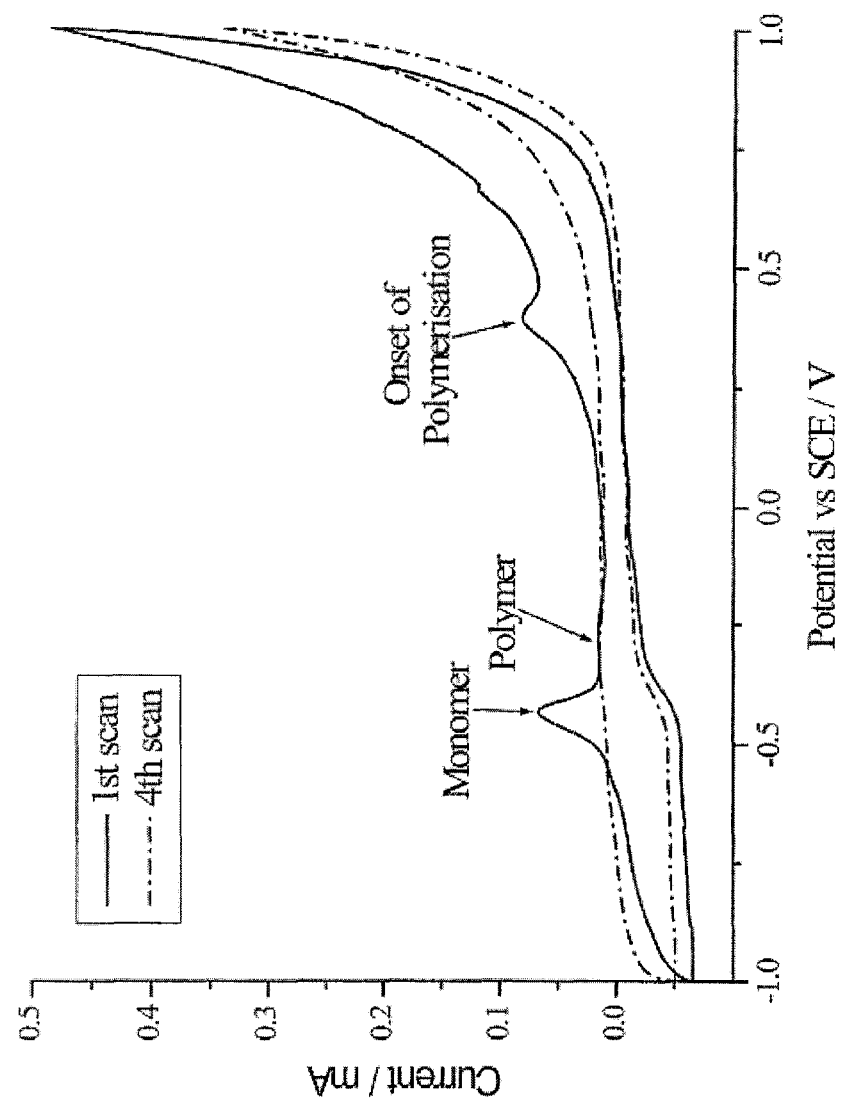
FIG. 5 shows cyclic voltammograms of thionin derivatised carbon particles immobilised on a bppg electrode in pH 12.0 (0.1M NaOH+0.1M KCl) buffer showing the first and fourth scans.

During the characterisation of both methylene blue and thionin derivatised carbon particles using cyclic voltammetry, it was observed that below a certain oxidising potential (which depended on pH but varied form +1.2 V at pH 1.0, +1.0 at pH 4.6, +0.65 V at pH 9.2 to +0.4V at pH 12.0 vs. SCE) reversible waves were observed corresponding to the oxidation/reduction of the monomeric species. If the potential was swept beyond this oxidising potential a new wave was observed which has been described in the literature as corresponding to the oxidative electropolymerisation methylene blue or thionin respectively (FIG. 5). Upon reversal of the scan direction the peaks corresponding to the reduction of the monomeric species were absent. On repetitive cycling a broad, low, undefined wave at a potential ca 0.2 V more positive than that corresponding to the monomer was observed which is analogous to that reported in the literature and has been attributed to the redox properties of the polymer (FIG. 5). Below pH 4.6 the variation of peak potential of the monomeric species with pH was found to be 86 mV/pH unit and 83 mV/pH unit for methylene blue and thionin respectively; above pH 6.8 the shift in peak potential with pH was found to be 33 mV/pH unit and 33 mV/pH. This is analogous to the behaviour reported in the literature for both species in solution. This demonstrates that carbon particles can successfully be modified by methylene blue and thionin, and that the resulting modified particles are useful in electrochemical sensors.

Example 3.4

Compounds Displaying Chemically Irreversible Behaviour Leading to Electrochemically Reversible Behaviour—Compounds which Contain Nitro Groups The behaviour of 9-NA, 6-NC and 3-NF derivatised carbon powder can be generically characterised by discussing the voltammetry observed for 6-NC. Where differences in behaviour between compounds arise they will be discussed.

Figure 6A:
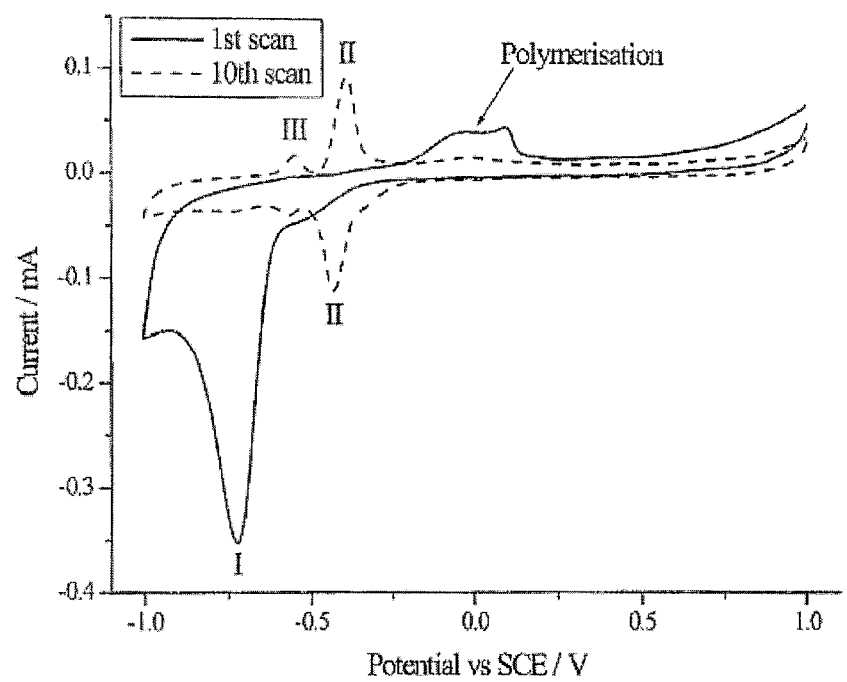
FIG. 6A shows cyclic voltammograms of 6-nitrochrysene derivatised carbon powder immobilised on a bppg electrode in pH 9.2 buffer (0.05M sodium tetraborate+0.1M KCl) showing the first and tenth scans.

Upon first scanning the freshly immobilised 6-NC in a reductive direction from +1.0 V to −1.0 V vs. SCE at pH 9.2 a large, reductive peak was observed at −0.75 V (labelled as (I) in FIG. 6A). Upon reversing the scan direction at −1.0 V no reverse peak was seen but a new oxidative peak (labelled as (II) in FIG. 6A) was observed at ca −0.25 V and a low, broad oxidative wave was also observed at ca 0.25 V. Upon repetitive cycling the electrochemically reversible system at −0.25

V stabilised while the electrochemically irreversible reductive wave at −0.75 V rapidly died away (FIG. 6A). In the case of 9-NA a further reversible wave at ca −0.55 V also grew with repetitive cycles labelled as (III) in FIG. 6B. The reductive wave in the system at −0.25 V has a pronounced shoulder on it, this will be discussed below. Both waves I and II (and III in the case of 9-NA) were found to be present at each pH in the range 1 to 12 and shifted in a Nernstian, linear fashion (where n is equal to m in equation (1) and is likely to be equal to four for the system labelled (I) and two for system (II)) for all three compounds 9-NA, 6-NC and 3-NF. Table 2 details the peak potentials of each system I and II for each compound studied at pH 6.8 for comparison while Table 3 details the shift of each peak with pH for each compound studied.

TABLE 2

A comparison of the peak potentials of system (I) corresponding to the six-electron, six-proton nitro group reduction and system (II) corresponding to the aryl hydroxylamine/aryl nitroso redox system for 9-NA, 6-NC and 3-NF at pH 6.8

| Compound | System (I) Peak Potential/V | System (II) Oxidative Peak Potential/V | System (II) Reductive Peak Potential/V |
|---|---|---|---|
| 9-Nitroanthracene | −0.722 | −0.402 | −0.428 |
| 6-Nitrochrysene | −0.654 | −0.210 | −0.254 |
| 3-Nitrofluoranthene | −0.785 | −0.107 | −0.150 |

TABLE 3

A comparison between theoretically calculated shift in peak potential with pH (58.1 mV/pH unit, equation 1) and experimentally determined shifts of peak potential with pH for system (I) and system (II) for 9-NA, 6-NC and 3-NF taken from oxidative SWV scans at 22 ± 2° C.

| | Experimental Shift ± 2 (mV/pH unit) | |
|---|---|---|
| Compound | System (I) | System (II) |
| 9-NA | 54.3 | 53.2 |
| 6-NC | 53.5 | 52.2 |
| 3-NF | 56.4 | 61.3 |

The origin of each wave will be discussed in turn but first it is worth reiterating the fact that for every compound studied the characterisation protocol discussed above was carried out on the system labelled (II) after several scans had been performed to stabilise the system. In every case the results of all three tests (many repeat scans giving a stable symmetric wave, replacement of the buffer solution with fresh solution and a linear relationship between peak current and scan rate) described in the protocol above confirmed that each compound was attached to the surface of the carbon particles at each pH studied from pH 1 to pH 12.

Comparison with the literature reveals that the voltammetric response of all the compounds studied which is described above and shown in FIG. 6A and FIG. 6B is characteristic of the electrochemical reduction of an aromatic molecule containing a nitro group and is consistent with the general mechanism shown in scheme 2.

By analogy with the reduction of nitrobenzene peak (I) corresponds to the four-electron, four-proton reduction of the nitro moiety to the corresponding arylhydroxylamine, which involves a two-electron, two-proton chemically irreversible reduction followed by a further two-electron, two-proton step.

Upon subsequent cycles the irreversible system at ca 0 V (pH 6.8) labelled as "polymerisation" in FIG. 6A can be tentatively ascribed to the formation of oligomers by the electro-oxidation of the aryl amine moiety (formed by sweeping the potential past system (I) and further reducing the arylhydroxylamine to the corresponding aryl amine) to its corresponding radical cation and subsequent polymerisation. This wave also rapidly dies away as all remaining aryl amine species on the surface of the carbon is polymerised to form what is apparently an electro-inactive polymer.

The reversible system labelled as (II) in FIG. 6A grows and stabilises after 10 scans at each pH. Again this is characteristic of the voltammetry reported in the literature and can be attributed to the chemically and electrochemically reversible two-electron, two-proton oxidation/reduction of the aryl hydroxylamine/aryl nitroso moieties. This system remains stable as long as the potential is not swept to very reducing values (ca −1.2 V at pH 6.8) whereupon the peaks gradually decrease due to some of the aryl hydroxylamine being further reduced irreversibly to the corresponding amine. A pronounced shoulder is observed at some pHs on this system, particularly in the case of 9-NA and this may possibly be due to intermediate oxidation/reduction of the aryl hydroxylamine/aryl nitro moiety.

Figure 6B:
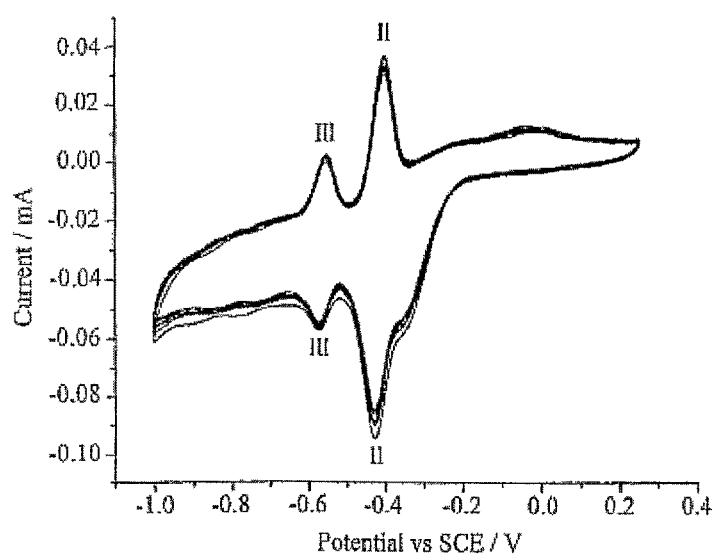
FIG. 6B: 10 CV scans 9-nitroanthracene derivatised carbon powder immobilised on a bppg electrode over the reversible systems (see text) at pH 6.8.

In the case of 9-NA, the system labelled as (III) in FIG. 6B at a more negative potential than the reduction of the nitroso to hydroxylamine moiety is not characteristic of a nitro reduction. However, comparison of the voltammetric behaviour of anthracene discussed above may reveal a clue as to its identity. Comparison of the peak potentials of system (III) and its shift with pH match that of the reversible system observed in the voltammetry of anthracene which undergoes a two-electron, two-proton ring reduction at the 9 and 10 positions shown above in scheme 1.

A two-electron, two-proton reduction at the 9 and 10 position in 9-NA is still possible, although the presence of the electron withdrawing nitro group may affect the redox potential slightly. Furthermore, it was also observed that as the pH was increased from pH 1 to pH 6.8 that the magnitude of the peak current also decreased corresponding to a decrease in the local proton concentration.

Example 3.5

Figure 7:
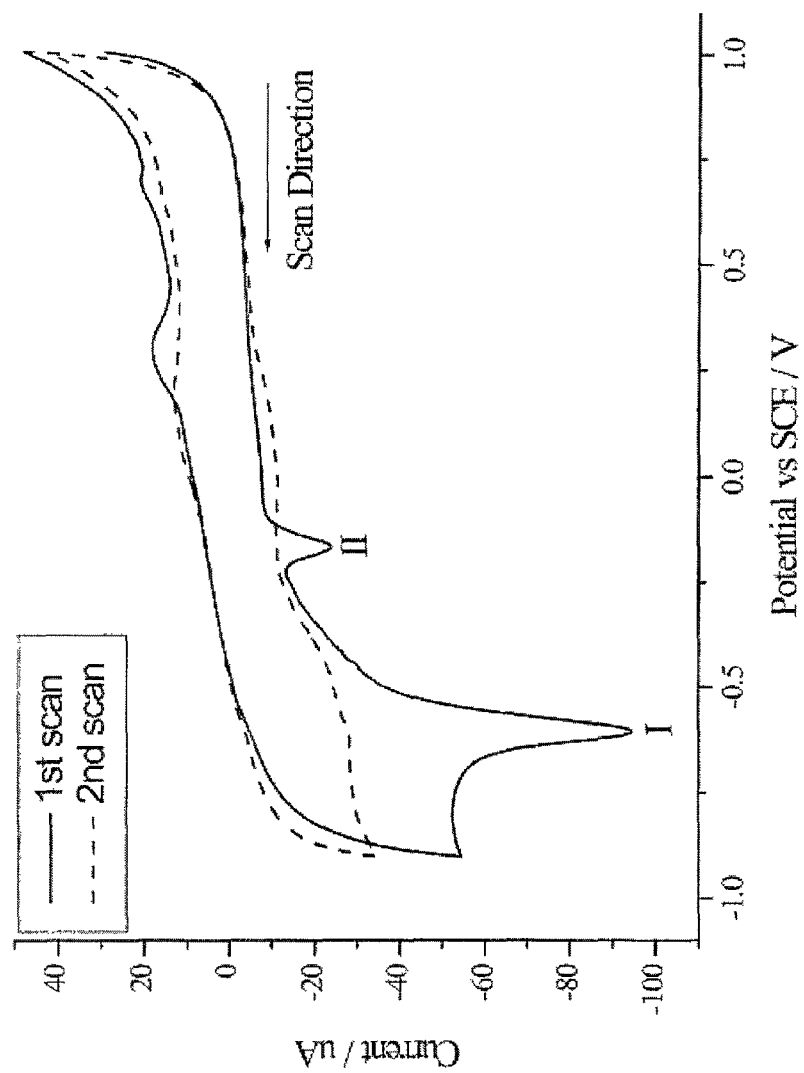
FIG. 7 shows cyclic voltammograms of FBK derivatised carbon powder immobilised on a bppg electrode in pH 4.6 buffer (0.1M acetic acid+0.1M sodium acetate+0.1M KCl) showing the first and second scans.
Figure 8A:
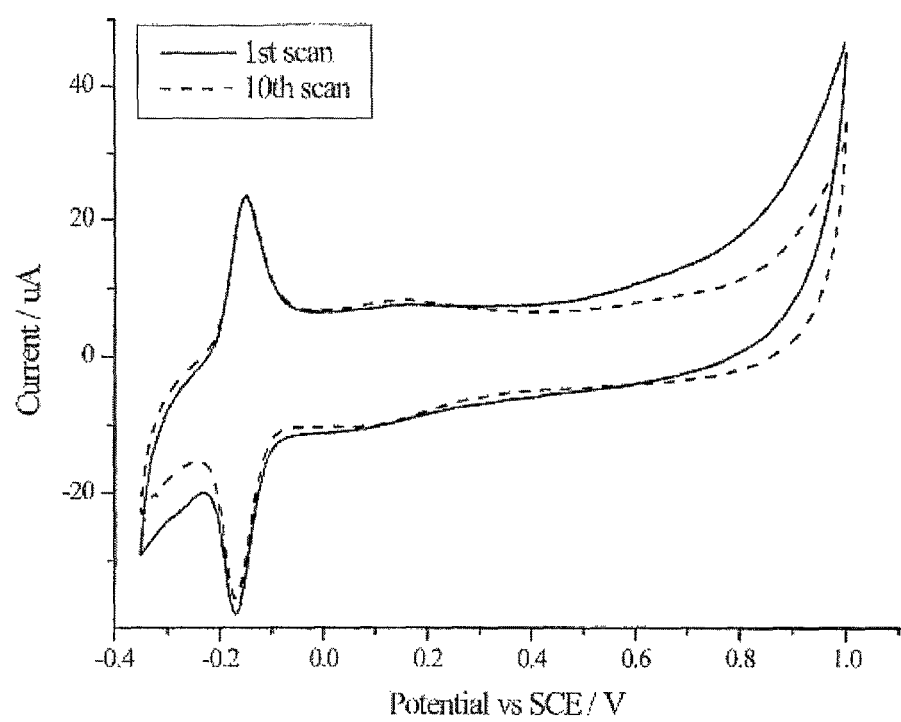
FIG. 8A cyclic voltammograms of FBK derivatised carbon powder immobilised on a bppg electrode in pH 4.6 buffer (0.1M acetic acid+0.1M sodium acetate+0.1M KCl) where the potential is cycled around system (II) only (see text) showing the first and tenth scans.
Figure 8B:
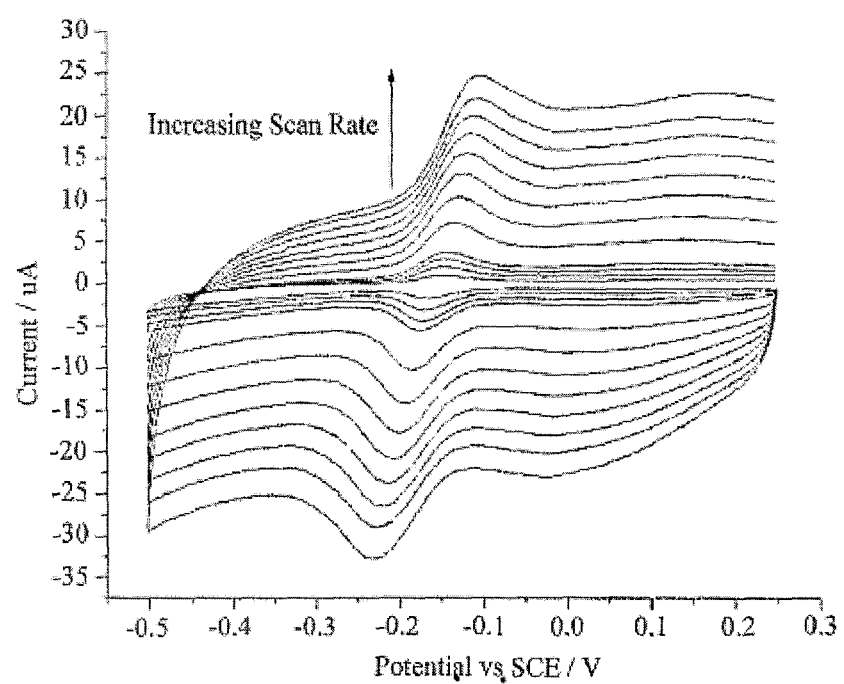
FIG. 8B: CV scans of the same system with varying scan rate (25, 50, 75, 100, 200, 300, 400, 500, 600, 700, 800 and 900 mV s$^{-1}$)

Compounds Displaying Chemically Irreversible Behaviour Leading to Electrochemically Reversible Behaviour—Compounds which Contain Nitro Groups The voltammetry of FBK (2,5-dimethoxy-4-[(4-nitrophenyl)azo]benzenediazonium chloride) derivatised carbon was also investigated. In this compound the reduction of the nitro group is further complicated by the presence of an azo linkage. Initially a reductive scan was performed using cyclic voltammetry at each pH. Two irreversible peaks were observed (FIG. 7), the first at higher potential (labelled as (II) in FIG. 7) is as yet unidentified (see below) while the latter at more negative potential is characteristic of the now familiar four-electron, four-proton reduction of the nitro group (labelled as (I) in FIG. 7). However the voltammetry of FBK differs from the compounds discussed above because on reversing the scan direction at −1.0 V no reverse peak was observed for the nitro reduction as expected, but no new oxidative peaks corresponding to the hydroxylamine moiety were observed (although there is again some evidence of possible polymerisation due to the amine being oxidised to its radical cation as a low, broad peak is observed above 0 V with the exact potential dependant on pH.) Upon subsequent repeat cycles no peaks, either reductive or oxidative are observed at any pH. However, each system, (I) and (II), was found to shift linearly and in a Nernstian fashion with pH. The nitro system shifted by 57 mV/pH unit while system (II) shifted by 61 mV/pH unit. In order to understand the electrochemistry further experiments were undertaken using CV where the potential was swept in a negative direction as far as the first unidentified system where upon the scan direction was reversed just after a peak had been observed. It was found that this produced a stable reversible system which, when the characterisation protocol was performed upon it, confirmed that the FBK was derivatised onto the carbon particles consistent with other studies of diazonium salts derivatised onto carbon through a chemical bond. FIG. 8A shows this reversible system at pH 4.6 and FIG. 8B shows the cyclic voltammograms with varying scan rate used in the characterisation protocol. It is only when the potential is swept beyond system (II) and the nitro reduction corresponding to (I) occurs that all subsequent signals in repeat scans are lost. Having confirmed that the FBK was immobilised onto the carbon surface and was not desorbing, another explanation for this behaviour was sought.

Figure 9:
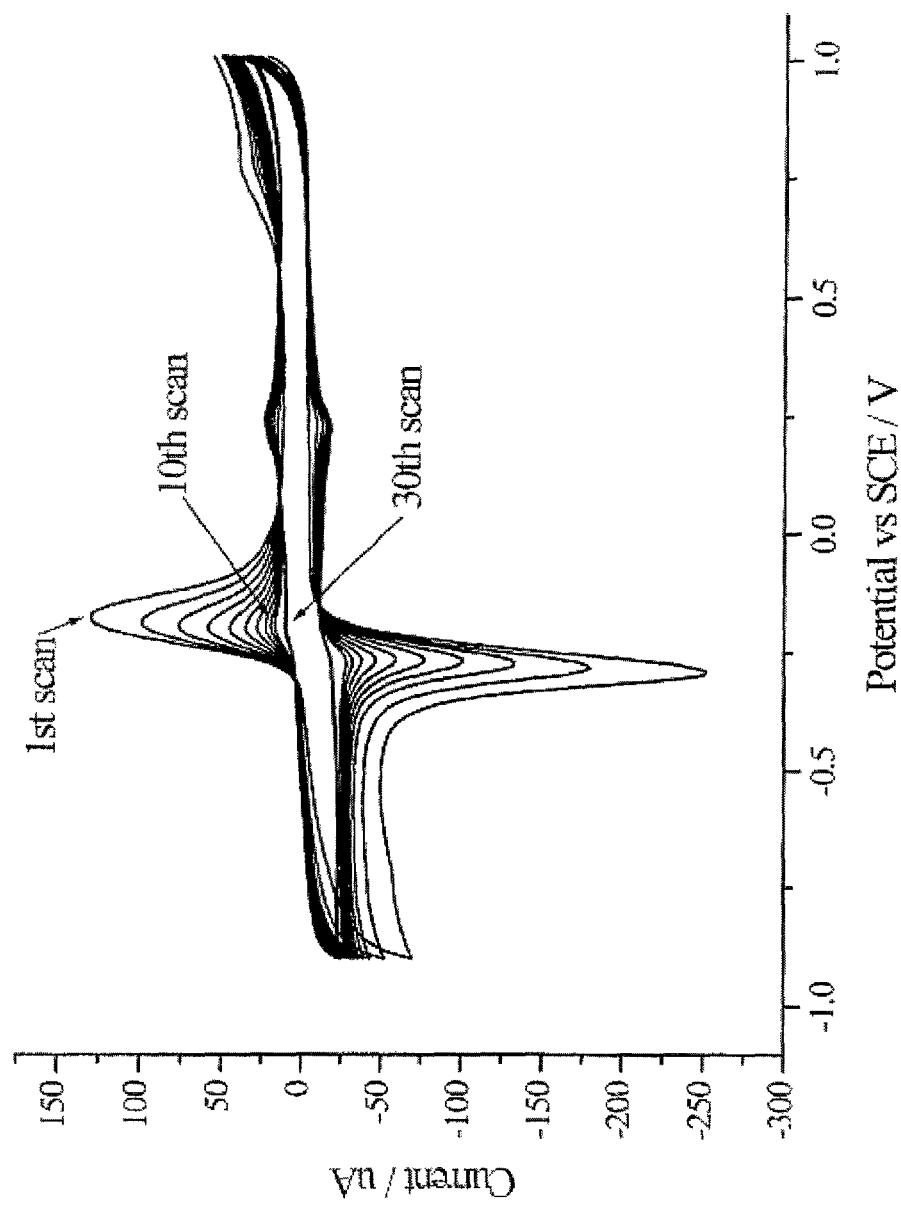
FIG. 9 shows thirty repeated CVs of azobenzene derivatised carbon at pH 4.6 showing the effect of sweeping down to very negative potentials.

Azobenzene was then derivatised onto carbon particles, and it was verified that it was indeed physisorbed onto the carbon surface using the characterisation protocol described above. Cyclic voltammetry at each pH was recorded. FIG. 9 shows the results of thirty cycles for azobenzene-carbon at pH 4.6. A reversible system is observed with a peak separation of 130 mV at ca −0.3 V which is close to the potential observed for system (II). Furthermore it can be seen that although the azobenzene was physisorbed onto the surface of the carbon and was not observed to desorb at any pH, if the potential is swept to very negative potentials of ca −1.0 V vs. SCE the azobenzene peak is seen to gradually die away. One possible explanation for the large peak separation is that protonation effects influence the redox kinetics of adsorbed films of azobenzene such that the reaction kinetics are sluggish and quasi-reversible when compared to azobenzene in solution where they take on more reversible character. At pH 1.0 no reverse (oxidative) peak is observed implying that the reduced form of the azo moiety is either irreversibly protonated, or the protonation induces cleavage of the azo linkage. This cleavage is also a likely explanation for the gradual loss of any voltammetric signal from the azobenzene-carbon if the potential is scanned to very negative potentials as the N—N bond may be further reduced.

Given these results, one hypothesis that explains the behaviour of FBK carbon is given in scheme 4.

Scheme 4
The proposed mechanistic pathway for the electrochemical reduction of FBK derivatised carbon powder

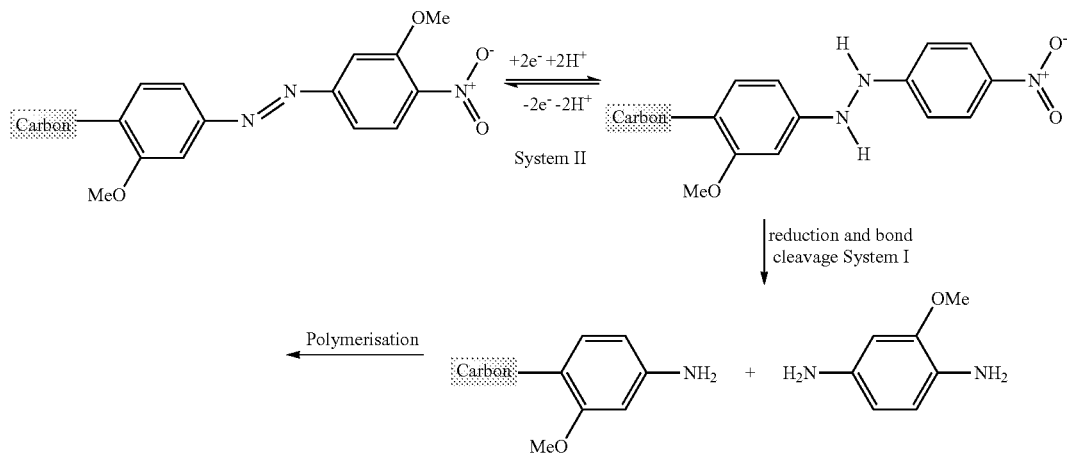

Initially scanning in a negative direction from +1.0 V vs. SCE first the azo linkage is reduced in a two-electron, two-proton step to the corresponding hydrazo form which gives a corresponding Nernstian shift in peak potential with pH as is observed experimentally. If the potential is then reversed the corresponding oxidative process occurs and the system behaves reversibly and is stable over many scans. However, if the potential continues to be swept to more reducing values then the nitro group is reduced which also leads to the hydrazo-link being cleaved due to nitro reduction occurring at such negative potentials. Upon reversal of the scan direction no oxidation peaks corresponding to either the nitro group (as expected) or the azo linkage (because it has been cleaved) are observed. However a large broad wave that is characteristic of amine polymerisation is observed between 0.0 to +0.4V depending on pH. After which no further redox processes are observed in any of the repeated voltammograms. This hypothesis is supported by the mechanistic studies of Heyrovský et al. whose polarograms are consistent with a mechanism involving reduction of a nitro group with subsequent cleavage of a hydrazo-linkage. Furthermore the peak area of the nitro reduction peak was always found to be significantly greater than six times the area of the reduction peak corresponding to system (II), which by itself is not proof that this mechanism is correct but certainly provides further support in favour of hydrazo cleavage occurring after the nitro group reduction.

It has thus been demonstrated that despite the complicated mechanisms, product interference and other substituent group interactions when nitro compounds in accordance with the invention are reduced, a large and clearly resolved irreversible peak corresponding to the four-electron, four-proton reduction of the $NO_2$ moiety can be observed. The peak potential of this peak shifts in a linear Nernstian fashion with pH as detailed in Table 3. These compounds derivatised onto carbon powder therefore present ideal candidates from which to manufacture so-called "single-shot" disposable reagentless pH sensors for use in environments where a disposable sensor may be preferred to a reusable one, such as in sewage and other unpleasant effluents.

Example 4 pH Tests at Elevated Temperatures

In this example, the response of four compounds to pH at temperatures ranging from 20° C. to 70° C. was studied. The experimental results obtained were varied with those predicted theoretically using equation 1.

It can be seen from equation (1) that as the temperature is increased, so too does the gradient of a plot of peak potential against pH. A further point to consider is how the pH of a solution will vary with temperature as the dissociation constants of the components of the buffer solution vary as the temperature is changed. Therefore the response of PAQ, DPA, anthracene and 9-NA to pH at elevated temperatures was studied using four IUPAC buffers (pH 1.5, 0.1M potassium tetraoxalate +0.1M KCl; pH 4.6, 0.1M acetic acid+0.1M sodium acetate+0.1M KCl; pH 6.8, 0.025M $Na_2HPO_4$+0.025M $KH_2PO_4$+0.1M KCl; pH 9.2, 0.05M disodium tetra borate+0.1M KCl) which have a known pH at each temperature studied.

Figure 10:
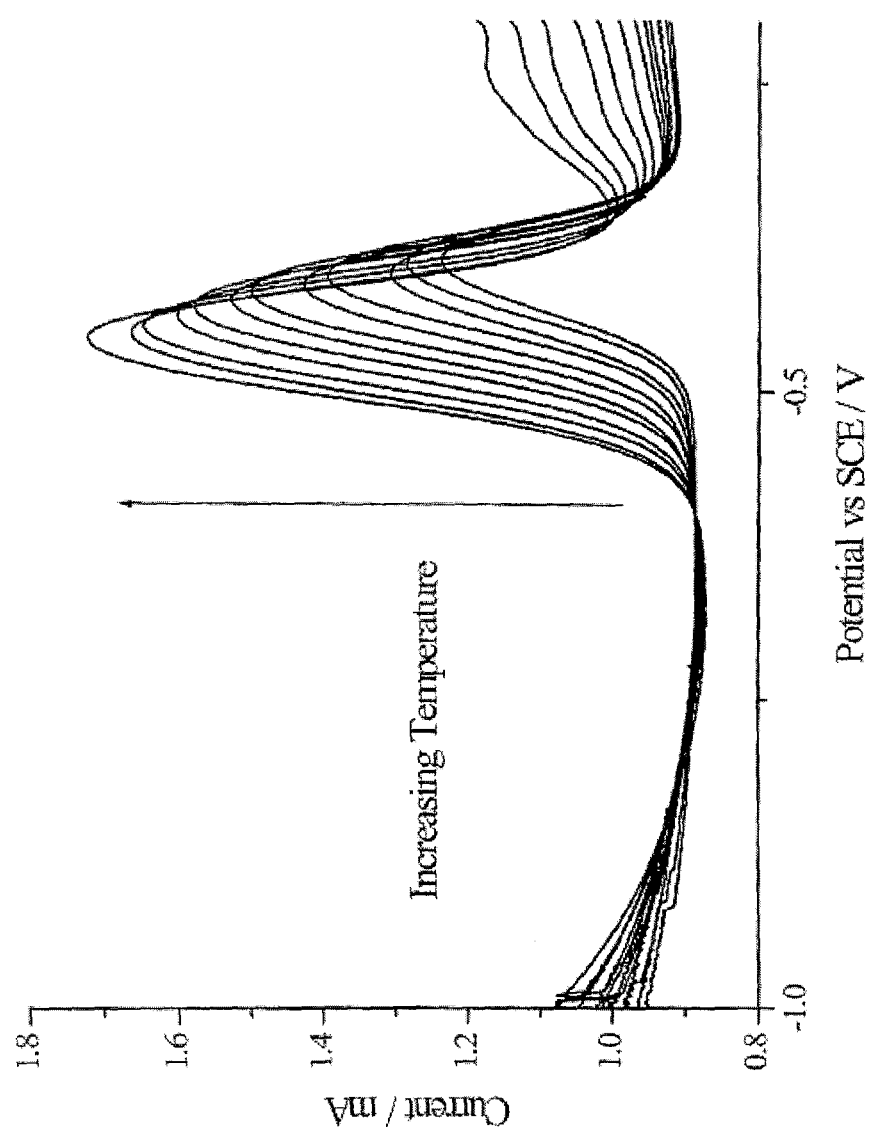
FIG. 10 shows baseline corrected oxidative SWV voltammograms of DPA-carbon at pH 4.6 (0.1M acetic acid+0.1M sodium acetate+0.1M KCl) buffer over a temperature range of 25-80° C. in 5° C. increments.

FIG. 10 shows the effect of temperature on the SWV voltammetry of DPA at pH 4.6 showing that elevated temperatures produce enhanced peak currents. It is also worth noting that the peak potential shifts in a negative direction with increasing temperature as predicted by equation (1). This behaviour is characteristic of all the compounds selected for investigation at high-temperature. Table 4 details the shift of each compound with pH at each temperature and compares them to the theoretical predictions of equation (1). Good agreement is found over the entire temperature and pH range between theory and experiment thus showing that carbon powders derivatised with a variety of different compounds can be used as reagentless pH sensors from pH 1-9 at elevated temperatures up to 70° C.

TABLE 4

A comparison between theoretically calculated (equation 1) and experimentally determined shifts of peak potential with pH for anthracene, DPA and PAQ taken from oxidative SWV and 9-NA (nitro reduction wave) taken from CV voltammograms over the temperature range 20-70° C.

| Temperature | Theoretical Shift | Experimental Shift ± 2 (mV/pH unit) | | | |
|---|---|---|---|---|---|
| (° C.) | (mV/pH unit) | Anthracene | DPA | PAQ | 9-NA |
| 20 | 58.1 | 57.5 | 61.6 | 56.3 | 52.8 |
| 30 | 60.1 | 64.8 | 59.2 | 55.3 | 50.0 |
| 40 | 62.1 | 66.1 | 60.6 | 57.2 | 57.8 |
| 50 | 64.1 | 65.3 | 61.4 | 61.2 | 53.7 |
| 60 | 66.1 | 65.2 | 62.2 | 61.2 | 52.2 |
| 70 | 68.1 | 65.9 | 61.2 | 62.0 | 60.2 |

It will be apparent to those skilled in the art that modifications may be made to the invention as described above without departing from the scope of the claims below.

DETAILED DESCRIPTION OF THE SECOND PREFERRED ASPECT OF THE INVENTION

The second preferred aspect of the present invention is concerned with the use of composition comprising carbon and a compound which is a nitrobenzene derivative of formula (I):

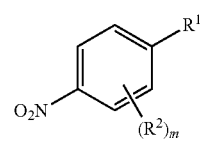

wherein
R[1] represents a group of formula —Y or —X—Y wherein Y is selected from hydrogen, hydroxy, $C_{1-4}$ alkyl and —$NR^3R^4$ wherein $R^3$ and $R^4$ are the same or different and are selected from hydrogen, hydroxy, $C_{1-4}$ alkyl and $C_{1-4}$ alkoxy, and wherein X represents a group of formula —$(CR^5R^6)_n$— wherein n is 0 or an integer from 1 to 4 and $R^5$ and $R^6$ are the same or different and are selected from hydrogen, hydroxy, $C_{1-4}$ alkyl, $C_{1-4}$ alkoxy or $R^5$ and $R^6$ together form a group of formula =O or =$NR^7$ wherein $R^7$ is selected from hydrogen, hydroxy, $C_{1-4}$ alkyl and $C_{1-4}$ alkoxy;
$R^2$ is selected from hydroxy, halogen, $C_{1-4}$ alkyl, $C_{2-4}$ alkenyl, $C_{1-4}$ alkoxy, $C_{2-4}$ alkenyloxy, amino, $C_{1-4}$ alkylamino, di($C_{1-4}$ alkyl)amino; $C_{1-4}$ alkylthio, $C_{2-4}$ alkenylthio, nitro, cyano, —O—CO—R', —CO—O—R', —CO—NR'R'', —COR', —S(O)R' and —S(O)$_2$R', wherein each R' and R'' is the same or different and represents hydrogen, $C_{1-4}$ alkyl or $C_{2-4}$ alkenyl; and
m is 0 or an integer from 1 to 4;
or a salt thereof, which method comprises mixing powdered carbon with a compound as defined above for a time sufficient to allow the compound to partially intercalate within the carbon, and isolating the resulting modified carbon.

The individual components and aspects of the second preferred aspect of the invention will now be described in more detail.

As used herein, a $C_{1-4}$ alkyl group or moiety is a linear or branched alkyl group or moiety containing from 1 to 4 carbon atoms. Examples of $C_{1-4}$ alkyl groups and moieties include methyl, ethyl, n-propyl, i-propyl, n-butyl, i-butyl and t-butyl. For the avoidance of doubt, where two alkyl moieties are present in a group, the alkyl moieties may be the same or different.

As used herein, a $C_{2-4}$ alkenyl group or moiety is a linear or branched alkenyl group or moiety containing from 2 to 4 carbon atoms. For the avoidance of doubt, where two alkenyl moieties are present in a group, the alkenyl moieties may be the same or different.

As used herein, a halogen is typically chlorine, fluorine, bromine or iodine. It is preferably chlorine, fluorine or bromine.

As used herein the term amino represents a group of formula —$NH_2$. The term $C_{1-4}$ alkylamino represents a group of formula —NHR' wherein R' is a $C_{1-4}$ alkyl group, preferably a $C_{1-4}$ alkyl group, as defined previously. The term di($C_{1-4}$ alkyl)amino represents a group of formula —NR'R'' wherein R' and R'' are the same or different and represent $C_{1-4}$ alkyl groups as defined previously. As used herein the term amido represents a group of formula —C(O)$NH_2$.

As used herein, an alkoxy group is typically a said alkyl group attached to an oxygen atom. Similarly, alkenyloxy groups are typically a said alkenyl group attached to an oxygen atom.

An alkylthio group is typically a said alkyl group attached to a thio group. Similarly, alkenylthio groups are typically a said alkenyl group attached to a thio group.

The alkyl and alkenyl groups or moieties in the compounds used in the invention are unsubstituted or substituted by one, two or three substituents which are the same or different and are selected from hydroxy, halogen and unsubstituted $C_{1-2}$ alkoxy substituents.

As used herein, the term "partially intercalated" means that the compound defined above is partially located between sheets of carbon, rather than being located entirely between such sheets. The compound is localised within edge-plane defect sites along the surface of the carbon, which can cause a slight increase in the interlayer spacing of the carbon. It has been found that the new materials having compounds defined above partially intercalated within can be manufactured by simple processes where the compounds spontaneously partially intercalate without the need for long reaction times or coupling agents.

This partial intercalation contrasts with known materials having intercalating compounds which are fully intercalated. When full intercalation occurs, the intercalating compounds are located entirely between adjacent sheets of graphite and have the effect of pushing these sheets wide apart. This significantly increases the interlayer spacing of the carbon, which in turn allows subsequent intercalation of other, larger species. Production of carbon having fully intercalated compounds requires more experimentally and synthetically complicated processes than the new methods of the present invention.

Various methods can be used to determine whether a compound defined above has been partially intercalated within the carbon, as shown by the Examples which follow. A particularly useful technique is X-ray diffraction, which can distinguish between partially intercalated compounds and fully intercalated compounds. If the compound is fully intercalated in the carbon, then when the modified carbon is subjected to X-ray diffraction a peak will be observed corresponding to a considerably larger interlayer spacing than the native carbon which has not been modified. However, if the compound is partially intercalated, a broader peak will be observed, with the average interlayer spacing being the same as or slightly larger than the usual interlayer spacing for the carbon used. In particular, when such compounds are partially intercalated into multi-walled carbon nanotubes a significantly broader peak is observed at a slightly increased interlayer spacing.

Carbon

One form of carbon which is particularly suitable for use in the invention is graphite. The graphite is preferably in the form of powdered graphite. A suitable particle diameter is from 0.1 to 100 µm, more preferably from 1 to 50 µm and more preferably from 2 to 20 µm.

Another form of carbon which is particularly suitable for use in the invention is multi-walled carbon nanotubes. Carbon nanotubes (CNTs, also referred to herein as nanotubes) have been known for a number of years, having been discovered in 1991 (see S. Iijima, *Nature,* 1991, 56, 354). One field that has seen a large expansion in the study and use of nanotubes is electrochemistry. Carbon nanotubes are particularly useful in this field due to their noted mechanical strength, structure and good electrical conductivity. These properties have been used in electroanalytical applications ranging from catalytic detection and analysis of biological molecules such as dopamine, cytochrome c and carbohydrates, to the sensing of analytes such as hydrogen peroxide, hydrazine and TNT.

Structurally, nanotubes approximate to "rolled up" sheets of graphite and as such are relatively hydrophobic in nature. There are two main configurations of these "rolled up" sheets: single-walled carbon nanotubes (SWCNTs) which are formed as a single, hollow, graphite tube, and multi-walled carbon nanotubes (MWCNTs) which consist of several concentric graphite tubes fitted one inside the other. In the present invention MWCNTs can be used.

Suitable nanotubes include those purchased from Nanolab Inc. (Brighton, Mass., USA). The physical properties of the nanotubes can be optimised by the person skilled in the art, although exemplary nanotubes have a diameter of from 1 to 50 nm, preferably from 5 to 30 nm, and a length of from 1 to 50 µm, preferably from 5 to 30 µm. Preferably the carbon nanotubes have a relatively high purity, preferably from 80 to 100%, more preferably from 90 to 100%, most preferably from 95 to 100%.

Partially Intercalating Compounds

The compounds used in the invention are described earlier. The compounds may be in the form of nitrobenzene derivatives of formula (I) or salts thereof. The alkyl and alkenyl groups or moieties in the compounds are unsubstituted or substituted by one, two or three substituents which are the same or different and are selected from hydroxy, halogen and unsubstituted $C_{1-2}$ alkoxy substituents.

Preferably the $R^2$ substituent is selected from hydroxy, halogen, $C_{1-4}$ alkyl, $C_{2-4}$ alkenyl, $C_{1-4}$ alkoxy, $C_{2-4}$ alkenyloxy, amino, $C_{1-4}$ alkylamino, di($C_{1-4}$ alkyl)amino, $C_{1-4}$ alkylthio, $C_{2-4}$ alkenylthio, nitro or cyano. More preferably $R^2$ is selected from hydroxy, halogen, $C_{1-4}$ alkyl, $C_{1-4}$ alkoxy, amino, $C_{1-4}$ alkylamino and di ($C_{1-4}$ alkyl)amino. More preferably $R^2$ is selected from hydroxy, halogen, $C_{1-4}$ alkyl and $C_{1-4}$ alkoxy.

The number of $R^2$ substituents can vary between zero and four. Preferably the number of $R^2$ substituents, represented by m, is zero, one or two. More preferably m is zero or one, most preferably zero.

X represents a group of formula —$(CR^5R^6)_n$— where n is zero or an integer from one to four. Preferred $R^5$ and $R^6$ groups include hydrogen, hydroxy, $C_{1-2}$ alkyl and $C_{1-2}$ alkoxy, with hydrogen being preferred.

The alkyl groups or moieties in the X group are unsubstituted or substituted by one, two or three substituents which are the same or different and are selected from hydroxy, halogen and unsubstituted $C_{1-2}$ alkoxy substituents. Preferably the $R^5$ and $R^6$ groups in the X group are unsubstituted.

Preferably n is zero, one or two. Most preferably n is one.

The group Y is selected from hydrogen, hydroxy, $C_{1-4}$ alkyl and —$NR^3R^4$ wherein $R^3$ and $R^4$ are the same or different and are selected from hydrogen, hydroxy, $C_{1-4}$ alkyl and $C_{1-4}$ alkoxy. The alkyl groups or moieties in Y are unsubstituted or substituted by one, two or three substituents which are the same or different and are selected from hydroxy, halogen and unsubstituted $C_{1-2}$ alkoxy substituents. Preferably the alkyl groups or moieties in Y are unsubstituted.

Preferred Y groups are —$NR^3R^4$. When Y is —$NR^3R^4$, $R^3$ and $R^4$ are the same or different and are preferably hydrogen, hydroxy, $C_{1-2}$ alkyl or $C_{1-2}$ alkoxy. More preferably $R^3$ and $R^4$ are selected from hydrogen and $C_{1-2}$ alkyl. Most preferably both $R^3$ and $R^4$ are both hydrogen.

Preferred compounds are nitrobenzene derivatives of formula (II):

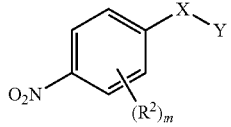

wherein:
R² is selected from hydroxy, halogen, $C_{1-4}$ alkyl and $C_{1-4}$ alkoxy;
m is 0, 1 or 2;
X represents a group of formula —$(CR^5R^6)_n$— wherein n is 0, 1 or 2 and R⁵ and R⁶ are the same or different and are selected from hydrogen, hydroxy, $C_{1-4}$ alkyl, $C_{1-4}$ alkoxy; and
Y is selected from hydrogen, hydroxy, $C_{1-4}$ alkyl and —NR³R⁴ wherein R³ and R⁴ are the same or different and are selected from hydrogen, hydroxy, $C_{1-4}$ alkyl and $C_{1-4}$ alkoxy,
or salts thereof.

Further preferred compounds are nitrobenzene derivatives of formula (III):

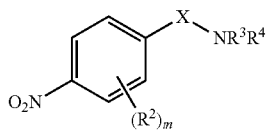

wherein:
R² is selected from hydroxy, halogen, $C_{1-4}$ alkyl and $C_{1-4}$ alkoxy;
m is 0, 1 or 2;
X represents a group of formula —$(CR^5R^6)_n$— wherein n is 0, 1 or 2 and R⁵ and R⁶ are the same or different and are selected from hydrogen, hydroxy, $C_{1-4}$ alkyl and $C_{1-4}$ alkoxy; and
R³ and R⁴ are the same or different and are selected from hydrogen, hydroxy, $C_{1-4}$ alkyl and $C_{1-4}$ alkoxy,
or salts thereof.

Preferably m is zero or one, more preferably m is zero. Preferably n is one, with R⁵ and R⁶ being the same or different and selected from hydrogen, hydroxy, $C_{1-4}$ alkyl and $C_{1-4}$ alkoxy. More preferably R⁵ and R⁶ are the same or different and are selected from hydrogen and $C_{1-4}$ alkyl. Most preferably both R⁵ and R⁶ are hydrogen.

More preferred compounds (used in the invention) are nitrobenzene derivatives of formula (IV):

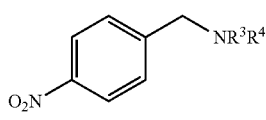

wherein R³ and R⁴ are the same or different and are selected from hydrogen, hydroxy, $C_{1-4}$ alkyl and $C_{1-4}$ alkoxy, or salts thereof. More preferably R³ and R⁴ are the same or different and are selected from hydrogen and $C_{1-4}$ alkyl.

The compounds used to make the compositions of the second preferred aspect of the invention include salts of the nitrobenzene derivatives of formulae (I) to (IV). These salts can be any suitable salt which allows does not interfere with the electrochemical mechanisms which allow the compounds to be useful in electrodes and electrochemical sensors. In particular, there can be mentioned inorganic and organic acid addition salts. Suitable inorganic acids which can be used include hydrochloric, sulphuric, phosphoric, diphosphoric, hydrobromic or nitric acid. Suitable organic acids which can be used include citric, fumaric, maleic, malic, ascorbic, succinic, tartaric, benzoic, acetic, methanesulphonic, ethanesulphonic, benzenesulphonic or p-toluenesulphonic acid. The salts may also be formed with bases, for examples with alkali metal (e.g. sodium or potassium) and alkaline earth metal (e.g. calcium or magnesium) hydroxides and organic bases such as alkyl amines, aralkyl amines or heterocyclic amines.

Without wishing to be bound by theory, it is believed that the compounds used in the invention partially intercalate into localised edge-plane defect sites along the carbon surface of both graphite and carbon nanotubes. The redox characteristics of carbon modified with these compounds show that the modified materials can be used in electrochemical sensors, for example for the measurement of pH.

In particular, the compounds used in the invention and the modified carbon of the invention are useful in the manufacture of electrodes for measuring pH. In this regard, the voltammetry of such compounds has been studied. The voltammetry of such compounds sensitive to pH, when immobilised as molecular solids onto the surface of an electrode, has been found to exhibit Nernstian behaviour which can be described according to the following Nernst equation (1):

$$E_p = E_f^0 - \frac{2.3\,RTm}{nF} pH \tag{1}$$

where $E_p$/V is the peak potential, $E^0_f$/V is the formal potential of the redox couple, R/J K⁻¹ is the universal gas constant, T/K is the temperature and m and n are the number of protons and electrons involved in the redox process respectively.

Accordingly, by studying the voltammetric response of these compounds, for example using cyclic voltammetry or square-wave voltammetry, a linear response of peak potential to pH would be expected.

Other Redox Active Materials

As well as the compounds defined above, other redox active materials can be included in the materials of the invention. These additional redox active materials may be any organic material capable of undergoing electron loss and gain. Preferably the additional redox active material is a solid phase material. When immobilised onto a substrate, e.g. glassy carbon or a basal plane pyrolytic graphite (bppg) electrode, it undergoes concomitant proton and electron loss/gain on oxidation/reduction.

The additional redox active material may be sensitive or insensitive to the species which is to be detected or measured. In either case, by measuring the potential difference between the current peaks for the compounds defined earlier and for the additional redox active material, the concentration of the species to be measured can be determined.

It is preferred that the electrodes of the invention be useful in the manufacture of pH meters, and accordingly in one embodiment the additional redox active material is sensitive to the concentration of protons. Preferably the peak potential of the additional redox active material depends on the local proton concentration. As discussed above in relation to the compounds used in the invention (i.e. the nitrobenzene derivatives or salts thereof) the voltammetry of redox active materials which are sensitive to pH has been found to show Nernstian behaviour. Accordingly, by studying the voltammetric response of these compounds, for example using cyclic voltammetry or square-wave voltammetry, a linear response of peak potential to pH would be expected.

More than one additional redox active material may be used in the invention. Suitable additional redox active materials include quinones and anthracenes, for example 9,10-anthracene, 9-nitroanthracene, phenanthraquinone (PAQ) and 1,2-napthaquinone (NQ). Other materials that can be used include azobenzene, diphenylamine, methylene blue, 3-nitrofluoranthene, 6-nitrochrysene and thionin.

When present, the additional redox active material can be combined with the modified carbon by any suitable process. For examples, in one embodiment of the invention the additional redox active material can be combined with the modified carbon by chemisorption of aryldiazonium salts using hypophosphorous acid as the chemical reducing agent. In another embodiment of the invention phenanthraquinone (PAQ) can be physiorbed onto graphite.

In another embodiment of the invention the additional redox active material can be combined with the modified carbon described previously by way of agglomeration. Such agglomerates comprises (i) carbon nanotubes having a compound as defined above which is a nitrobenzene derivative of formula (I) or a salt thereof partially intercalated within, and (ii) a binder, wherein the binder is the additional redox active material. The nanotubes, compound and additional redox active material may be as described above.

In this embodiment, the agglomerate is made by dispersing the nanotubes in a binder. The preferred method comprises combining MWCNTs having a compound of as defined above partially intercalated within (hereafter "the modified MWCNTs") and binder material in a solvent, and then precipitating the agglomerate out of the solution. In particular, the method may comprise:

(1) combining the modified MWCNTs and the binder in a solvent;
(2) adding an excess of aqueous solution in order to cause precipitation of the agglomerate out of the solvent; and
(3) recovering the agglomerate.

Preferably the solvent is a hydrophobic solvent, comprising small organic molecules. The solvent should be chosen such that the redox active compound and the carbon nanotubes are both soluble within it. Suitable solvents include all common organic solvents such as acetone, acetonitrile and dimethyl formamide.

In this embodiment, it is preferred that the additional redox active materials are hydrophobic, having a low solubility in water. This allows them, when an agglomerate is being manufactured, to mix with the carbon nanotubes in solution and results in the agglomerate precipitating out of solution when an excess of aqueous solution is added.

The agglomerate preferably comprises the modified MWCNTs and additional redox active materials only, with no other materials present. However, the agglomerate may contain some impurities such as residual solvent, left as a result of a process by which the agglomerate is be produced. Preferably these impurities comprise less than 1 wt % of the agglomerate, more preferably less then 0.5 wt %. The precise level of impurities which is acceptable in the agglomerate will depend upon how the impurities affect the voltammetry of the agglomerate.

The size of the agglomerates depends upon the nature and proportions of the components used in their preparation and the conditions of the process by which they are prepared. However, exemplary agglomerates may be approximately 10 μm in diameter and consist of bundles of nanotubes running into and throughout an amorphous molecular solid which binds the agglomerate together.

The agglomerate is preferably applied to the substrate of the electrode by way of abrasive immobilisation.

The Substrate

The substrate onto which is applied the modified carbon may be any substrate conventionally used in the manufacture of electrodes. For example, the substrate may be a basal plane pyrolytic graphite (bppg) electrode or glassy carbon, metal electrodes such as gold or platinum, or optically transparent electrodes such as those comprising ITO. The substrate preferably has good electrical contact with the carbon nanotubes, and also has a surface such that good coverage with the carbon nanotubes and redox active material can be achieved.

The Sensor

The structure of sensors according to the invention will depend upon the final application of the sensor, and depends upon the substance which the sensor is to measure and the environment in which measurement will take place. Known sensor structures may be employed in conjunction with the agglomerates and electrodes described herein.

Exemplary sensors may have a two or three terminal arrangement. Thus, they may comprise a working electrode of the invention and a combined counter and reference electrode, or a working electrode, counter electrode and separate reference electrode. The reference electrode and counter electrode can be any conventional electrodes known in the art.

The materials used in the sensor depend upon which species the sensor is intended to measure and the environment in which the sensor is to be used. In order to modify the sensor to be sensitive to a different species it is simply required for the skilled person to substitute the partially intercalating compound defined above (i.e. the nitrobenzene derivative or salt thereof) or additional redox active material with a different partially intercalating compound or additional redox active material sensitive to the species which is to be measured.

The modified carbon materials of the invention are particularly suited for use in "single-shot" pH sensors for use in "dirty" environments, such as effluent or sewage, where recovery of the sensor is likely to be undesirable.

Method for Preparing the Modified Carbon

Carbon is modified according to the method of the invention by mixing the carbon in a solvent with a partially intercalating compound defined above. Suitable solvents include common aprotic organic solvents. For example, there can be mentioned dimethyl formamide (DMF), tetrahydrofuran (THF), dimethyl sulfoxide (DMSO), acetone, acetonitrile, ethyl acetate, chloroform, methylene chloride. The solvent may be degassed or may contain dissolved gases, e.g. dissolved oxygen.

The carbon, solvent and compound are mixed for a time sufficient to allow partial intercalation of the compound into the carbon. A suitable time is 1 to 5 hours, although longer or shorter time periods can also be used. After this time the modified carbon is filtered, washed with solvent in order to remove any physiorbed species, and dried. One particular advantage of this method is that it can proceed without the need for a coupling agent.

The relative amount of the compound and carbon can be chosen by the skilled person according to the end use of the modified carbon.

Surprisingly the compounds used in the invention spontaneously partially intercalate into the carbon. The resulting materials are robust, for example when used in electrochemical sensors, producing stable responses at elevated temperatures. Furthermore, the compounds partially intercalate at a high level, i.e. a large amount of the compounds can be partially intercalated. This results in large current response and high sensitivity.

Examples of the Second Preferred Aspect of the Invention

All reagents were obtained from Aldrich (Gillingham, UK) with the exception of potassium chloride (Riedel de Haën, Seelze, Germany) tetrabutylammonium perchlorate (TBAP), lithium perchlorate (Fluka Chemicals, Gillingham, UK) acetonitrile (synthesis grade, 99.99% anhydrous, Fischer Scientific, Loughborough, UK) diethyl ether (British Drug House Chemicals, Poole, UK) and were of the highest grade available and used without further purification.

4-nitrobenzylamine (4-NBA) was obtained as the hydrochloride salt. In order to liberate the free amine the following procedure was used: 4-nitrobenzylamine hydrochloride salt (2.0 g, 0.011 mmol) was dissolved in water (40 cm$^3$) and sodium hydroxide (20 cm$^3$ of a 1M aqueous solution) was added. The solution was stirred for 2 hours, after which time the solution was washed with diethyl ether (2×50 cm$^3$). The combined organic layers were washed with brine (50 cm$^3$), dried over MgSO$_4$, filtered and concentrated in vacuo to afford 4-nitrobenzylamine (1.2 g, 78% yield) as a red crystalline solid which was used without further purification. The corresponding nuclear magnetic resonance spectrum was recorded and compared with library spectra in order to confirm that the pure compound had been re-crystallised. The crystals of 4-NBA were stored in an air-tight container at 4° C. prior to use.

Aqueous solutions were prepared using deionised water from an Elgastat (Elga, UK) UHQ grade water system with a resistivity of not less than 18.2 MΩ cm. Non-aqueous solutions were prepared using acetonitrile (supplied as 99.99% anhydrous), which was dried over 5 Å molecular sieves for 24 hours prior to use to remove any trace water content. Cyclic voltammetric measurements were made after degassing the solution with pure N$_2$ gas (BOC gases, Guildford, Surrey, UK) for 30 minutes and carried out at 20±2° C.

Synthetic graphite powder (2-20 μm diameter) was purchased from Aldrich. Multiwalled carbon nanotubes (purity >95%, diameter 10-40 nm, length 5-20 μm) were purchased from NanoLab Inc. (Brighton, Mass., USA) and were used without further purification.

Solutions of known pH in the range pH 1.0 to pH 12.0 were made up in deionised water as follows: pH 1.0, 0.10 M HCl; pH 4.6, 0.10 M acetic acid+0.10 M sodium acetate; pH 6.8, 0.025 M Na$_2$HPO$_4$+0.025 M KH$_2$PO$_4$; pH 9.2, 0.05 M disodium tetraborate; pH 12, 0.01M sodium hydroxide. These solutions contained in addition 0.10 M KCl as supporting electrolyte. pH measurements were performed using a Jenway 3030 pH meter.

Electrochemical measurements were recorded using a μAutolab computer controlled potentiostat (Ecochemie, Utrecht, Netherlands) with a standard three-electrode configuration. All experiments were carried out in a glass cell of volume 25 cm$^3$. A basal plane pyrolytic graphite electrode (bppg, 0.20 cm$^2$, Le Carbone Ltd, Sussex, UK) acted as the working electrode (see below). A platinum coil (99.99% Goodfellow, Cambridge, UK) acted as the counter electrode. The cell assembly was completed either by using a saturated calomel electrode (SCE, Radiometer, Copenhagen, Denmark) as a reference electrode in aqueous solution, or by using a silver wire (99.99% Goodfellow, Cambridge, UK) as a quasi-reference electrode in non-aqueous solution.

Unless stated otherwise cyclic voltammograms were recorded using the following parameters: step potential 2 mV, scan rate 100 mVs$^{-1}$. Square-wave voltammetric parameters were as follows: frequency 12.5 Hz, step potential 2 mV and amplitude 25 mV.

Scanning electron microscopy (SEM) images were recorded using a Jeol 6500F instrument. High resolution transmission electron microscopy (HRTEM) images were recorded using a Jeol 2010F instrument.

X-ray powder diffraction experiments were carried out using a Panalytical Xpert Pro instrument utilising X-ray radiation from the copper Kα$_1$ band (λ=1.54 Å).

Example 5

Protocol for the Derivatisation of Graphite Powder and Multiwalled Carbon Nanotubes (MWCNTs) with 4-NBA and their Abrasive Immobilisation onto the Surface of a Bppg Electrode Derivatisation of graphite powder (0.5 g) or MWCNTs (50 mg) with 4-nitrobenzylamine (4-NBA) was achieved by stirring either the graphite powder sample or the MWCNT sample in a solution of 4-NBA in acetonitrile (10 mM, 25 cm$^3$) for 120 minutes at room temperature unless otherwise stated. Next, the sample was filtered under suction, washed with acetonitrile (5×50 cm$^3$) to remove any physisorbed species and air dried for 12 hours. After which, the sample was stored in an air-tight container prior to use.

The derivatised carbon powders or MWCNTs were then abrasively immobilised onto the surface of a clean bppg electrode prior to any electrochemical experiment. This was achieved by initially polishing the bppg electrode on glass-polishing paper (H00/240), after which it was polished on silicon carbide paper (P1000C) for smoothness. The 4-NBAcarbon (i.e. graphite having 4-NBA partially intercalated within) or 4-NBAMWCNTs (i.e. MWCNTs having 4-NBA partially intercalated within) were then abrasively immobilised onto the bppg electrode by gently rubbing the electrode surface on a fine filter paper (Whatman) containing the 4-NBAcarbon or 4-NBAMWCNTs.

Example 6

Voltammetric Characterisation of Graphite Powder and MWCNTs Derivatised with 4-Nitrobenzylamine Cyclic voltammetry (CV) was used in order to confirm that 4-NBA molecules are attached onto the graphite powder (4-NBAcarbon), or onto the MWCNTs (4-NBAMWCNTs), which themselves are abrasively immobilised onto a bppg electrode. A standard protocol (given below) was employed over the entire pH range (pH 1.0 to pH 12.0).

Figure 14:
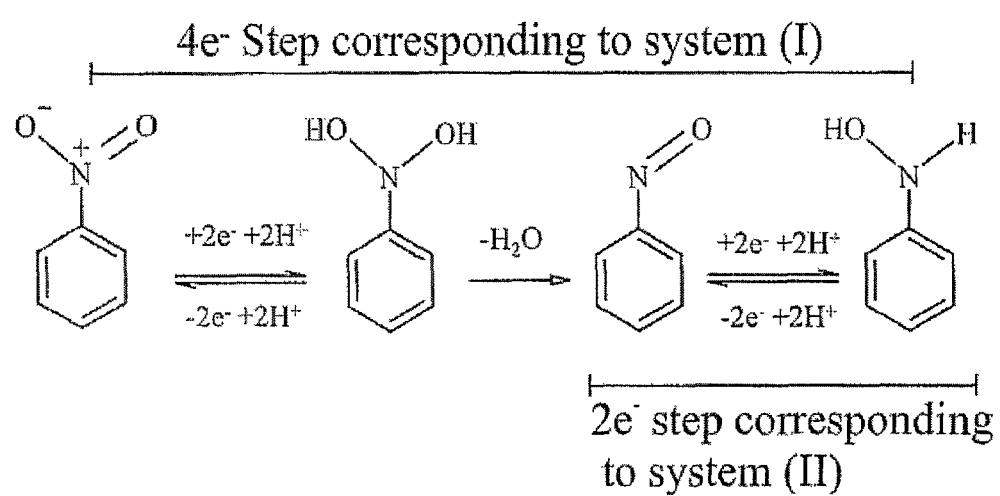
FIG. 14 discloses the general mechanism for the electrochemical reduction of an aryl nitro moiety illustrated here by nitrobenzene.
Figure 15A:
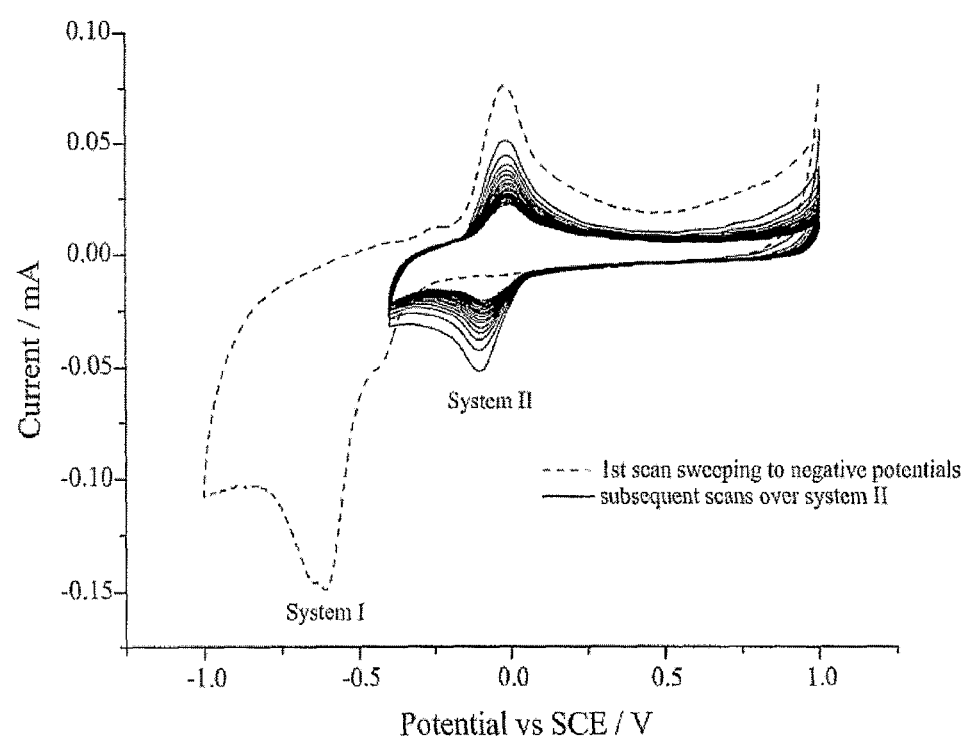
FIG. 15A shows twenty consecutive cyclic voltammograms of 4-NBAcarbon in pH 6.8 buffer.

First, twenty repeat scans were recorded to ensure that the redox species in question (4-NBA) is stable when in contact with an aqueous solution and does not desorb from the electrode surface. FIG. 15A shows twenty repetitive cycles of 4-NBAcarbon on bppg in pH 6.8 buffer. As can be seen from FIG. 3A, it is necessary to sweep the potential in a reducing direction to ca. −1.0 V vs. SCE, past an irreversible redox process at ca. −0.6 V vs. SCE (labelled as "system I" in FIG. 15A and FIG. 14), in order to generate an electrochemically almost-reversible couple at ca −0.1 V vs. SCE (labelled as "system II" in FIG. 15A and FIG. 14). The exact potentials of the redox processes discussed above will depend on the pH of the solution. At every pH studied in the range pH 1.0 to pH 12.0 a wave shape that was almost symmetrical and had a slight peak to peak separation that increased with increasing scan rate was observed. It was found that after twenty repetitive scans the peak currents (which were initially found to decrease slightly) remained stable and that the charges (peak areas) of both the oxidative and reductive peak processes were almost equal to each other (FIG. 15A).

Figure 15B:
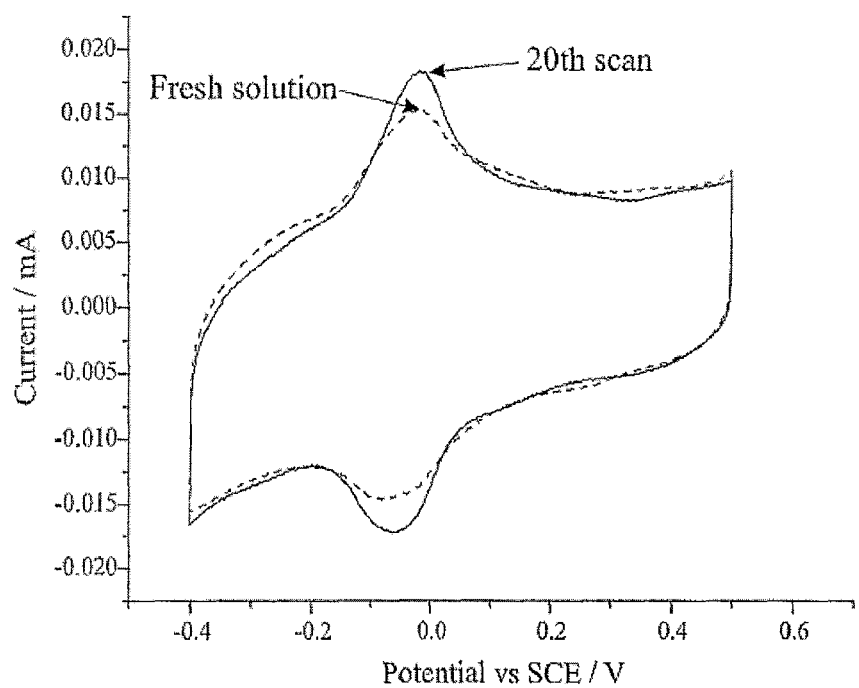
FIG. 15B shows overlaid cyclic voltammograms recorded before and after replacing the pH 6.8 solution with fresh solution.

The next step was to replace the electrolyte solution with fresh solution and record the voltammetric response. The corresponding cyclic voltammograms were found to overlay the last scan at every pH studied, thereby confirming that the electroactive species remains on the electrode and is not released to solution. FIG. 15B shows the overlaid CVs after replacing pH 6.8 solution with fresh solution.

Figure 15C:
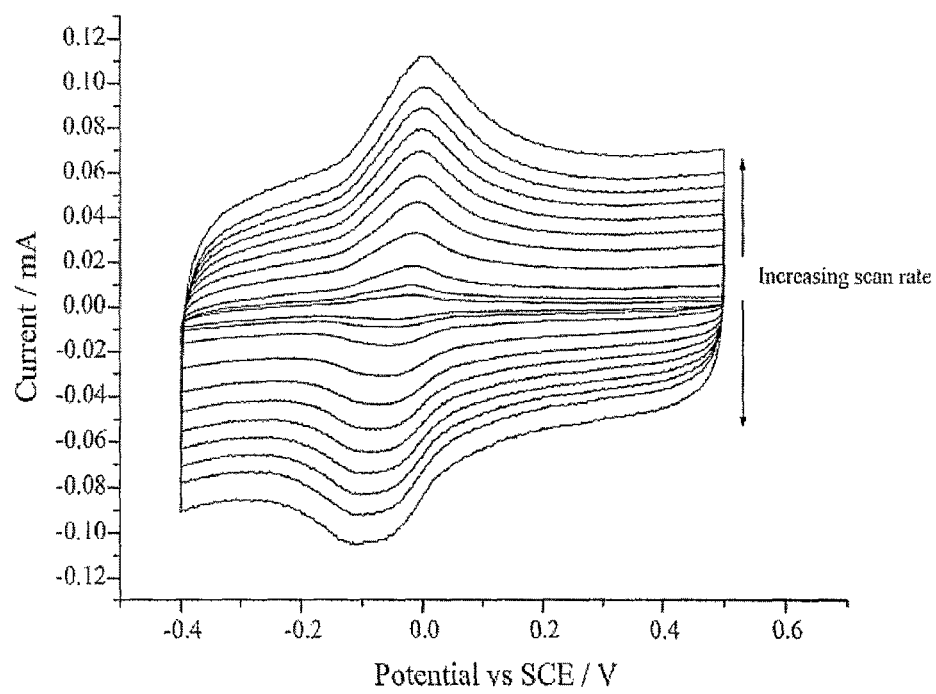
FIG. 15C shows overlaid cyclic voltammograms of 4-NBAcarbon recorded after formation of the reversible couple corresponding to system II at varying scan rates (25, 50, 100, 200, 300, 400, 500, 600, 700, 800, 900 mVs$^{-1}$) in pH 6.8 buffer.
Figure 15D:
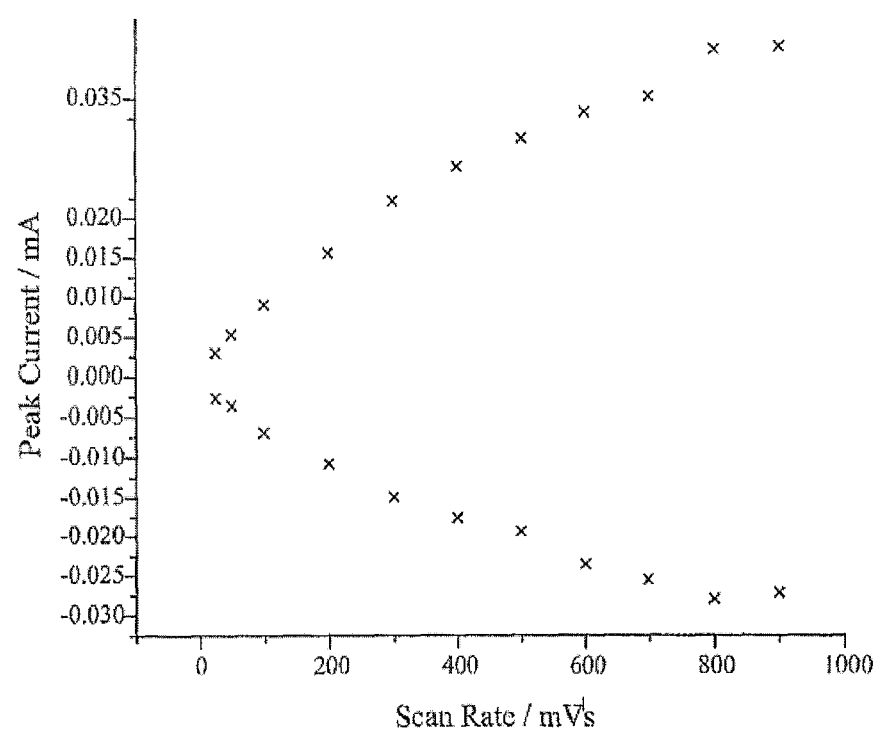
FIG. 15D shows the corresponding plot of peak current vs. scan rate.

Finally, after formation of the reversible couple (system II), as described above, the scan rate was varied from 25 to 900 mVs$^{-1}$ (FIG. 15C) and a plot of peak current versus scan rate (FIG. 15D) was found to be almost linear, consistent with a surface bound species. However the peak separation of (ca. 100 mV at low scan rates) is considerably larger than the theoretical zero peak to peak separation for an ideal, immobilised, electrochemically reversible species. These discrepancies may possibly be due to some slight ohmic distortion at higher scan rates and/or electrode kinetic factors. In fact the wave shapes and the variation of peak potential with increasing scan rate suggest that an electrochemically quasi-reversible immobilised system exists over the entire pH range studied.

Example 7

Voltammetric Response of 4-NBAcarbon and 4-NBAMWCNTs from pH 1.0 to pH 12.0

Having characterised these materials from pH 1.0 to pH 12.0 using cyclic voltammetry, this Example now demonstrates that these modified carbon materials can be used for the analytical sensing of pH. As shown in FIG. 14, the electrochemical reduction of aromatic nitro compounds such as 4-NBA undergoes an initial irreversible step involving four-electrons and four-protons to form the corresponding arylhydroxylamine. Upon repetitive cycling the arylhydroxylamine can then undergo a chemically reversible, electrochemically quasi-reversible oxidation to the corresponding aryl nitroso compound, involving a further two-electrons and two-protons.

The peak potentials for these processes must therefore depend on the local proton concentration and hence must be sensitive to variations in pH. The variation in peak potential with pH can be described by the Nernst equation (1) discussed earlier. In this Example n=m and is likely to be equal to two in the case of the reversible process (system II in FIG. 14).

Figure 16A:
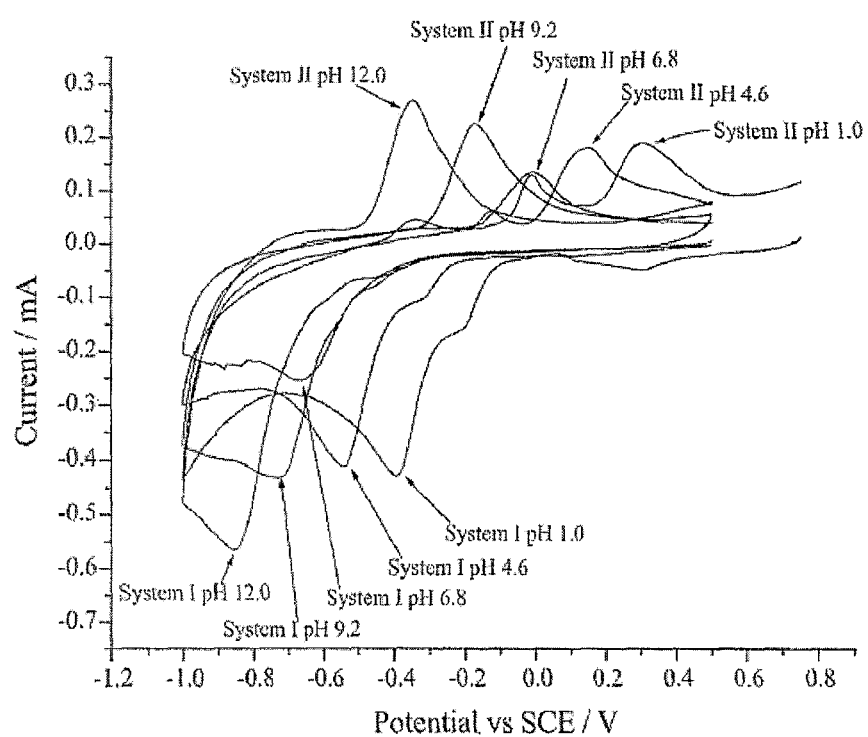
FIG. 16A shows the 1$^{st}$ cyclic voltammograms (overlaid) of 4-NBAcarbon recorded in solutions of varying pH (pH 1.0, pH 4.6, pH 6.8, pH 9.2 and pH 12.0).
Figure 16B:
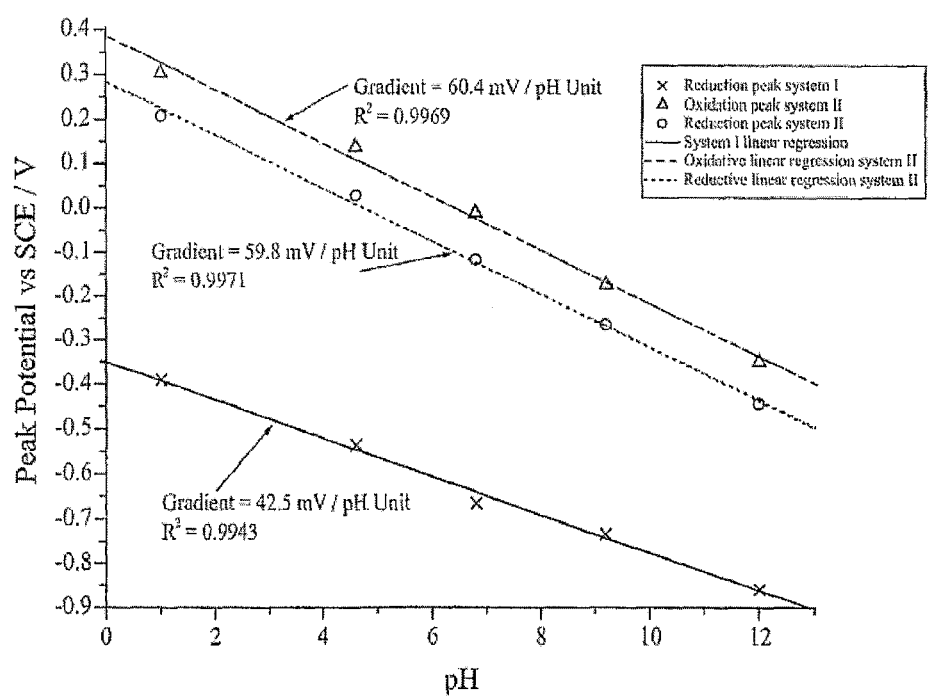
FIG. 16B shows the corresponding plot of peak potential vs. pH.

FIG. 16A shows the overlaid cyclic voltammograms (first scan) recorded in a range of solutions of differing pH (pH 1.0, 0.10 M HCl; pH 4.6, 0.10 M acetic acid+0.10 M sodium acetate; pH 6.8, 0.025 M Na$_2$HPO$_4$+0.025 M KH$_2$PO$_4$; pH 9.2, 0.05 M disodium tetraborate; pH 12.0, 0.01M sodium hydroxide) for 4-NBAcarbon on bppg. A plot of peak potential vs. pH for the peak corresponding to system I in FIG. 14 and both the oxidative and reductive peaks corresponding to system II in FIG. 2 is presented in FIG. 16B. The plots of peak potential vs. pH produced in each case a linear response with a corresponding R$^2$ value of not less than 0.9943. The gradient of such a plot for the oxidative and reductive peaks of system II yielded values of 60.4 mV/pH unit and 59.8 mV/pH unit respectively. This is close to the ideal theoretical gradient of 59.1 mV/pH unit at 298 K predicted by the Nernst equation.

A similar plot of peak potential vs. pH for the irreversible system I yielded a gradient of 42.5 mV/pH unit. This clearly deviates from the Nernstian behaviour predicted by the equation (1). This may be partly explained by the fact that the Nernst equation (1) is derived for systems exhibiting reversible kinetics, 1 whilst system I is clearly chemically and electrochemically irreversible. Furthermore similar results of a ca. 40 mV/pH unit shift were obtained by Wain et al. in their studies of microdroplets of 4-nitrophenol-nonyl-ether on a bppg electrode immersed in aqueous solutions of varying pH. They attributed this deviation from Nernstian behaviour to possible competition between H$^+$ and alkali metal cations such as K$^+$ and especially Li$^+$. The fact that system I rapidly vanishes after the first couple of scans makes these modified carbon materials of the invention ideally suited for use as "single-shot" pH sensors for use in media, such as effluent and sewerage, where recovery of the sensor is unlikely to be desirable.

Figure 17A:
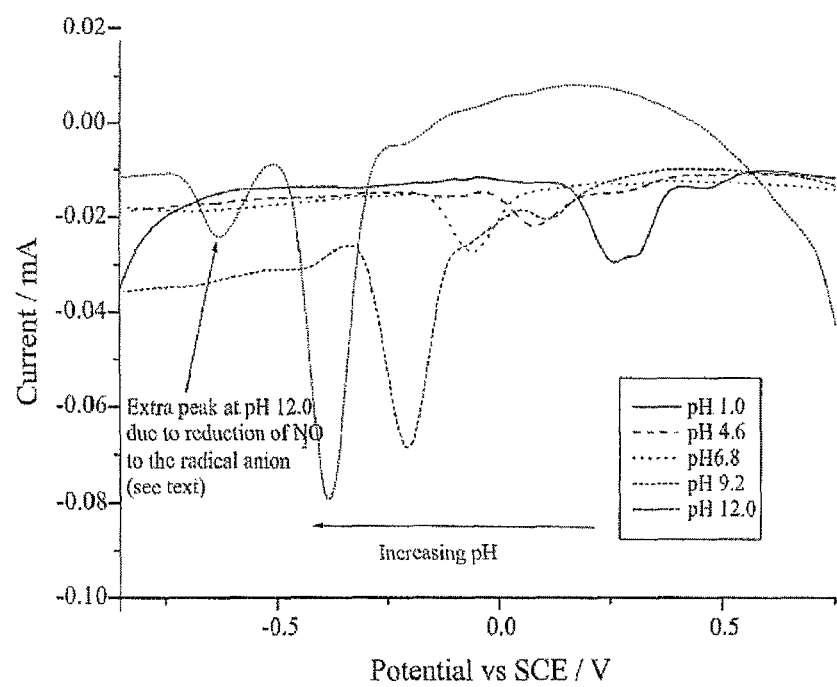
FIG. 17A shows overlaid square wave voltammograms (reductive sweep) of 4-NBA derivatised MWCNTs recorded in solutions of varying pH (pH 1.0, pH 4.6, pH 6.8, pH 9.2 and pH 12.0).
Figure 17B:
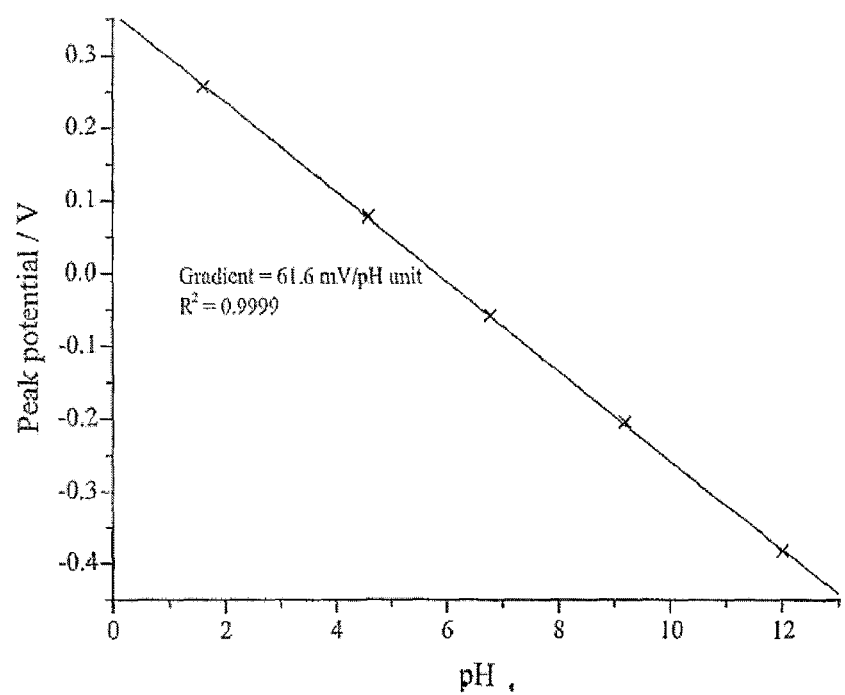
FIG. 17B shows the corresponding plot of peak potential vs. pH.

The reversible, Nernstian redox processes corresponding to the oxidation/reduction of the arylhydroxylamine/arylnitroso moieties of 4-NBA remain stable for many tens of scans. The variation of this redox couple with pH was investigated further using the technique of square wave voltammetry. Square wave voltammetry has significant advantages over conventional cyclic voltammetry, as it provides a means of carrying out a single sweep, producing a well-defined voltammetric peak as the arylhydroxylamine/arylnitroso couple has nearly reversible kinetic behaviour. FIG. 17A shows the corresponding overlaid reductive square wave voltammograms recorded at each pH studied for 4-NBAMWCNTs. It is worth noting that at pH 1.0 the oxidative wave is somewhat distorted due to the presence of an azoxy linkage affecting the redox chemistry. This causes some deviation from linearity in a plot of peak potential vs. pH at low pH values (FIG. 17B). Furthermore an extra peak is observed at pH 12.0 that was not observed in the cyclic voltammograms at this pH. The presence of this peak can be attributed to the formation of the radical anion of the nitro-group upon reduction which is relatively stable and electrochemically reversible at such alkaline pHs. Its presence is observed in square wave but not in cyclic voltammetry due to the high sensitivity of the technique. It is apparent from FIG. 17B that a plot of peak potential vs. pH taken from the square wave data produces a linear, Nernstian response (apart from the deviation at low pH), with gradients of 62.8 mV/pH unit and 59.2 mV/pH unit for the oxidative and reductive processes respectively and R$^2$ values greater than 0.9998. This again is in excellent agreement with theory (equation 1).

Example 8

Characterisation of 4-NBAcarbon and 4-NBAMWCNTs

The nature of the surface modification of the carbon used in the Examples above was then investigated to determine whether the compound of formula (I) (in this case 4-NBA) had indeed been intercalated and in particular to determine whether it had been partially intercalated. In terms of modification of carbon by a compound, there are three general possibilities: (i) physical adsorption (physisorption), (ii) chemical adsorption (chemisorption) and (iii) full or partial intercalation.

Example 8.1

Test for Physical Adsorption (Physisorption) of 4-NBA onto Graphite and MWCNTs The inventors investigated how the length of time the reaction mixture was stirred during the derivatisation procedure affected the amount of 4-NBA absorbed by the carbon material. In order to do this an aliquot of the reaction mixture, which contained graphite particles or MWCNTs suspended in a 10 mM solution of 4-NBA in acetonitrile, was removed, filtered, washed with dry acetonitrile and dried at 40 minute intervals until 160 minutes of stirring had elapsed. The samples were then abrasively immobilised onto a bppg electrode and cyclic voltammetry was carried out in pH 6.8 buffer. Five scans were recorded for each sample, and five samples were separately abrasively immobilised for each aliquot removed at a given time. From the five cyclic voltammograms recorded for each sample, the peak areas corresponding to the irreversible four-electron, four-proton reduction of the nitrogroup moiety at −0.6 V vs. SCE in FIG. 15A, and the reversible two-electron, two-proton arylhydroxylamine/arylnitroso couple at −0.1 V vs. SCE in FIG. 3A were measured. These peaks are labelled as system I and system II respectively in FIG. 14.

The peak area is the amount of charge passed during a redox process and can therefore be directly related to the number of moles of 4-NBA on the carbon surface using Faraday's Laws. This was repeated for each of the five samples taken at each time interval. Because the exact amount of material immobilised onto the electrode surface cannot be accurately controlled using abrasive immobilisation, the data from each of the five cyclic voltammograms recorded for each of the five samples (twenty-five cyclic voltammograms in total for each time period investigated) was averaged and plotted against time. The standard deviation was calculated as an error bar for each point showing the dispersion of data over the five abrasive immobilisations carried out for each time interval.

Figure 18:
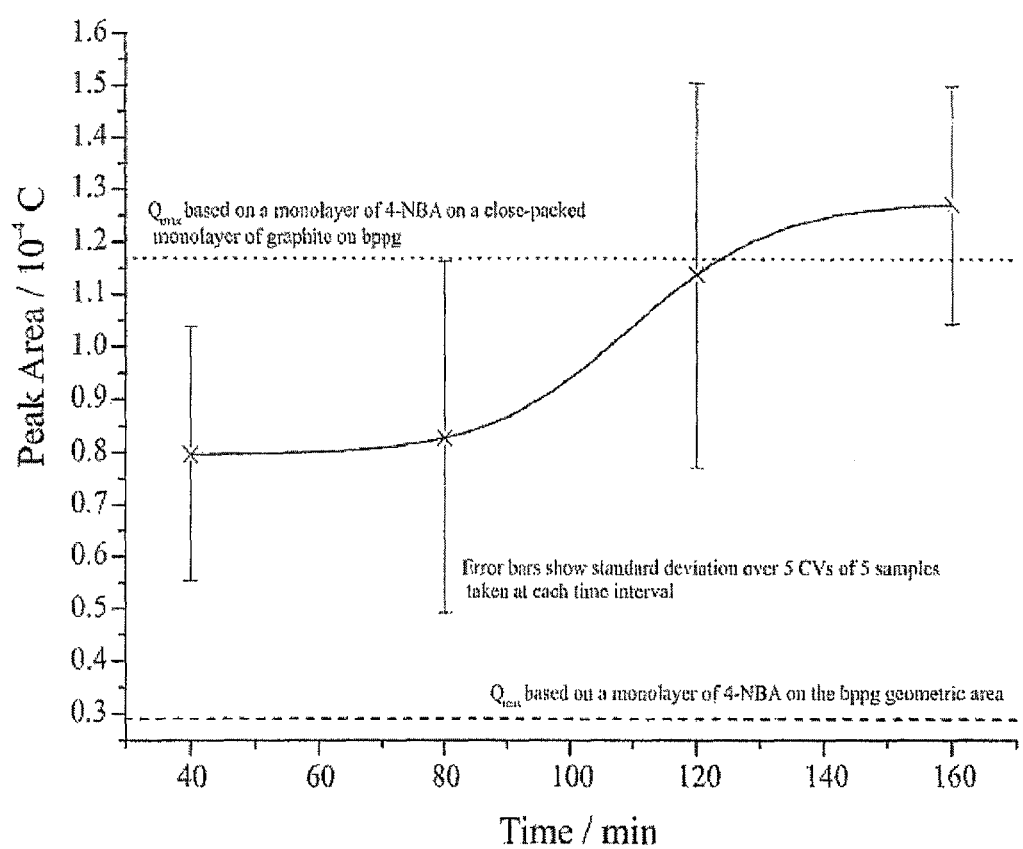
FIG. 18 is a plot of system I peak area vs. time for 4-NBAcarbon sampled at various times during derivatisation. Error bars show the standard deviation over 5 samples.

FIG. 18 shows a plot of peak area vs. time recorded for the irreversible reduction peak at −0.6 V vs. SCE of 4-NBA derivatised graphite. Also shown on this graph for comparison are the theoretical maximum charges passed for a monolayer of 4-NBA molecules covering the geometric area of the bppg electrode, and for a monolayer of 4-NBA coating the surface of the graphite particles (modelled as spheres) which themselves are close-packed as a monolayer on the geometric surface of the electrode. This model is a gross oversimplification as first the true surface area of a bppg electrode is always larger than its geometric area due to the surface not being perfectly smooth, and second the abrasive immobilisation of graphite particles onto the electrode surface is likely to produce multiple layers of particles which are not necessarily going to be close packed due to the uneven shape and size distributions of the particles. However such a calculation is useful in that it provides us with an indication of the degree of modification by the 4-NBA molecules.

FIG. 18 shows that at longer reaction times the amount of immobilised 4-NBA reaches a maximum value showing saturation. Analogous results were observed for both the oxidative and reductive peaks belonging to system II in FIG. 2, and in the case of MWCNT derivatisation. Whilst this experiment in itself does not provide evidence for intercalation it gives an interesting insight into the "filling-up" of the sites at which 4-NBA can modify the carbon surface. This effect would also be observed if physisorption led to only a monolayer formed on the surface. In fact it is important to note that the fact that the number of sites where 4-NBA can modify the MWCNTs or graphite powder is limited is consistent with any of the three hypothesis presented in this report, physical adsorption, chemical adsorption or intercalation of 4-NBA.

The derivatised carbon powders/MWCNTs are washed with a large quantity of dry acetonitrile during the derivatisation procedure, with the specific aim of removing any physisorbed material which is known to desorb when treated with non-aqueous solvents. It is therefore highly improbable that surface physisorption is the mechanism of modification in this case.

Further evidence against physisorption arises from the fact that we have carried out electrochemical experiments using cyclic voltammetry on 4-NBAcarbon and 4-NBAMWCNTs in acetonitrile solutions with 0.1M TBAP and 0.1M LiClO$_4$ as supporting electrolyte (see below). However, slow desorption kinetics of 4-NBA from the MWCNTs or graphite powder may explain the fact that voltammetry can be observed from 4-NBAcarbon and 4-NBAMWCNTs in acetonitrile. Therefore in order to verify that slow desorption kinetics were not responsible for our experimental observations described above, the following experiment was performed. In this experiment, 4-NBAcarbon was abrasively immobilised onto a bppg electrode. The electrode was then immersed into acetonitrile and stored for a period of one week. After this time the electrode was removed and placed in an aqueous solution and the cyclic voltammetry recorded. No significant deterioration in the aqueous voltammetric response, either in the magnitude of peak currents or peak potentials was observed.

Next cyclic voltammetry was conducted on immobilised 4-NBA in acetonitrile solutions containing either 0.1M TBAP or 0.1M LIClO$_4$ as supporting electrolyte. Upon sweeping in a reductive direction voltammetric peaks were observed with each electrolyte salt corresponding to the reduction of the attached nitro-group moiety. With 0.1M TBAP as supporting electrolyte a poorly resolved electrochemically reversible couple was observed at ca. −1.0 V vs. Ag. This can be attributed to the reversible one-electron reduction of the nitrogroup to the corresponding radical anion. When 0.1M LiClO$_4$ was used as supporting electrolyte an irreversible reduction wave was observed at ca. −0.8 V vs. Ag and a reversible system was formed on repetitive cycles at ca. −0.4 V vs. Ag.

Further cyclic voltammetric experiments were carried out using 4-NBAcarbon abrasively immobilised onto a bppg electrode in acetonitrile containing 0.1M TBAP as supporting electrolyte. The electrode was then removed from the non-aqueous solution and placed in an aqueous solution (pH 6.8). Again a stable voltammetric response was observed corresponding to the aqueous redox electrochemistry of 4-NBA. Next an electrode containing abrasively immobilised 4-NBAcarbon is placed directly into the aqueous electrolyte (pH 6.8) and the voltammetry recorded. A comparison of the resulting cyclic voltammograms for both cases (with and without conducting cyclic voltammetry in non-aqueous solution prior to conducting voltammetry in pH 6.8 buffer) revealed that the magnitude of the peak currents and the peak potentials observed in the voltammetry were almost identical.

If the 4-NBA was physically adsorbed onto the graphite surface one would expect it to have desorbed into the acetonitrile solution, and no response would be observed either in the non-aqueous acetonitrile solution or in the aqueous electrolyte solution.

It can therefore be concluded that physical adsorption is not the mechanism by which the carbon surface of graphite or MWCNTs is modified with 4-NBA.

Example 8.2

Test for Chemical Adsorption (Chemisorption) of 4-NBA onto Graphite and MWCNTs

In previous studies chemisorption of organic molecules onto carbon is achieved in two ways. The first is an "heterogeneous" method which uses the direct electrochemical reduction of diazonium salts or the electrochemical oxidation of amines. The second method is carried out "homogeneously" (the term "homogeneous" is used in this context to mean that both the modifier and the oxidant/reductant are in the solution phase) e.g. the reduction of aryldiazonium salts with hypophosphorous acid in the presence of graphite powder.

Barbier et al. have shown that 4-NBA can be "heterogeneously" chemically bound to the surface of a glassy carbon electrode by direct electrochemical oxidation. The mechanism of the amine bond formation to the electrode surface proceeds via the oxidation of the amine group to the corresponding radical cation, $ArNH_2^{+\bullet}$ which subsequently can react with the carbon surface to form a covalent C—N bond.

To test whether we had achieved the chemisorption of 4-NBA using a "homogeneous" method the following experiment was carried out: graphite powder and MWCNTs were derivatised with 4-NBA (10 mM in acetonitrile). Next the derivatisation procedure was repeated on fresh batches of graphite and MWCNTs with the exception that the acetonitrile was degassed with nitrogen for 20 minutes prior to use. The reaction mixture was kept under a blanket of nitrogen during the derivatisation procedure to prevent atmospheric oxygen diffusing into the solution. This prevented the possibility of aerial oxidation of 4-NBA to the radical cation by dissolved or atmospheric oxygen and subsequent reaction with the carbon material. Finally fresh batches of graphite and MWCNTs were derivatised as describe previously except that a strong oxidising agent, (tris(4-bromophenyl)aminium hexachloroantimonate (TBPAHCA, 25 mM in acetonitrile) was added to the reaction mixture. TBPAHCA was used to promote oxidation of the amine group to the corresponding radical cation and subsequent reaction with the carbon material.

The resulting 4-NBA derivatised graphite and MWCNTs from each of the three different preparations (using a strong oxidant, using acetonitrile which contained dissolved oxygen and using degassed acetonitrile) were separately immobilised onto a bppg electrode and their corresponding cyclic voltammograms recorded in pH 6.8 buffer and in acetonitrile (0.1M TBAP). In all three cases there was no observable difference in the voltammetric behaviour of the 4-NBAcarbon or 4-NBAMWCNTs in either aqueous or non-aqueous media. It can be inferred from this result that graphite and MWCNTs are derivatised by 4-NBA in exactly the same manner whether the derivatisation is carried out in degassed acetonitrile, acetonitrile containing dissolved oxygen or in the presence of a strong oxidising agent. This implies that 4-NBA modifies the carbon materials even when the formation of the corresponding radical cation of the amine group is unlikely to occur. Thus it can be concluded that chemical adsorption of 4-NBA via formation of the radical cation and subsequent attack of the carbon surface is not the likely mechanism of carbon modification.

One further possible mechanism by which the 4-NBA molecules could chemically attach themselves to the surface is by reacting with surface carboxylic acid groups, which are formed on the surface of synthetic graphite and MWCNTs during manufacture, to form the corresponding amides. This however is not plausible for two reasons. First, amides are susceptible to cleavage by hydrolysis at high and low pH, whilst we have demonstrated by using cyclic voltammetry and observing a stable voltammetric response over many repeat cycles that 4-NBA remains stable on the carbon surface at pH 1.0 and pH 12.0. Second, experiments have been carried out which demonstrate that significant amounts of 4-NBA have modified the carbon surface stirring in the reaction mixture for just 40 minutes. In order for amidification to take place on time scales shorter than several weeks it is customary to use a coupling agent such as dicyclohexylcarbodiimide (DCC) as a catalyst to facilitate nucleophilic attack by the amine onto the carboxylic acid and to assist in the departure of the $OH^-$ leaving group. In the present derivatisation procedure there is neither a coupling agent nor sufficient time for amidification to occur.

Example 8.3

Test for Full or Partial Intercalation of 4-NBA into Graphite and MWCNTs: Voltammetric Evidence Having established in the previous two sections of this Example that 4-NBA is unlikely to adsorb onto the surface of graphite powders or MWCNTs the inventors then considered the possibility of full or partial intercalation of 4-NBA at localised edge-plane-like defects on the carbon surface. First the electrochemical evidence in light of the extensive literature devoted to the subject of graphite intercalation compounds was studied.

The fact that voltammetry can be observed in non-aqueous solutions, even after soaking a 4-NBA modified electrode in acetonitrile for one week, and yet we have shown that 4-NBA is unlikely to have been physisorbed or chemisorbed onto the carbon surface, implies that there may be some partial intercalation of 4-NBA into the carbon material. This is likely to occur at edge plane or edge-plane-like defects on the surface of either graphite or MWCNTs. Further electrochemical evidence for this stems from the effect of the supporting electrolyte used in the acetonitrile solutions.

Figure 19:
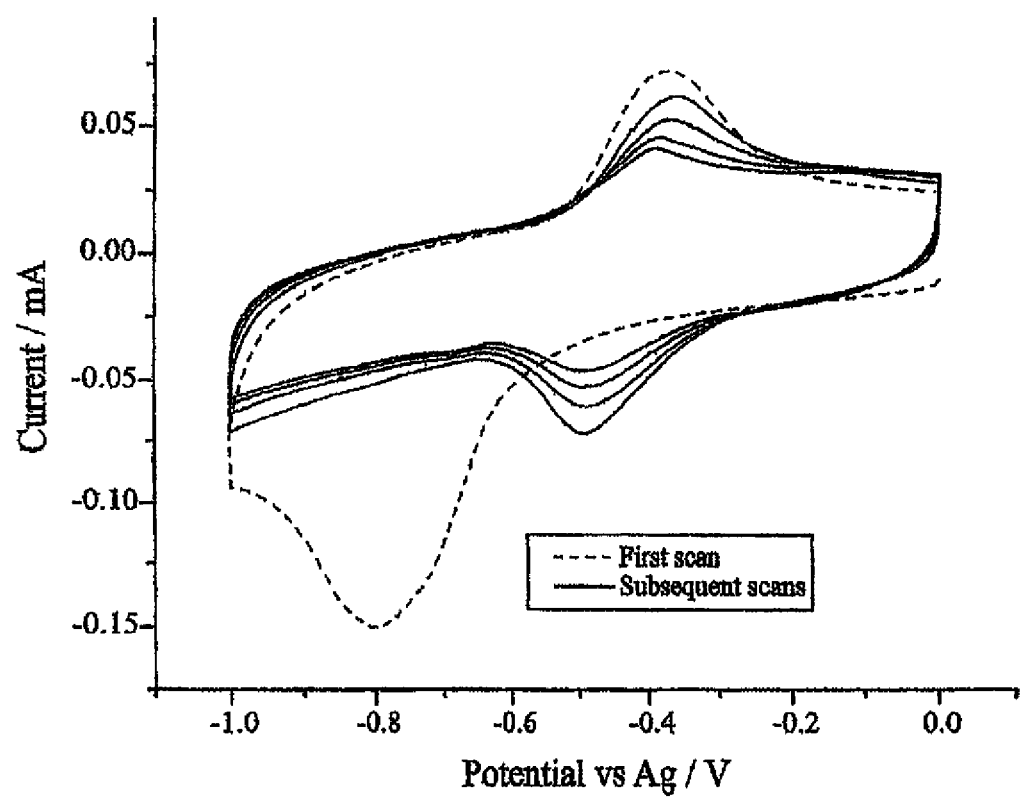
FIG. 19 shows five consecutive cyclic voltammograms of 4-NBA carbon in acetonitrile containing 0.1M LiClO$_4$.

If tetrabutylammonium perchlorate (TBAP) is used as the supporting electrolyte salt then any features in the cyclic voltammetry of 4-NBAcarbon or 4-NBAMWCNTs are small and poorly defined. However if the TBAP salt is replaced with lithium perchlorate then well-defined voltammetry is observed (FIG. 19). In particular it is worth noting that 4-NBA appears to remain bound to carbon in acetonitrile and does not leach into the solution phase, unless it is electrochemically reduced in the presence of $Li^+$ ions. When this occurs, the reduction, unlike in the case of TBAP, produces well defined peaks in the voltammetry. An investigation of the electrochemically reversible couple observed at circa −0.4 V vs. Ag reveals that upon repetitive cycles the corresponding peaks rapidly decrease and have completely disappeared by the tenth scan. If the experiment is repeated and the solution is agitated between recording the first and second scan by gently stirring the solution while the electrode is still immersed in it, the peaks associated with this redox process are no longer present in the second scan. This implies that the redox species, which is a reduced form of 4-NBA is in the solution phase and that stirring of the solution removes this species from the diffusion layer extending from the electrode surface into the bulk solution. Hence the signal corresponding to this species is no longer observed in the voltammetry after stirring.

Figure 20:
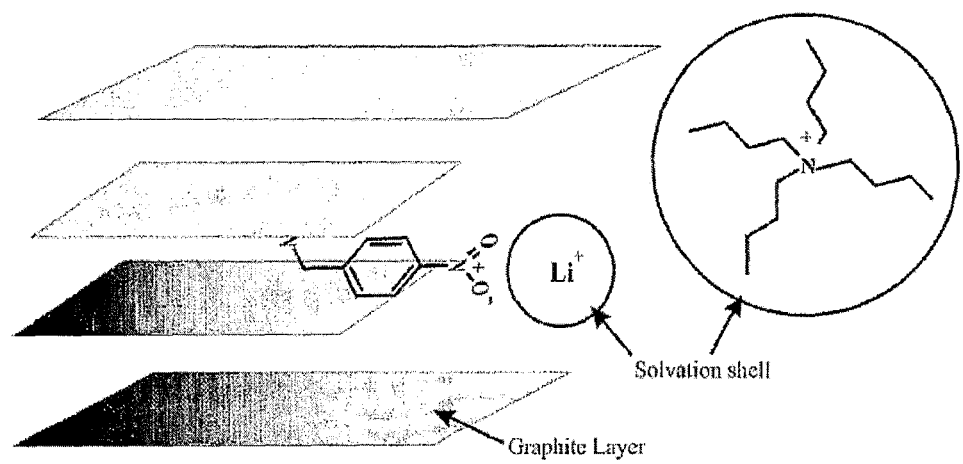
FIG. 20 depicts a schematic model of 4-NBA partially intercalated into graphite showing that solvated Li$^+$ cation may come into close contact with the 4-NBA molecule whereas the solvated NH$_4^+$ cation may not.
Figure 21:
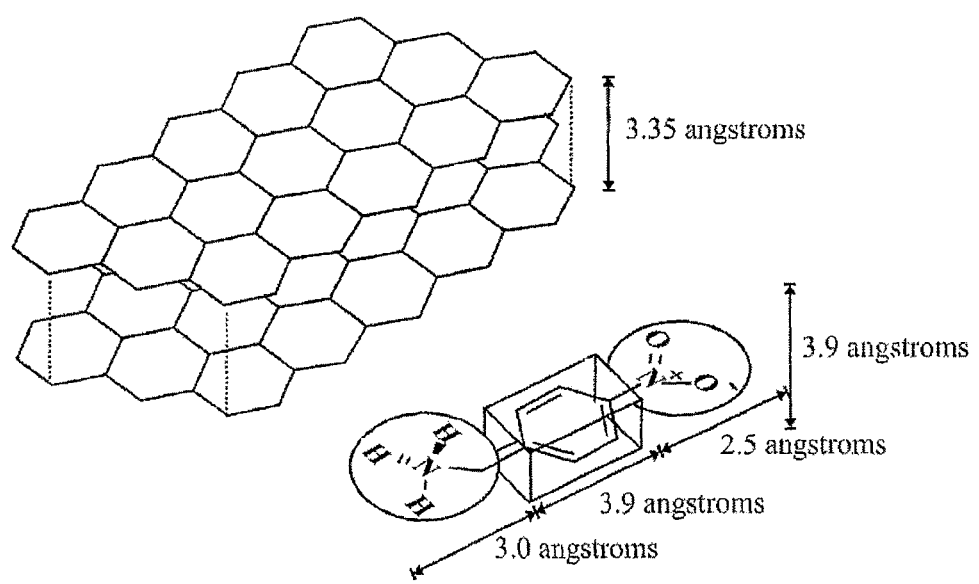
FIG. 21 shows a schematic model of the structure of graphite showing the approximate dimensions of a 4-NBA molecule and the graphite interlayer spacing for comparison.
Figure 22A:
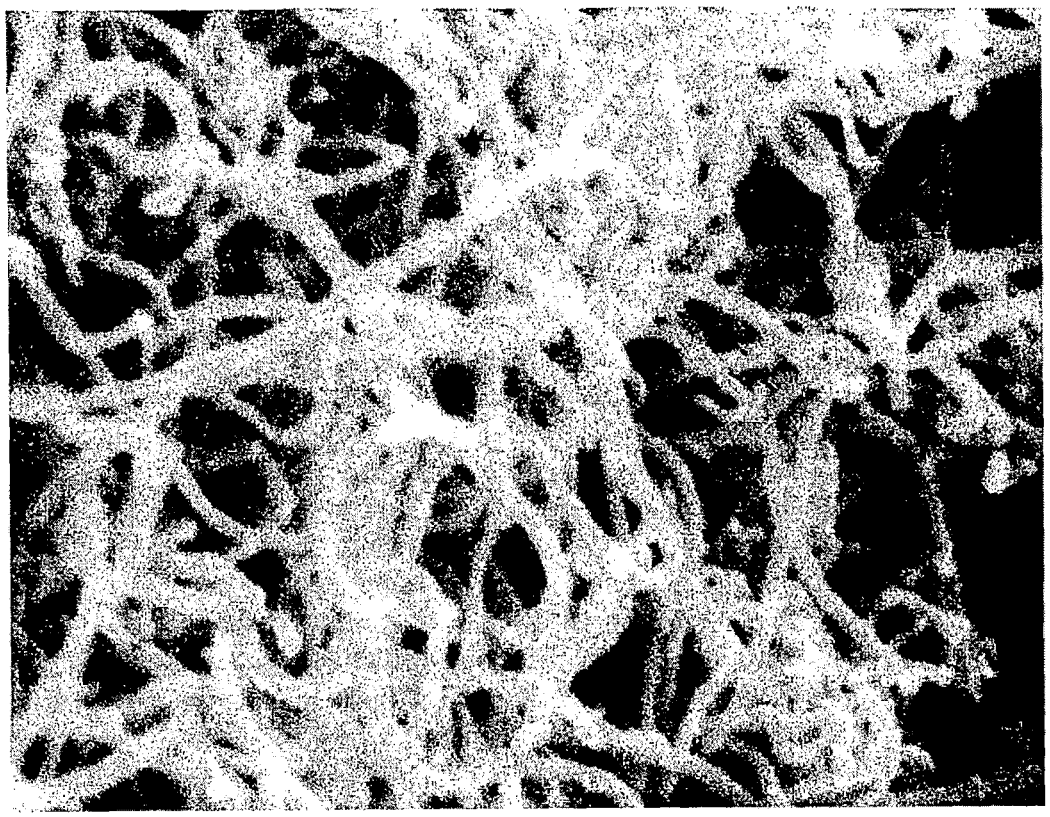
FIG. 22A shows a scanning electron microscopy image of MWCNTs modified with 4-NBA.
Figure 22B:
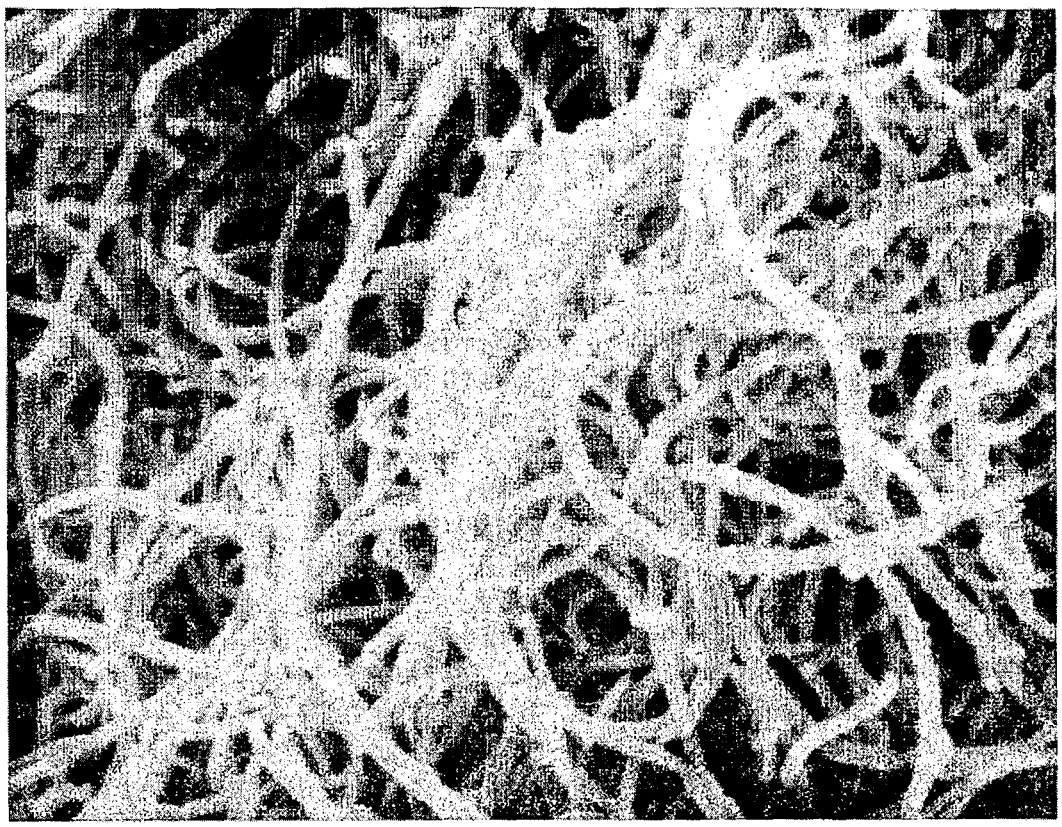
FIG. 22B shows a scanning electron microscopy image of unmodified "native" MWCNTs.

This behaviour can be explained if 4-NBA is partially intercalated at edge-plane defect sites along the surface of the carbon. The $NBu_4^+$ cation may be sterically hindered from approaching and complexing with the 4-NBA molecule as it lies inside the "pocket" formed by its partial intercalation into the disordered defect site (FIG. 20). Furthermore, the $NBu_4^+$ cation typically forms weakly bound ion-pair complexes. Hence the voltammetry of 4-NBAcarbon or 4-NBAM-WCNTs observed in acetonitrile containing 0.1M TBAP is poorly defined. Lithium cations on the other hand are much smaller in size and might therefore approach the 4-NBA even when it is partially intercalated. Upon reduction of the nitro-group the lithium ions, being highly polarizing, can form a complex with the reduced form of 4-NBA as either the radical anion or the arylnitroso/arylhydroxylamine. This complexation with $Li^+$ ions may cause the [Li 4-NBA]ion pair to leach out into solution. The formation of [Li 4-NBA]ion pairs is supported by the fact that the peak potential for the reduction in $0.1M\ LiClO_4$ is shifted in a positive direction compared to the peak potential in 0.1M TBAP. This positive shift in peak potential upon complexation with $Li^+$ has been well documented in the literature. Initially the [Li 4-NBA]ion pair remains in the diffusion layer adjacent to the electrode surface and so further redox voltammetry can be observed. However, upon solution agitation these ion pairs can be transported into bulk solution outside the diffusion layer and thus the corresponding voltammetry is no longer observed.

The small size of the solvated $Li^+$ ion is probably crucial to this process as even when the size of the quaternary ammonium cation is reduced by repeating the experiments with tetraethyl ammonium and tetramethyl ammonium perchlorates (TEAP and TMAP respectively) the voltammetry remains poorly-defined.

Full intercalation of 4-NBA deep within the inter-layer region in native (i.e. unmodified or treated) graphite or MWCNTs (which are analogous to "rolled-up" sheets of graphite) is highly unlikely. The inter-layer spacing ($I_c$) between ordered graphite sheets is 3.35 Å ($I_c$=3.44 Å in MWCNTs) which is too small to reasonably accommodate a 4-NBA molecule (FIG. 9). In order for full intercalation to occur the inter-layer spacing must increase. An extensive literature search reveals that: (1) there is no evidence of acetonitrile spontaneously intercalating into native graphite, thus there is no evidence for swelling of the graphite powder or MWCNTs by immersion into acetonitrile which would facilitate 4-NBA intercalation; (2) there is no evidence to suggest organic aromatic molecules similar in size to 4-NBA spontaneously intercalate into native graphite; (3) in the case of compounds of formula (I) where Y is an amine group, there is no direct evidence for amine intercalation (including ammonia and methylamine) into native graphite. However, all the above scenarios are possible when the inter-layer spacing ($I_c$) between graphite sheets is increased. This is readily achievable by intercalating alkali metal ions such as $Li^+$, $K^+$ into graphite to produce graphite intercalation compounds (GICs) e.g. $C_8Li$, $C_{24}Li$, or by using graphitic oxide, and graphitic acid. There is even evidence to suggest that SWCNTs can intercalate $K^+$ and $FeCl_3$ without rupturing the tube structure. Hence, the present derivatisation procedure does not include any of the above systems or criteria, and it can be concluded that full intercalation of 4-NBA into graphite does not occur.

Example 8.4

Test for Full or Partial Intercalation of 4-NBA into Graphite and MWCNTs: Evidence from Electron Microscopy and X-Ray Powder Diffraction Having inferred that intercalation may be responsible for the modification of graphite and MWCNT by 4-NBA using electrochemical means, evidence from other techniques is now presented.

Intercalation is only likely to occur at the edge-planes of graphite. These edge-plane surface sites are numerous on graphite powder particles and are the site of much of the chemical and electrochemical surface activity. Large regions of these edge-plane defects lead to areas of "disordered" graphite where the well-defined graphite crystal structure breaks down. Due to the relatively large dimensions of these disordered domains in graphite powder and the irregular morphology and size distribution of such particles (2-20 µm diameter) imaging of the surface before and after modification with 4-NBA using the techniques of electron microscopy does not give an insight into the nature and effect of the surface modification. However, MWCNTs have a relatively well defined size and morphology, and as such, any difference or disparity arising from modifying the surface with 4-NBA should become apparent.

Intercalation of 4-NBA into MWCNTs should cause some degree of expansion in the size of the spacing between adjacent graphite sheets or regions of graphitic material on the surface causing the tubes to "swell". In extreme cases these distortions could even cause the tubes to deform and/or rupture. In order to determine whether any swelling could be observed in the 4-NBA modified MWCNTs SEM was employed to image both unmodified "native" MWCNTs and 4-NBA modified MWCNTs after abrasive immobilisation onto the surface of a bppg electrode (FIG. 10A and FIG. 10B). Careful analysis of the diameter of the CNTs reveals that the average diameter of the native, unmodified MWCNTs is ca. 40 nm whilst the average diameter of 4-NBAMWCNTs is ca. 60 nm (based on a sample of fifty measurements each for native and 4-NBAMWCNTs, standard deviation in both cases was ca. 10 nm).

Numerous research groups have devoted considerable time and effort into modelling the processes that control CNT formation and growth. A common theoretical model used to describe CNT formation using chemical vapour deposition (CVD) as a method of synthesising CNTs is the step-flow growth kinetics model. In this model differences in the surface diffusion rates of carbon atoms along the growing nanotube wall lead to the formation of regions of multi-island nucleation in front the propagating "step" which can increase the number of surface defects and disordered "amorphous" regions. Furthermore, the intrinsic inequality of surface diffusional fluxes which feed the growth of different layers during MWCNT formation lead to "bamboo" structures. In these structures the graphite sheets are aligned at an angle to the axis of the nanotube and thus terminate at the surface of the tube as an edge-plane defect. As nearly every sheet must terminate at the surface, the number of edge-plane defects is large. One image used to describe these structures is to liken the bamboo MWCNT to a number of paper cups stacked one inside the other like so: <<<<<<< where "<" represents multiple nanotube walls.

The formation of "bamboo-MWCNTs" is temperature dependant. The MWCNTs used in this example were supplied by NanoLab Inc. They manufactured this sample using a CVD technique which operated at temperatures of ca. 900 K. Theoretical models predict that some multi-island nucleation and the subsequent formation of bamboo-like regions along the MWCNTs is likely to occur in this temperature region.

It is postulated that it is the presence of these bamboo-like regions along the MWCNTs that is responsible for the large uptake of 4-NBA and the resulting large currents passed during the voltammetric experiments conducted on them.

In order to provide us with a further insight into the morphology of the MWCNTs, HRTEM imaging was carried out.

Figure 23A:
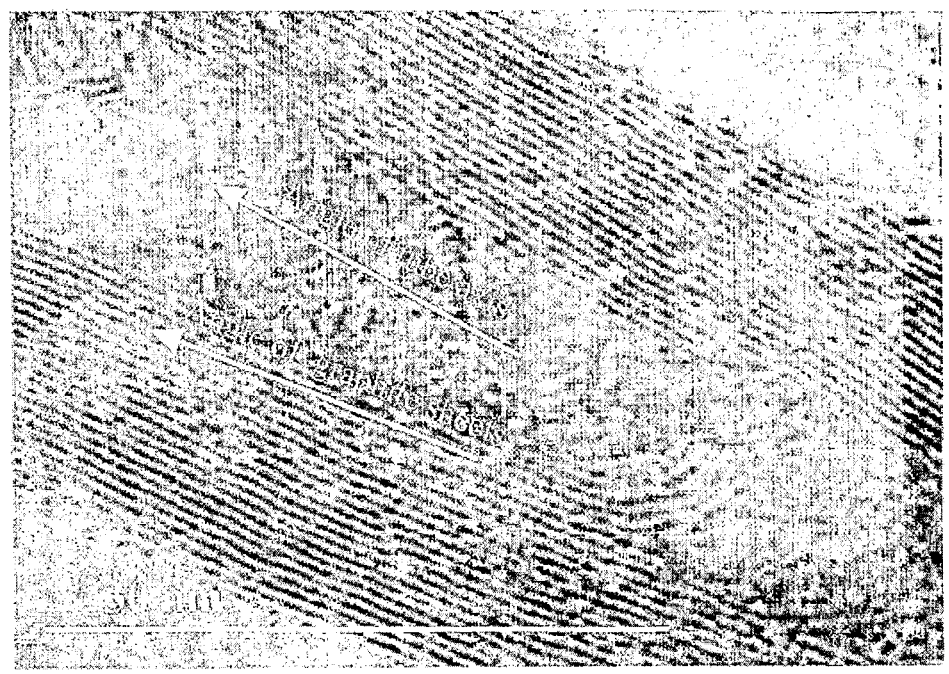
FIG. 23A shows a high resolution transmission electron microscopy image of a "bamboo-like" region of a MWCNT.
Figure 23B:
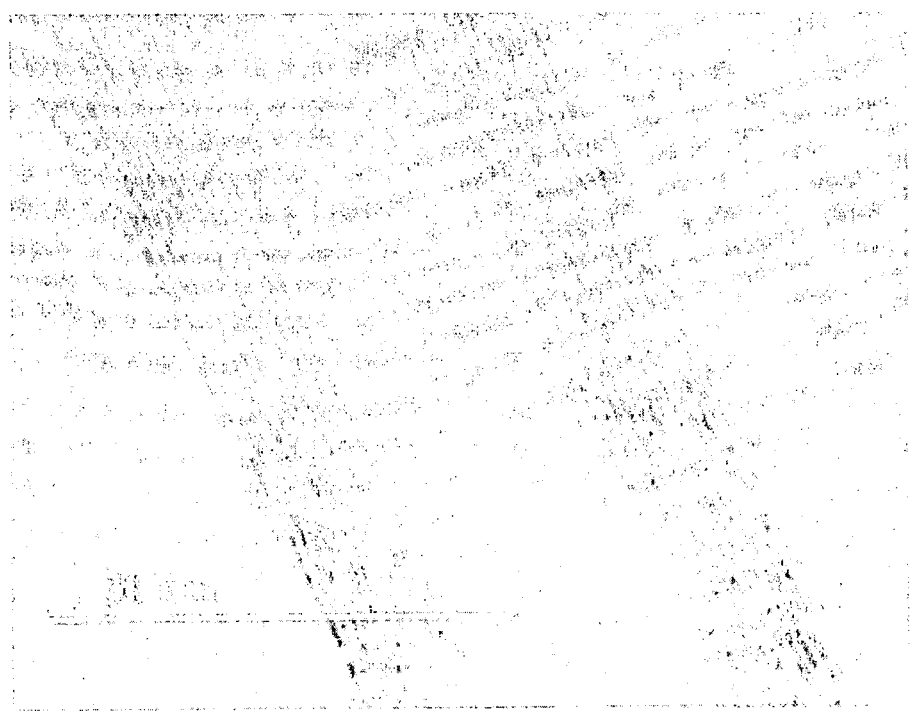
FIG. 23B shows a high resolution transmission electron microscopy image of a "hollow tube" region of a MWCNT.

FIGS. 23A and 23B show the HRTEM images of a sample of MWCNTs. These images indicate that both "bamboo-like" structures (see below) and hollow-tube structures occupy the length of a MWCNT.

The discovery of "bamboo-like" regions along the MWCNTs provides a possible explanation for the relatively large (milli-Ampere) currents passed during reduction/oxidation of 4-NBAcarbon and especially 4-NBAMWCNTs. These large currents imply that the coverage of 4-NBA on the graphite particles and MWCNTs is high. If 4-NBA is indeed partially intercalating into edge-plane defects on the MWCNTs then these defect sites must be so numerous that they can not simply be located at the open ends of the nanotubes, but along their surfaces too.

Next X-ray powder diffraction (XPD) was used to examine the effect of modifying graphite powder and MWCNTs with 4-NBA. The fundamental equation used to analyse X-ray diffraction data is given by Bragg's law, equation (2):

$$n\lambda = 2nd \sin\theta \quad (2)$$

where n is an integer representing the order of reflection from a set of planes, $\lambda$ is the wavelength of X-ray radiation/Å, d is the inter-plane spacing/Å, and $\theta$ is the angle of incidence at which the X-ray radiation falls on the sample. Any increase in the inter-layer spacing due to intercalation of 4-NBA into the lattice increases the value of d and thus can be observed by comparing the diffractogram of the modified sample with the diffractogram of the unmodified sample.

The X-ray powder diffractograms of 4-NBA carbon and unmodified graphite powder were recorded. Comparison of the diffractograms showed no qualitative or quantitative differences, either in the position of the peak or in the peak width and shape. Both samples produced a value for the inter-layer spacing of 3.37±0.01 Å which is in good agreement with literature values of 3.35±0.05 Å. This result excludes the possibility of full intercalation of 4-NBA into the graphite lattice. However this does not exclude the possibility of partial intercalation of 4-NBA at the disordered sites containing edge plane steps and defects. This is because XPD can only be used to interrogate highly ordered regions possessing a well defined crystal structure from which to obtain reflected X-rays at well defined values of $\theta$. Any disordered regions simply scatter the X-rays at random $\theta$ values without constructively interfering and hence these signals are lost as noise. Due to the much more ordered morphology of MWCNTs compared to graphite powder particles a comparison of 4-NBAMWCNTs and native MWCNTs using XPD is much more instructive as to the nature of the surface modification by 4-NBA.

Figure 24:
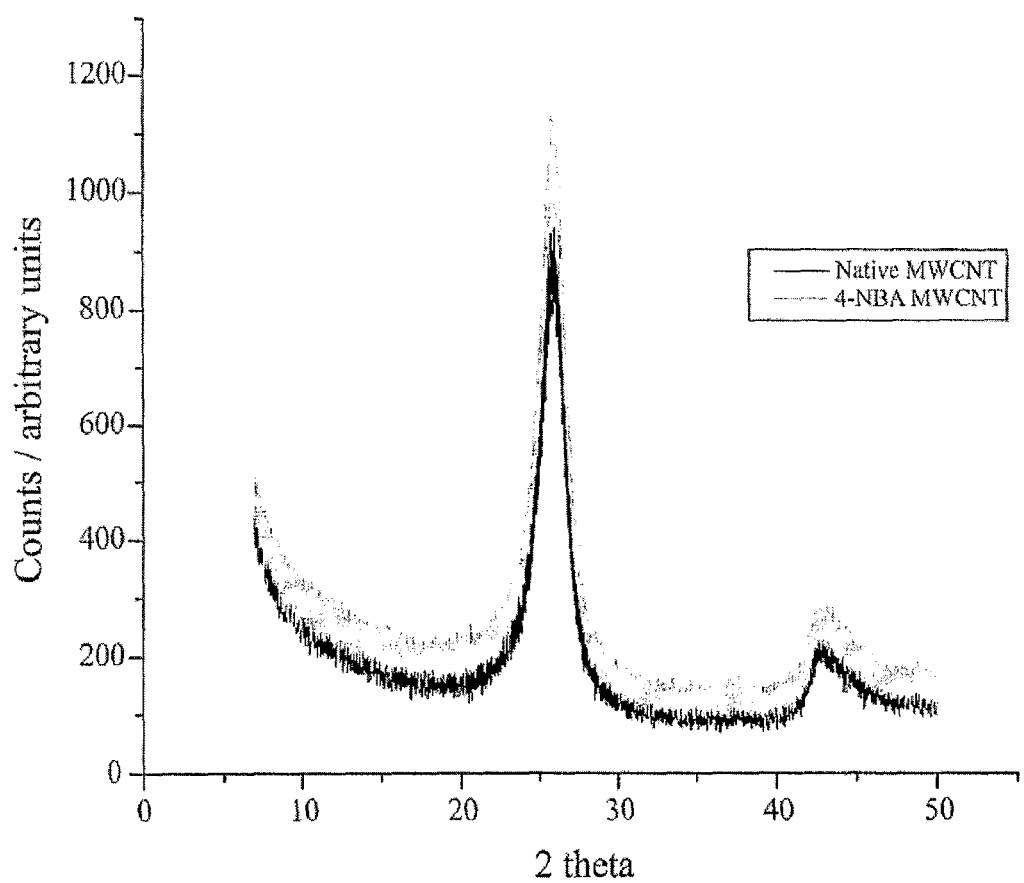
FIG. 24 shows X-ray powder diffractograms comparing unmodified "native" MWCNTs with 4-NBA modified MWCNTs.

To this purpose, X-ray powder diffractograms of 4-NBAMWCNTs and "native" unmodified MWCNTs were recorded for comparison (FIG. 24). The first point to mention is that the peak position for both the modified and unmodified MWCNTs is identical within experimental error and corresponds to an inter-layer separation of 3.47±0.04 Å which is again consistent with the literature value of 3.44±0.04 Å. The second point to note is in both cases the peaks are broadened and are unsymmetrical with a "tail" on the left hand edge of each peak. This is effect is due to variations in the inter-layer spacings leading to a certain degree of disorder in the crystal structure of the nanotubes. What is important to note is that the 4-NBAMWCNT peak is considerably broader than the native MWCNT peak. Analysis of the normalised peaks reveals that the full-height-half-width of the native MWCNT peak is 0.9446, whilst the 4-NBAMWCNTs full-height-half-width value has increased by nearly forty percent to 1.3855. This shows that there has been considerable disruption and an increase in the disorder of the MWCNT structure which may provide supporting evidence for partial intercalation of 4-NBA molecules at the edge-plane surface defects. The increase in disordering between the graphite sheets can be measured quantitatively using the Scherrer equation (3) which relates the half-height-full-peak-width to the average number of planes present in the ordered part of the crystal from which the X-ray reflections occur:

$$t = \frac{0.9\lambda}{\beta\cos\theta} \quad (3)$$

and $$t = md \quad (4)$$

where $\lambda$ and $\theta$ are defined as per equation (2) above, $\beta$ is the full-height-half-peak width, and t is the thickness of the crystalline region. Hence if the interlayer spacing (d) is known then the number of layers (m, graphite sheets in this case) in the crystalline, ordered region can be calculated from (4). Table 1 lists the data obtained from the XPD of 4-NBAMWCNTs and native MWCNTs for comparison. The value of m=9 ordered layers of graphite sheets for native MWCNTs is in agreement with HRTEM studies of the MWCNTs which found an average of 9 concentric tube walls present. This value has decreased on modifying the CNTs with 4-NBA to m=6 which is not an unreasonable value as it is likely that edge plane defects could expose up to the first three graphite layers.

TABLE 1

A comparison of the experimentally determined X-ray diffraction data for unmodified native MWCNTs and 4-NBA modified CNTs:

| | Inter-layer spacing/Å | Full-height-half-width/degrees | m-value, the number of adjacent ordered layers in the crystalline regions |
|---|---|---|---|
| Native MWCNT | 3.47 | 0.9446 | 9 |
| 4-NBAMWCNT | 3.47 | 1.3855 | 6 |

DETAILED DESCRIPTION OF THE THIRD PREFERRED ASPECT OF THE INVENTION

Figure 25:
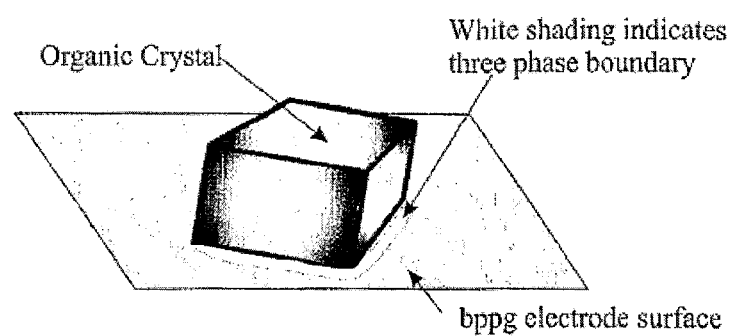
FIG. 25 is a schematic diagram showing the regions where the formation of a three-phase boundary may occur when a redox active material such as an organic crystal is immobilised on the surface of an electrode.

The solid state electrochemistry of a pure organic solid abrasively immobilised onto the surface of an electrode and which is in contact with an electrolyte solution must take place at the three phase boundary between the electrode surface|organic solid|solution interface. Concomitant ion insertion from the solution phase into the crystal to maintain charge neutrality upon oxidation/reduction must occur. FIG. 25 schematically depicts, with the white shading, this three-phase boundary at which transfer of electrons can occur.

However, since electron transfer can only occur at this three-phase boundary, the electroactive surface area of each individual crystal is restricted to a very small area which is in contact with both the electrode surface and the solution.

Figure 26:
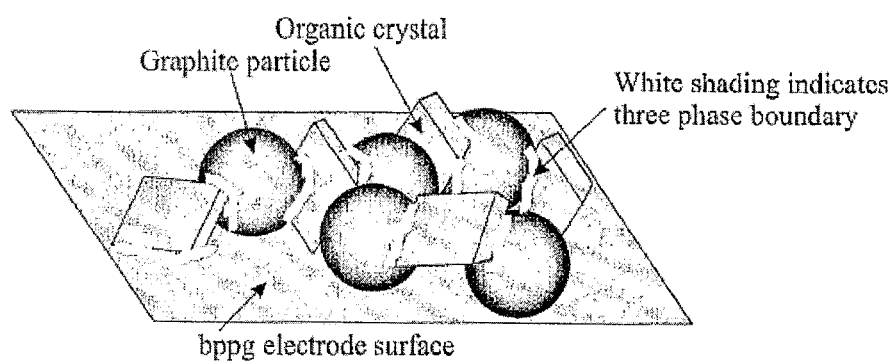
FIG. 26 is a schematic diagram showing the regions where the formation of a three-phase boundary may occur when a redox active material such as an organic crystal is mixed with carbon particles and immobilised on the surface of an electrode.
Figure 27:
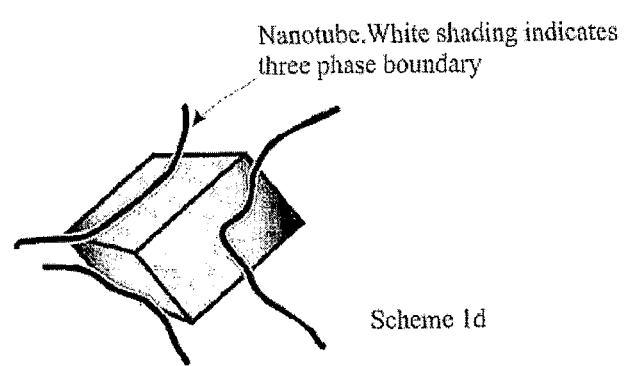
FIG. 27 is a schematic diagram showing the regions where the formation of a three-phase boundary may occur when a redox active material such as an organic crystal is mixed with carbon nanotubes and immobilised on the surface of an electrode. For clarity, the electrode surface is not shown.

Accordingly, another approach has been adopted which involves abrasively immobilising a physical mixture of the organic solid and graphite powder onto the surface of a bppg electrode, as shown in FIG. 26.

The electroactive surface area of the electrode shown in FIG. 26 is greater than that shown in FIG. 25. This is because not only can an electrode surface|organic solid|solution three phase boundary be formed, but where the carbon particles are in contact with the organic solid crystals an additional carbon particle|organic solid|solution three phase boundary is formed, thus allowing increased charge transfer. However, while electroactivity is improved using this method, the degree of contact between the graphite particles and the organic crystals is restricted by the size of the graphite particles.

The third preferred aspect of the present invention is concerned with the use of agglomerates comprising carbon nanotubes dispersed in a binder, wherein the binder is a redox-active material. The carbon nanotubes are preferably multi-walled carbon nanotubes (MWCNTs).

Electrodes made from the agglomerates comprise carbon nanotubes and a redox active material disposed on a substrate. The carbon nanotubes and redox active material need not be mixed in the form of an agglomerate. Instead they may simply be abrasively immobilised on the surface of the substrate. However, it is preferred that the carbon nanotubes and redox active material are disposed on the electrode in the form of an agglomerate, as described above in the first embodiment of the invention. Furthermore, it is again preferred that the carbon nanotubes are in the form of MWCNTs.

The electroactivity of these electrodes is greater than prior art electrodes. As a result, a smaller amount of material is required to achieve the same response and hence the electrodes themselves can be reduced in size, allowing for miniaturisation of the electrochemical sensors in which they are employed.

A method for preparing an agglomerate for use in electrochemical sensors comprises dispersing multi-walled carbon nanotubes in a binder, wherein the binder is a redox active material. This agglomerate can then be used in a method for preparing an electrode, which method comprises providing a substrate and applying carbon nanotubes and a redox active material to the surface of the substrate.

The agglomerates and electrodes can be used in electrochemical sensors. Such sensors can be used to monitor a number of different species, such as pH, carbon monoxide, hydrogen sulphide, oxygen, carbon dioxide, metal ions etc. The sensors are particularly useful in the measurement of pH, a measurement that is important in a number of fields, such as environmental, chemical, waste water, industrial and effluent.

By preparing electrodes having carbon nanotubes and redox active materials applied to a substrate, electroactivity is significantly improved because greater contact with the surface of the redox active material is achieved. In effect, the nanotubes act as "molecular wires" forming numerous three phase boundaries between the nanotube|redox active material|solution. When an agglomerate of nanotubes and redox active material is prepared even greater electroactivity is achieved. In this case the nanotubes are cemented together in bundles by the redox material so that they not only run along the surface, but also into and through the agglomerate. At every point of contact between the organic solid, nanotube and the solution, a three-phase boundary is formed. This results in a much larger electroactive surface area compared to the prior art.

Thus, an advantage of the present invention is that the electroactive area is increased, meaning that a smaller amount of material is required in order to achieve the same effect. As a result, the electrodes, as well as the sensors in which these electrodes are employed, may be reduced in size. Miniaturisation of sensors increases the number of applications for which they can be applied. For example, they could be used in biomedical applications where it may be necessary to introduce them into the patient's body. Alternatively they could be used for other applications where sensing apparatus must be used in confined spaces. Miniaturisation also allows for greater portability of the sensors.

The relative proportions of the nanotubes and redox active material used in the invention can be varied by the person skilled in the art. When a mechanical mixture of nanotubes and redox active material is immobilised on a substrate the ratio of these components is preferably 10:1 to 1:10 by mass, more preferably 5:1 to 1:5, more preferably 1:2 to 2:1. In the case where the components are present on the substrate in the form of an agglomerate, the relative proportions may vary significantly. In principle there is no lower limit to the amount of carbon nanotubes present.

The individual components and aspects of the third aspect of the invention will now be described in more detail.

Carbon Nanotubes

Carbon nanotubes (CNTs, also referred to herein as nanotubes) have been known for a number of years, having been discovered in 1991 (see S. Iijima, Nature, 1991, 56, 354). One field that has seen a large expansion in the study and use of nanotubes is electrochemistry. Carbon nanotubes are particularly useful in this field due to their noted mechanical strength, structure and good electrical conductivity. These properties have been used in electroanalytical applications ranging from catalytic detection and analysis of biological molecules such as dopamine, cytochrome c and carbohydrates, to the sensing of analytes such as hydrogen peroxide, hydrazine and TNT.

Structurally, nanotubes approximate to "rolled up" sheets of graphite and as such are relatively hydrophobic in nature. There are two main configurations of these "rolled up" sheets: single-walled carbon nanotubes and multi-walled carbon nanotubes (MWCNTs). In the present invention either configuration may be used.

Suitable nanotubes include those purchased from Nanolab Inc. (Brighton, Mass., USA). The physical properties of the nanotubes can be optimised by the person skilled in the art, although exemplary nanotubes have a diameter of from 1 to 50 nm, preferably from 5 to 30 nm, and a length of from 1 to 50 nm, preferably from 5 to 30 nm. Preferably the carbon nanotubes have a relatively high purity, preferably from 80 to 100%, more preferably from 90 to 100%, most preferably from 95 to 100%.

Redox Active Material

The redox active material may be any organic material capable of undergoing electron loss and gain. Preferably the redox active material is a solid phase material. When immobilised onto a substrate, e.g. glassy carbon or a basal plane pyrolytic graphite (bppg) electrode, they undergo concomitant proton and electron loss/gain on oxidation/reduction.

In order to be used in electrochemical sensors, at least a part of the redox active material will need to be sensitive to the species which is to be detected or measured. It is preferred that the electrodes be useful in the manufacture of pH meters, and accordingly it is preferred that the peak potential of the redox active materials depends on the local proton concentration.

The voltammetry of such compounds sensitive to pH, when immobilised as molecular solids onto the surface of an electrode, has been found to exhibit Nernstian behaviour which can be described according to the following Nernst equation:

$$E_p = E_f^0 - \frac{2.3\ RTm}{nF}\text{pH}$$

where $E_p/V$ is the peak potential, $E_f^0/V$ is the formal potential of the redox couple, $R/J\,K^{-1}$ is the universal gas constant, T/K is the temperature and m and n are the number of protons and electrons involved in the redox process respectively. In the materials tested in the Examples which follow, m and n are often equal to 2.

Accordingly, by studying the voltammetric response of these compounds, for example using cyclic voltammetry or square-wave voltammetry, a linear response of peak potential to pH would be expected.

The redox active material can comprise more than one compound. For example, the material may comprise a chemically sensitive redox material and a chemically insensitive redox material. In this embodiment, the chemically insensitive redox material serves as a reference material. By measuring the potential difference between the current peaks for the chemically sensitive and chemically insensitive redox materials, the concentration of the species to be measured can be determined.

Alternatively, the redox active material may comprise more than one chemically sensitive material which is sensitive to the same species. By measuring the potential difference between the current peaks for the chemically sensitive materials compared to that of the reference electrode, a more accurate concentration of the species to be measured can be obtained.

The redox active materials used in the example are preferably hydrophobic, have a low solubility in water. This allows them, when an agglomerate is being manufactured, to mix with the carbon nanotubes in solution and results in the agglomerate precipitating out of solution when an excess of aqueous solution is added.

Suitable redox active materials include quinones and anthracenes, for example 9,10-anthracene, 9-nitroanthracene, phenanthraquinone (PAQ) and 1,2-napthaquinone (NQ). Other materials that can be used include azobenzene, diphenylamine, methylene blue, 3-nitrofluoranthene, 6-nitrochrysene and thionin.

The Agglomerate

The agglomerate of the invention comprises nanotubes and a binder, wherein the binder is a redox active material. The nature of the nanotubes and redox active material may be as described above.

The agglomerate is made by dispersing the nanotubes in a binder. The preferred method comprises combining the nanotubes and binder material in a solvent, and then precipitating the agglomerate out of the solution. In particular, the method may comprise:
(1) combining the carbon nanotubes and the binder in a solvent;
(2) adding an excess of aqueous solution in order to cause precipitation of the agglomerate out of the solvent; and
(3) recovering the agglomerate.

Preferably the solvent is a hydrophobic solvent, comprising small organic molecules. The solvent should be chosen such that the redox active compound and the carbon nanotubes are both soluble within it. Suitable solvents include all common organic solvents such as acetone, acetonitrile and dimethyl formamide.

The agglomerate preferably comprises the carbon nanotubes and redox active material only, with no other materials present. However, the agglomerate may contain some impurities such as residual solvent, left as a result of a process by which the agglomerate is be produced. Preferably these impurities comprise less than 1 wt % of the agglomerate, more preferably less then 0.5 wt %. The precise level of impurities which is acceptable in the agglomerate will depend upon how the impurities affect the voltammetry of the agglomerate.

The size of the agglomerates depends upon the nature and proportions of the components used in their preparation and the conditions of the process by which they are prepared. However, exemplary agglomerates may be approximately 10 μm in diameter and consist of bundles of nanotubes running into and throughout an amorphous molecular solid which binds the agglomerate together.

The Substrate

The substrate onto which are applied the carbon nanotubes and redox active material may be any substrate conventionally used in the manufacture of electrodes. For example, the substrate may be a basal plane pyrolytic graphite (bppg) electrode or glassy carbon, metal electrodes such as gold or platinum, or optically transparent electrodes such as those comprising ITO. The substrate preferably has good electrical contact with the carbon nanotubes, and also has a surface such that good coverage with the carbon nanotubes and redox active material can be achieved.

The Sensor

The structure of the sensor will depend upon its final application, and hence depends upon the substance which it is to measure and the environment in which measurement will take place. Known sensor structures may be employed in conjunction with the agglomerates and electrodes described herein.

Exemplary sensors may have a two or three terminal arrangement. Thus, they may comprise a working electrode of the invention and a combined counter and reference electrode, or a working electrode, counter electrode and a reference electrode. The reference electrode and counter electrode can be any conventional electrodes known in the art.

The materials used in the sensor depend upon which species the sensor is intended to measure and the environment in which the sensor is to be used. In order to modify the sensor to be sensitive to a different species it is simply required for the skilled person to substitute the redox active material with a different redox active material sensitive to the species which is to be measured.

Examples of the Third Preferred Aspect of the Invention

Example 9

Formation of Nanotube Agglomerates and their Abrasive Immobilisation onto the Surface of Basal Plane Pyrolytic Graphite Reagents and Equipment All reagents were obtained from Aldrich (Gillingham, UK) with the exception of potassium chloride which was obtained from Riedel de Haën (Seelze, Germany) and were of the highest grade available and used without further purification. All aqueous solutions were prepared using deionised water from an Elgastat (Elga, UK) UHQ grade water system with a resistivity of not less than 18.2 MΩ cm. All cyclic voltammetric measurements were made after degassing the solution with pure $N_2$ gas (BOC Gases, Guildford, Surrey, UK) for 30 minutes and unless otherwise stated were recorded at a temperature of 20±2° C.

Multi-walled carbon nanotubes (MWCNTs) with purity ~95% were purchased from Nanolab Inc. (Brighton, Mass., USA) and were used without further purification.

Solutions of known pH in the range pH 1-12 were made up in de-ionised water as follows: pH 1, 0.1M HCl; pH 4.6, 0.1M acetic acid+0.1M sodium acetate; pH 6.8, 0.025 M Na$_2$HPO$_4$+0.025 M KH$_2$PO$_4$; pH 9.2, 0.05 M disodium tetraborate; pH 12 0.01M sodium hydroxide. These solutions contained in addition 0.1M KCl as additional supporting electrolyte. pH measurements were performed using a Jenway 3030 pH meter.

Electrochemical measurements were recorded using a µAutolab computer controlled potentiostat (Ecochemie, Netherlands) with a standard three-electrode configuration. All experiments were carried out using a double-walled glass cell of volume 25 cm$^3$ thermostatted to the desired temperature (20-70° C.) through circulation of water from a heated bath. A basal plane pyrolytic graphite electrode (bppg, 0.20 cm$^2$, Le Carbone Ltd., Sussex, UK) acted as the working electrode (see below). A platinum coil acted as the counter electrode and a saturated calomel electrode as the reference electrode (SCE, Radiometer, Copenhagen) completed the cell assembly.

Unless stated otherwise cyclic voltammograms were recorded using the following parameters: step potential 2 mV, scan rate 50 mV s$^{-1}$. Square wave voltammetric parameters were as follows: frequency 12.5 Hz, step potential 2 mV and amplitude 25 mV. Scanning electron microscopy (SEM) was conducted using a Jeol 6500F instrument.

It is worth noting that the toxicology of both 9,10-phenanthraquinone and 1,2 napthaquinone has not yet been fully investigated. Both compounds may be harmful, or irritant by skin contact or inhalation and are suspected carcinogens.

Formation of Nanotube Agglomerates and their Abrasive Immobilisation onto the Surface of Basal Plane Pyrolytic Graphite Agglomeration of MWCNTs with either 9,10-phenanthraquinone (PAQ) or 1,2-napthaquinone (NQ) was achieved by mixing 50 mg MWCNTs with 10 cm$^3$ of a 10 mM solution of either PAQ or NQ in acetone and slowly adding 25 cm$^3$ of 0.1M HCl+0.1M KCl aqueous solution. The reaction mixture was stirred continuously for 2 hours in a beaker and then filtered by suction after which it was washed with distilled water to remove the acid and salt. It was then air-dried by placing inside a fume hood for 12 hours and finally stored in an airtight container until required.

The agglomerates of nanotubes and either PAQ or NQ were then abrasively immobilised onto the surface of the bppg electrode prior to characterisation. This was done by initially polishing the electrode on glass polishing paper (H00/240), after which it was polished on silicon carbide paper (P1000C) for smoothness. The nanotube-PAQ or nanotube-NQ agglomerates were then mechanically immobilised onto the bppg electrode by gently rubbing the electrode surface on a fine filter paper (Whatman) containing the agglomerates.

Example 10

Characterisation of the Nanotube Agglomerates

First the formation of the agglomerates was verified using SEM and CV and then the immobilisation of the agglomerates onto the surface of the bppg was confirmed voltammetrically using CV.

Determination of the Degree of Agglomeration

Figure 29:
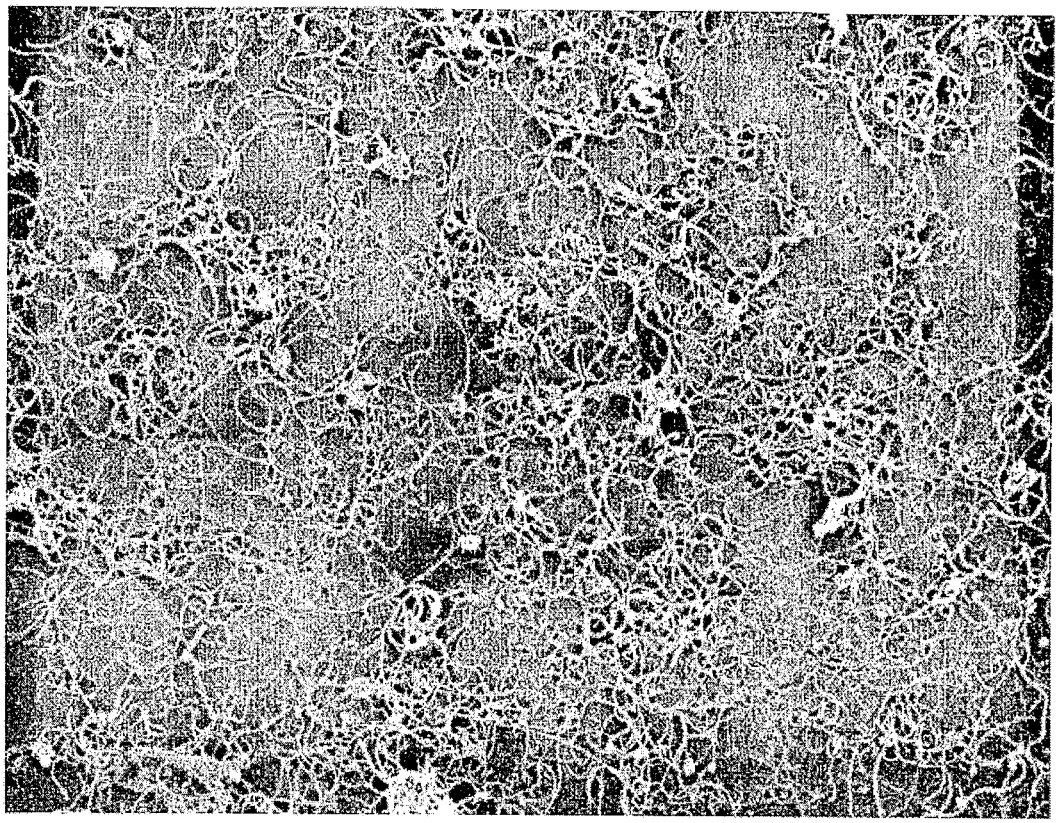
FIG. 29 is an SEM image of abrasively immobilised nanotubes dispersed on the surface of a bppg electrode.
Figure 30:
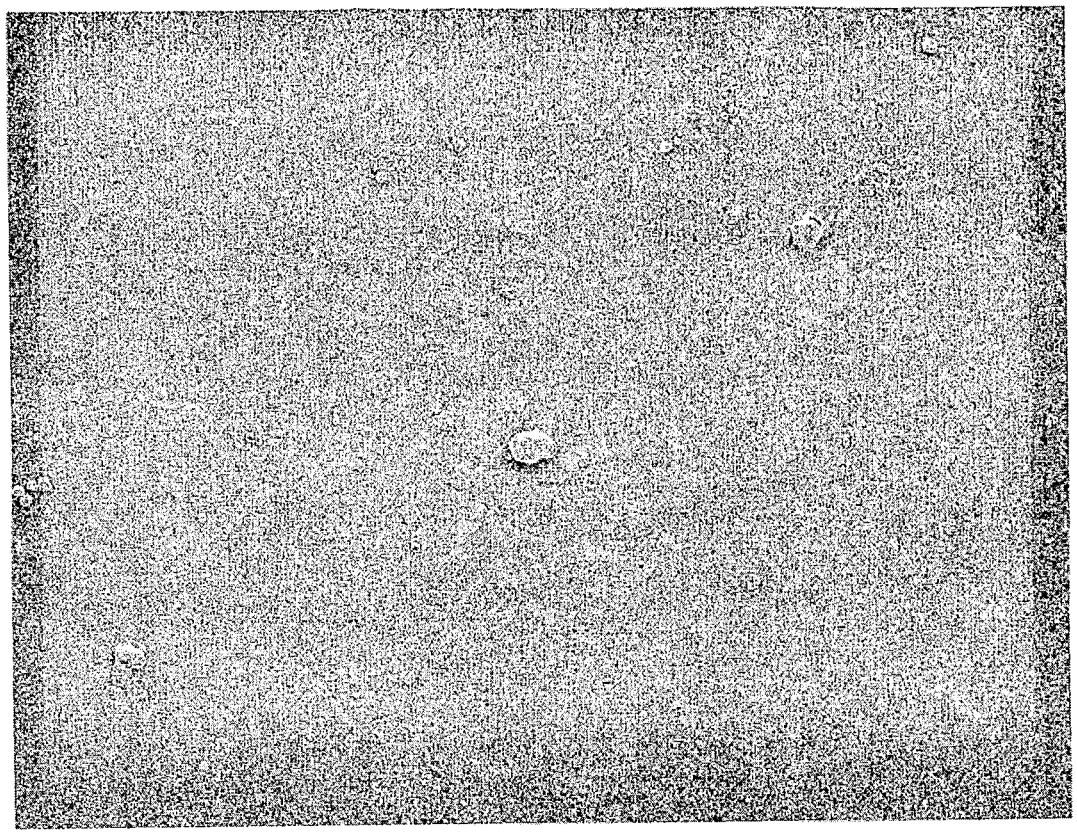
FIG. 30 is an SEM image of abrasively immobilised agglomerates of multi-walled carbon nanotube and 9,10-phenanthraquinone (MWCNT-PAQ agglomerates) on the surface of a bppg electrode.
Figure 31:
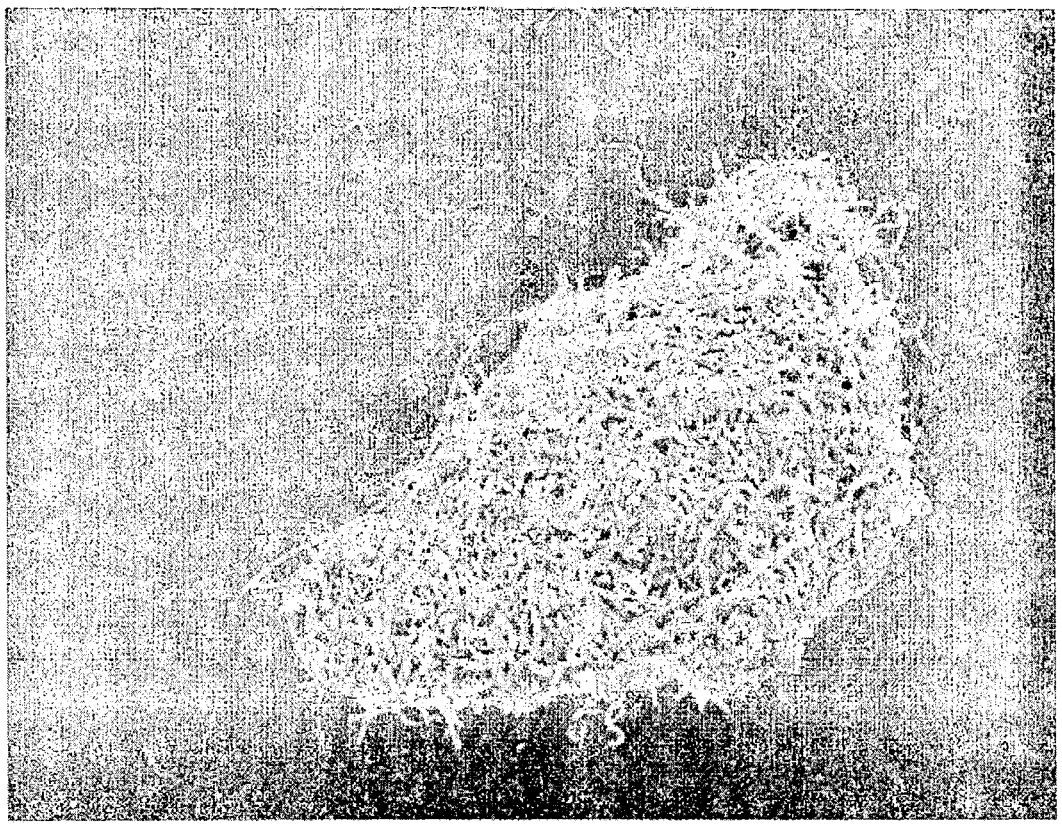
FIG. 31 is a magnified SEM image of an MWCNT-PAQ agglomerate.
Figure 32:
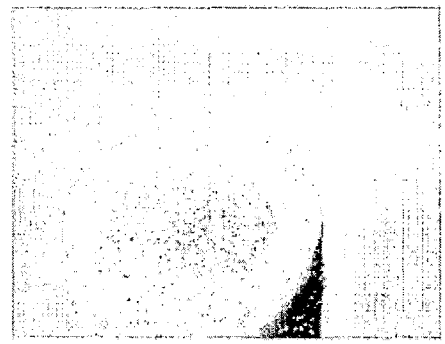
FIG. 32 is a digital image of a bppg electrode after abrasive immobilisation of pure PAQ crystals.
Figure 33:
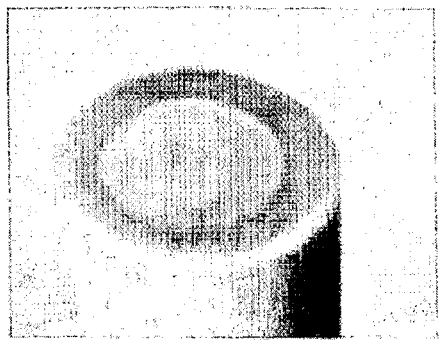
FIG. 33 is a digital image of a bppg electrode after abrasive immobilisation of a physical mixture of PAQ crystals and multi-walled carbon nanotubes (MWCNTs).
Figure 34:
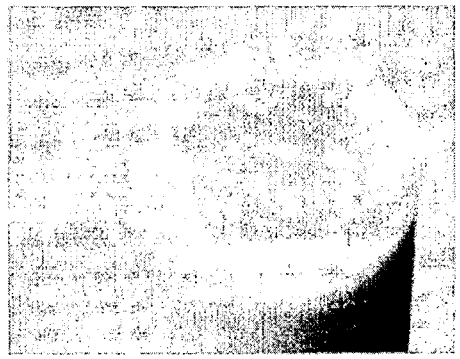
FIG. 34 is a digital image of a bppg electrode after abrasive immobilisation of an MWCNT-PAQ agglomerate.

In order to verify that agglomerates of PAQ or NQ with MWCNTs are formed rather than a physical mixture of microcrystals of either PAQ or NQ and MWCNTs, scanning electron microscopy (SEM) was employed. Each material was imaged separately after abrasive immobilisation onto the surface of a clean bppg electrode had been carried out. First the SEM image of pure MWCNTs (with no organic solid present) was recorded (FIG. 29). Next the SEM images of the MWCNTs, which had been modified according to the procedure given in section 2.2 were recorded for comparison (FIGS. 30 and 31).

Figure 28:
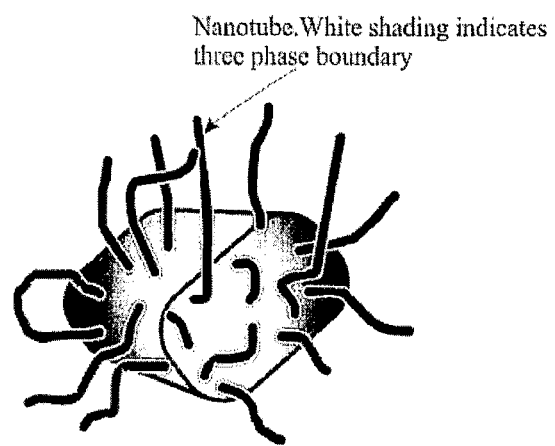
FIG. 28 is a schematic diagram showing the regions where the formation of a three-phase boundary may occur when a redox active material such as an organic crystal is agglomerated with carbon nanotubes and immobilised on the surface of an electrode. For clarity, the electrode surface is not shown.

These images confirm that unlike unmodified MWCNTs on bppg which are dispersed evenly over the surface (FIG. 29), the MWCNT-PAQ material had indeed formed agglomerates of nanotubes cemented together in bundles by the PAQ (FIGS. 30 and 31) as shown schematically in FIG. 28.

Figure 35:
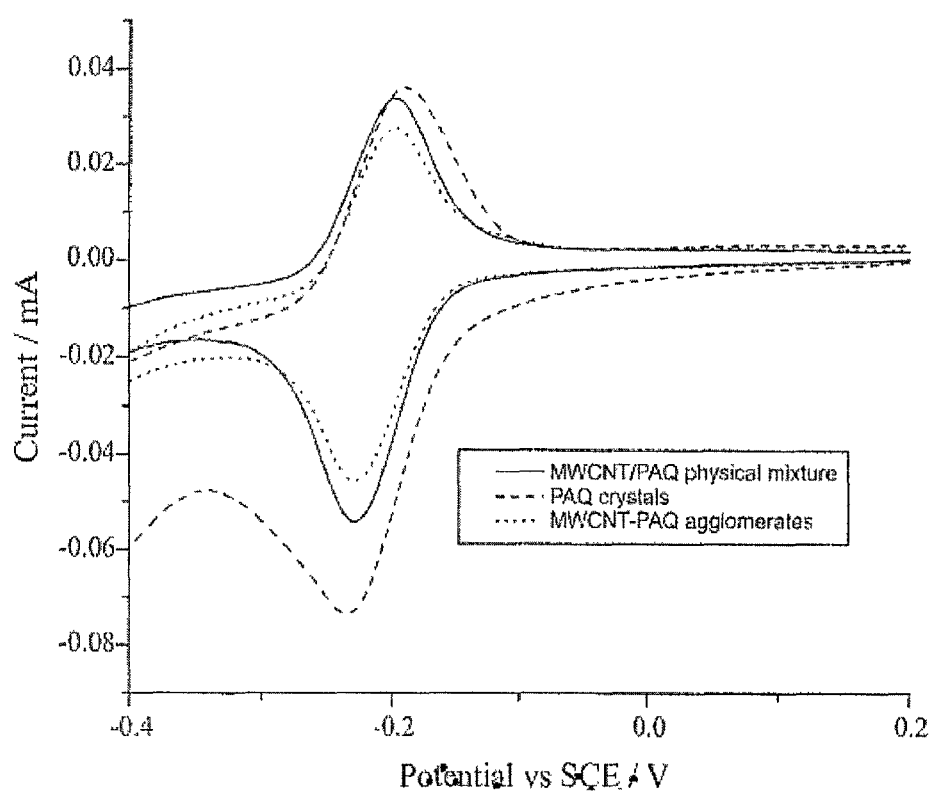
FIG. 35 is the overlaid cyclic voltammograms recorded from each material pictured in FIGS. 8, 9 and 10, allowing a comparison of the magnitude of peak currents compared to the amount of material visibly present on the surface of the bppg electrode.

Finally, the cyclic voltammograms (overlaid in FIG. 35) of PAQ crystals, a mechanical mixture of MWCNTs and PAQ crystals, and the MWCNT-PAQ agglomerates were recorded separately in pH 6.8 buffer after abrasive immobilisation onto the surface of a bppg electrode. In each case a nearly symmetrical wave shape with similar peak heights was observed at ca −0.23 V vs. SCE, with a slight peak to peak separation of ca. 20 mV.

Experimentally it is impossible to control the exact amount of material that is abrasively immobilised onto the surface of the bppg electrode. However, as is apparent from FIGS. 8, 9 and 10, visibly less of the MWCNT-PAQ agglomerate material was needed on the surface of the electrode to give similar magnitudes of peak currents as either the PAQ crystals on their own. FIG. 30 shows that the actual surface coverage of the bppg electrode by the MWCNT agglomerates is sparse. The mechanical mixture of MWCNTs and PAW crystals gives an intermediate result.

A crude calculation of the effective electroactive surface area of the MWCNT-PAQ agglomerate was undertaken. The PAQ molecules were considered to occupy rectangles of area 2.5×10$^{-19}$ m$^2$ and the number of molecules oxidised or reduced was calculated from the peak area of the corresponding cyclic voltammogram. Thus the approximate electroactive surface area of this material was found to be typically greater than three times that of the bppg electrode itself.

It is worth noting that this crude calculation assumes the area of the electrode surface to be equal to its geometric area. In reality, polished surfaces may have a surface area substantially greater than the geometric area. Furthermore a proportion of the PAQ or NQ binder may not react due to inefficient charge transfer to the electrode surface, as impurities on the MWCNT surface may impair conductivity at the bppg/MWCNT interfacial region. However, even with these limitations in mind the results are still indicative of a significant increase in the electroactive surface area of the electrode when MWCNT agglomerates are immobilised upon it.

One possible explanation for this is found by considering that one of the advantages of electrodes modified with carbon nanotubes is a larger effective electroactive surface area with obvious analytical benefits. The structure of abrasively immobilised MWCNT agglomerates has been shown (above) to consist of bundles of MWCNTs cemented together in an amorphous organic solid on the surface of a substrate electrode. As discussed earlier, such a structure confers a significantly greater electroactive surface area where three-phase boundaries can be formed than the situation when pure organic crystals or physical mixtures of an organic solid and graphite powder are used. Hence less of the agglomerate material is required to produce signals of similar orders of magnitude as in the other two cases studied above.

Determination of Surface Immobilisation

Figure 36A:
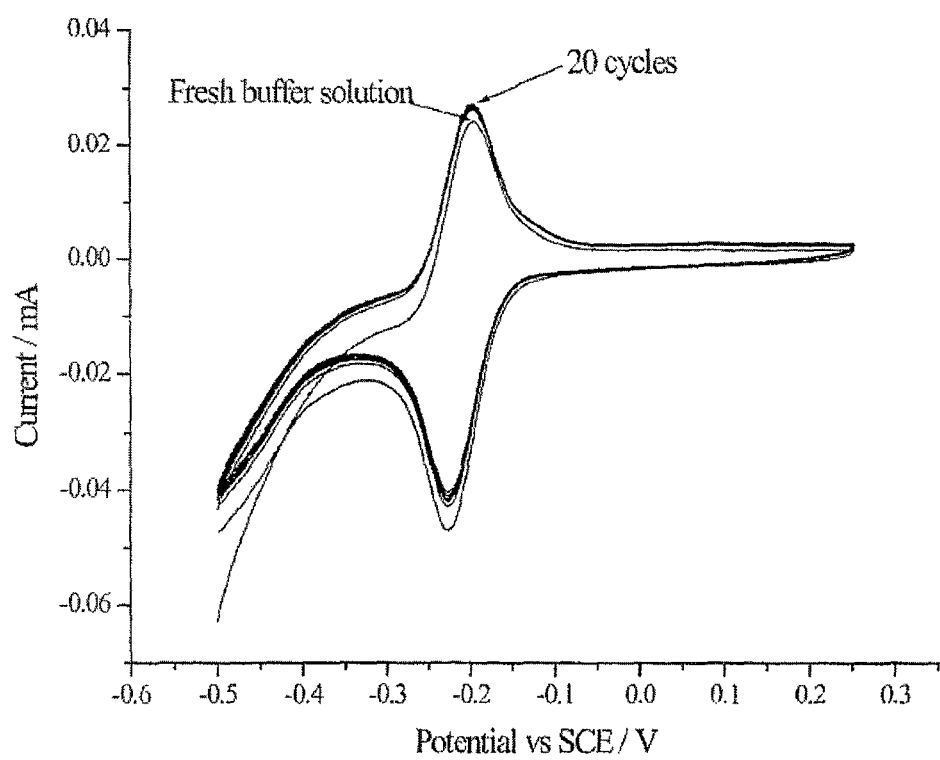
FIG. 36A is a cyclic voltammogram showing 20 repeat cycles (scan rate 50 mV s$^{-1}$) in pH 6.8 buffer of MWCNT-PAQ agglomerates on bppg.
Figure 36B:
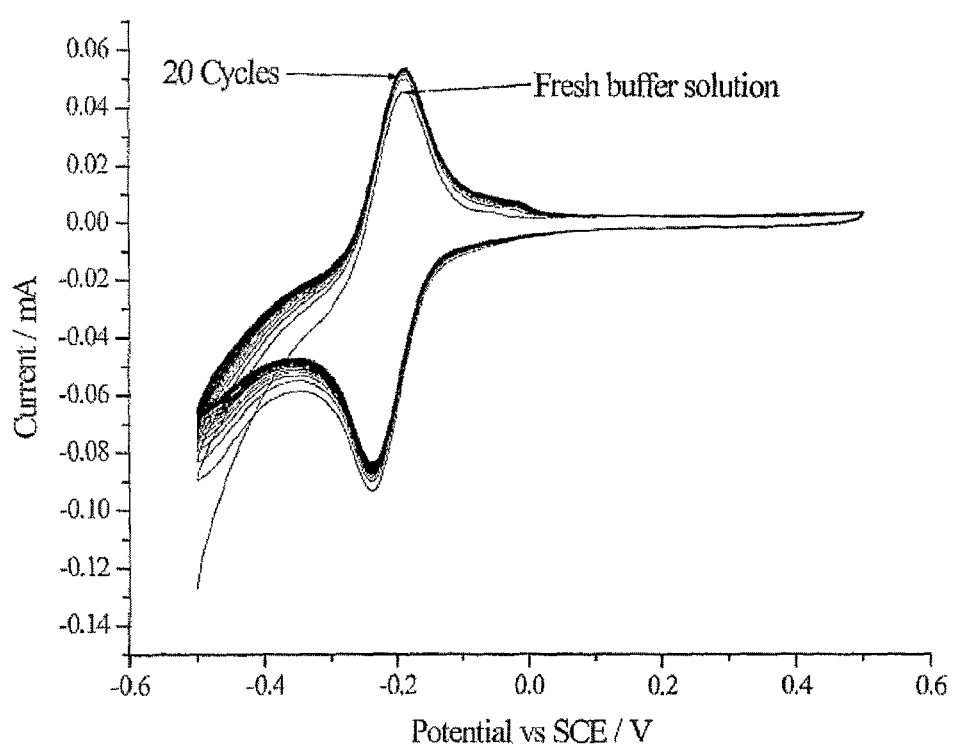
FIG. 36B is a cyclic voltammogram showing 20 repeat cycles (scan rate 50 mVs$^{-1}$) in pH 6.8 buffer of agglomerates of multi-walled carbon nanotubes and 1,2-napthaquinone (MWCNT-NQ agglomerates) on bppg. A cyclic voltammogram recorded after replacing the buffer with fresh solution is overlaid in each case.

The immobilisation onto the bppg surface was confirmed using cyclic voltammetry. The two agglomerates were then studied over the entire pH range pH 1-12. The first step in the protocol, once the potential region of the redox process for PAQ or NQ had been determined, was to conduct twenty repetitive scans (the exact potential range of these scans varied between PAQ and NQ and with pH) to ensure the stability of the species. In the case of both MWCNT-PAQ agglomerates and MWCNT-NQ agglomerates a nearly symmetrical wave shape with a slight peak separation that increased with increasing scan rate (see below) was observed at every pH (FIGS. 36A and 36B). It was found that after twenty repetitive scans the peak currents (which initially were found to decrease slightly) remained stable and that the charges (peak areas) of both the oxidative and reductive peak processes were equal to each other.

Figure 37A:
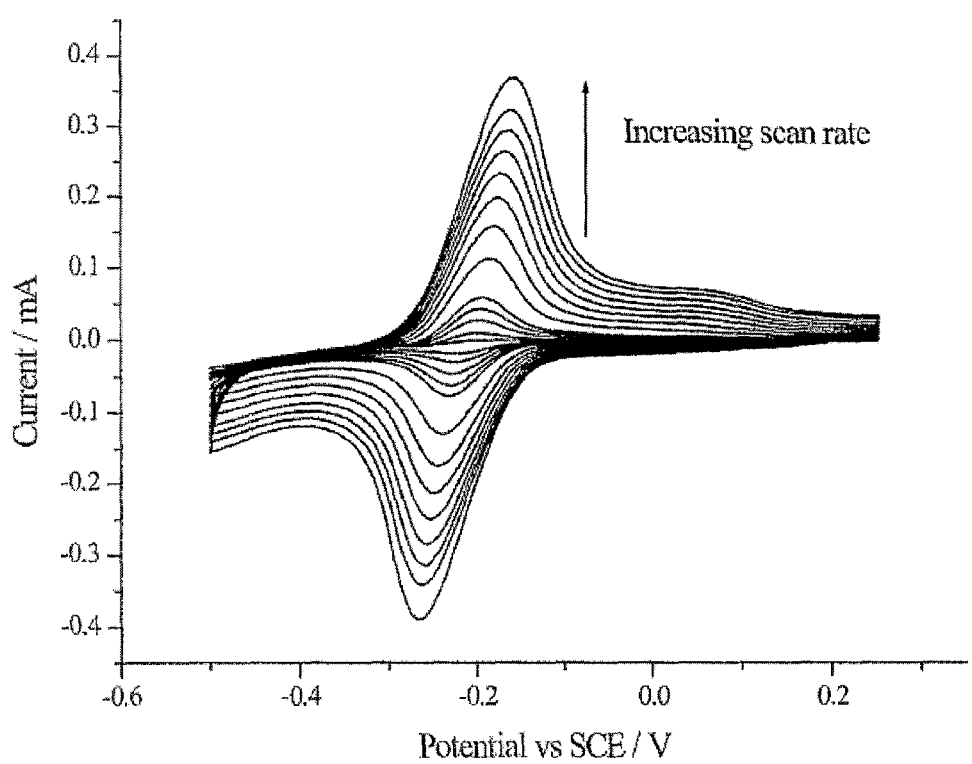
FIG. 37A is a cyclic voltammogram at varying scan rates (25-900 mV s$^{-1}$) recorded in pH 6.8 buffer of MWCNT-PAQ agglomerates on bppg.
Figure 37B:
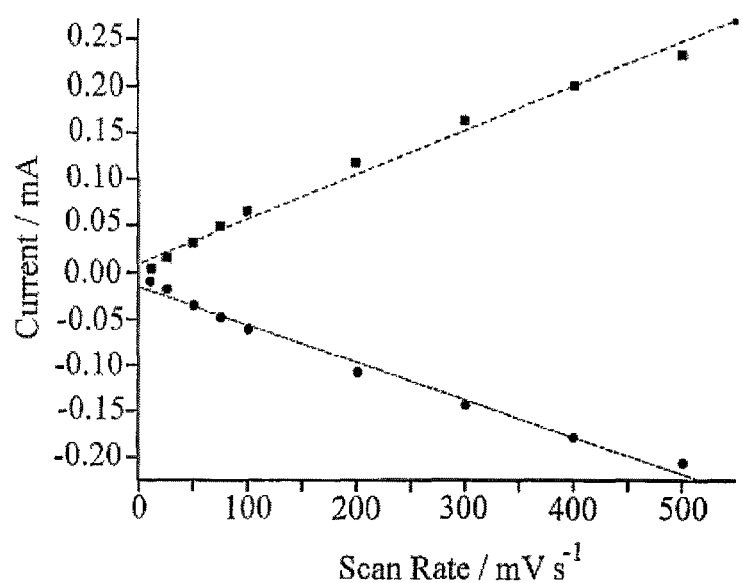
FIG. 37B shows the corresponding plots of peak current against rate scan for MWCNT-PAQ agglomerates on bppg.
Figure 37C:
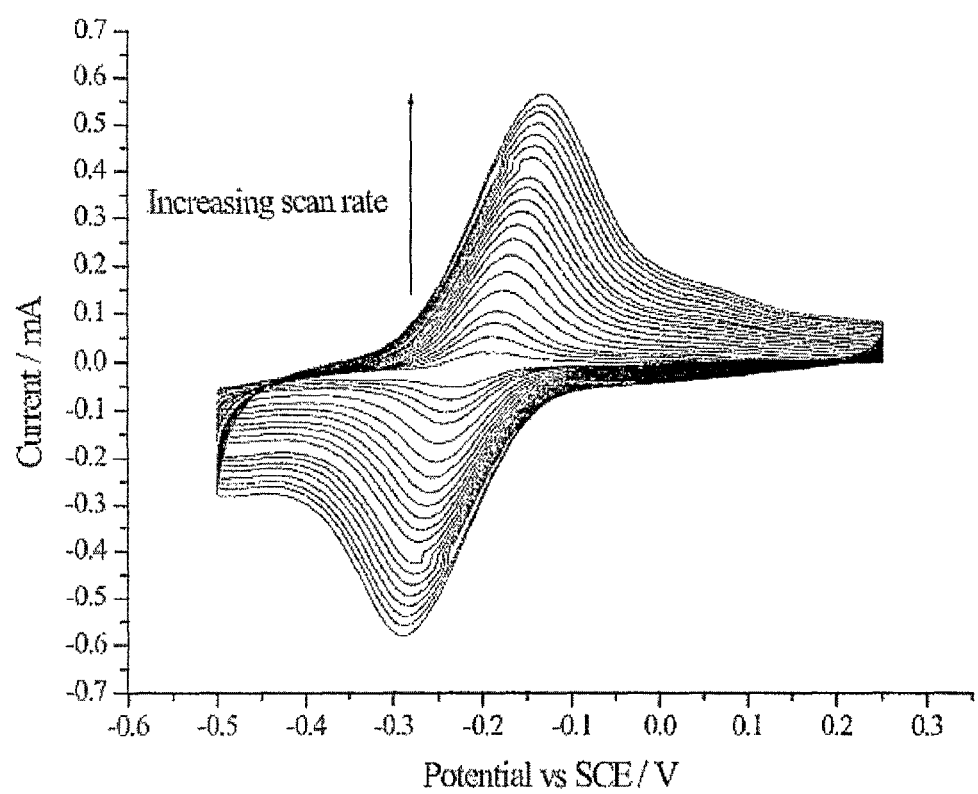
FIG. 37C is a cyclic voltammogram at varying scan rates (25-900 mVs$^{-1}$) recorded in pH 6.8 buffer of MWCNT-NQ agglomerates on bppg.
Figure 37D:
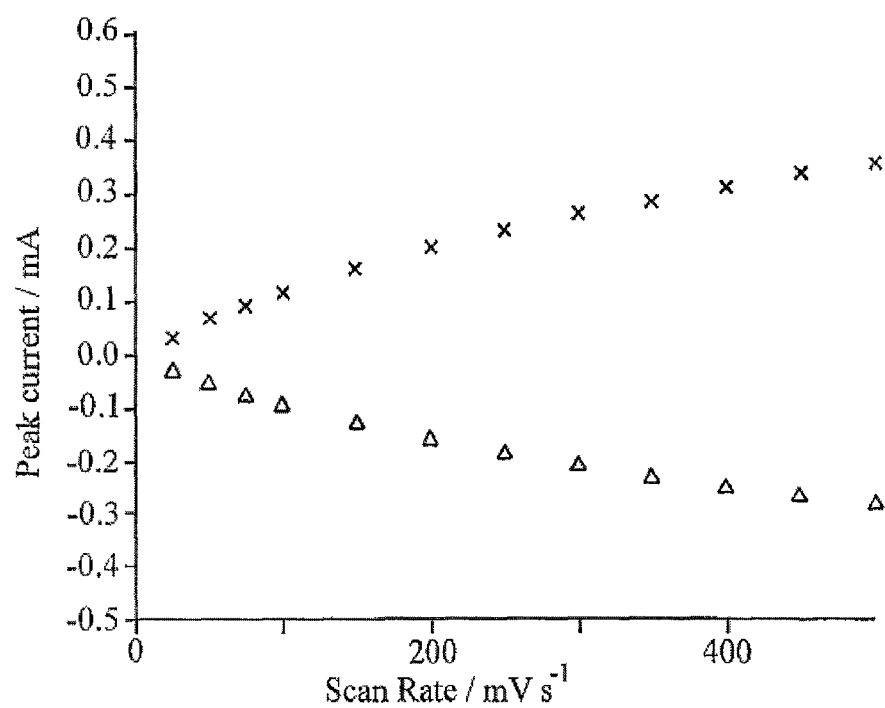
FIG. 37D shows the corresponding plots of peak current against scan rate for MWCNT-NQ agglomerates on bppg.

The next step in the protocol was to replace the electrolyte solution with fresh solution and record the voltammetric response. The corresponding cyclic voltammogram (overlaid in FIGS. 36A and 36B) was found to overlay the last scan thereby confirming that the electroactive species remains on the surface of the electrode and is not released to solution. Finally the scan rate was varied from 25 to 900 mV s$^{-1}$ (FIGS. 37A and 37C) and a plot of peak current vs. scan rate was found to be almost linear (FIGS. 37B and 37D). The peak separation (ca. 20 mV at low scan rate) is close to the ideal zero peak to peak separation for an immobilised, electrochemically reversible species. However, the discrepancy between the experimental and theoretical peak separation, and the deviation from linearity in the plots of peak current vs. scan rate may be tentatively attributed to some slight ohmic distortion and/or electrode kinetic factors. In fact the wave shapes and the variation of peak potential with increasing scan rate suggest that an electrochemically quasi-reversible system exists over the entire pH range studied.

Example 1

Voltammetric Response of Agglomerates to pH at Room Temperature

Figure 38A:
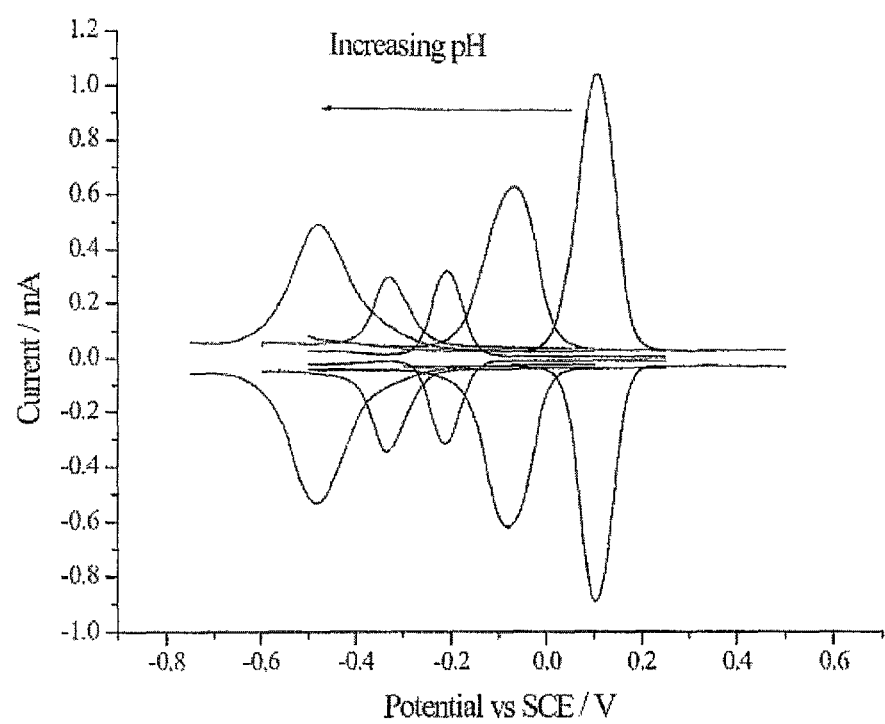
FIG. 38 is overlaid oxidative and reductive square wave voltammograms recorded in a range of buffers (pH 1.0, pH 4.6, pH 6.8, pH 9.2, pH 12.0) at 20° C. wherein FIG. 38A uses MWCNT-PAQ agglomerates on bppg, and FIG. 38B uses MWCNT-NQ agglomerates on bppg.
Figure 38B:
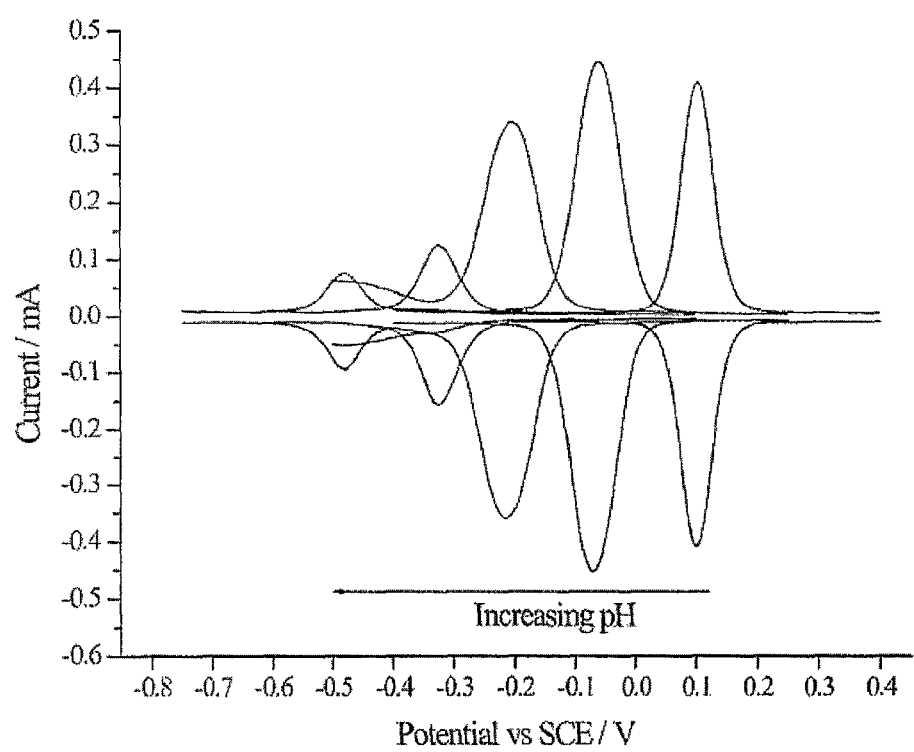
Figure 39A:
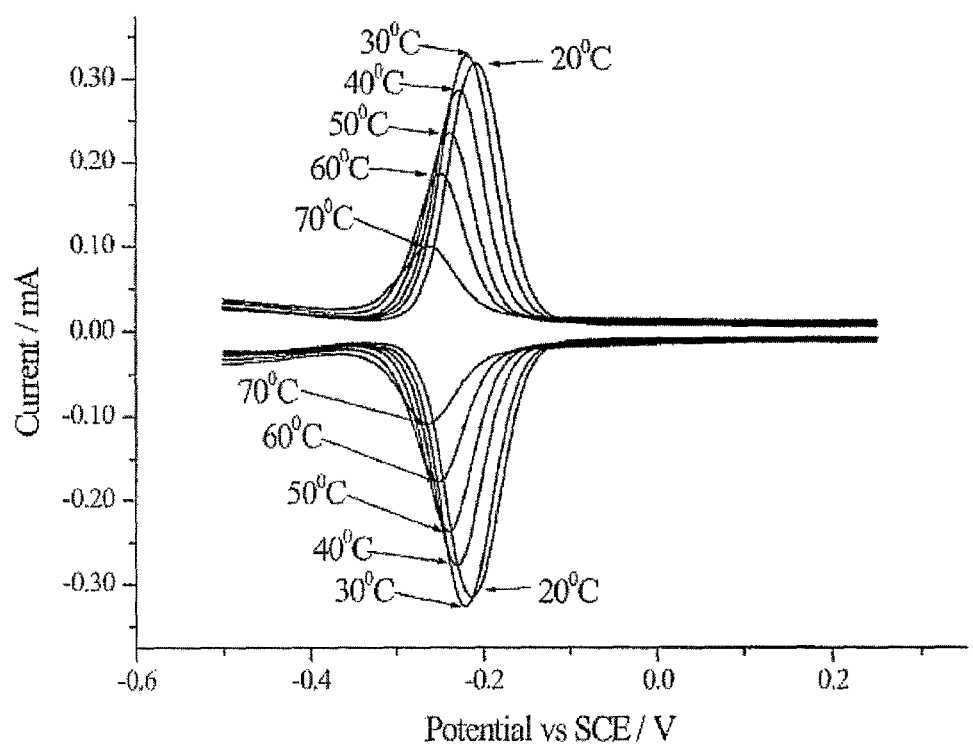
FIG. 39A is an overlaid square wave voltammogram of MWCNT-PAQ agglomerates on bppg.
Figure 39B:
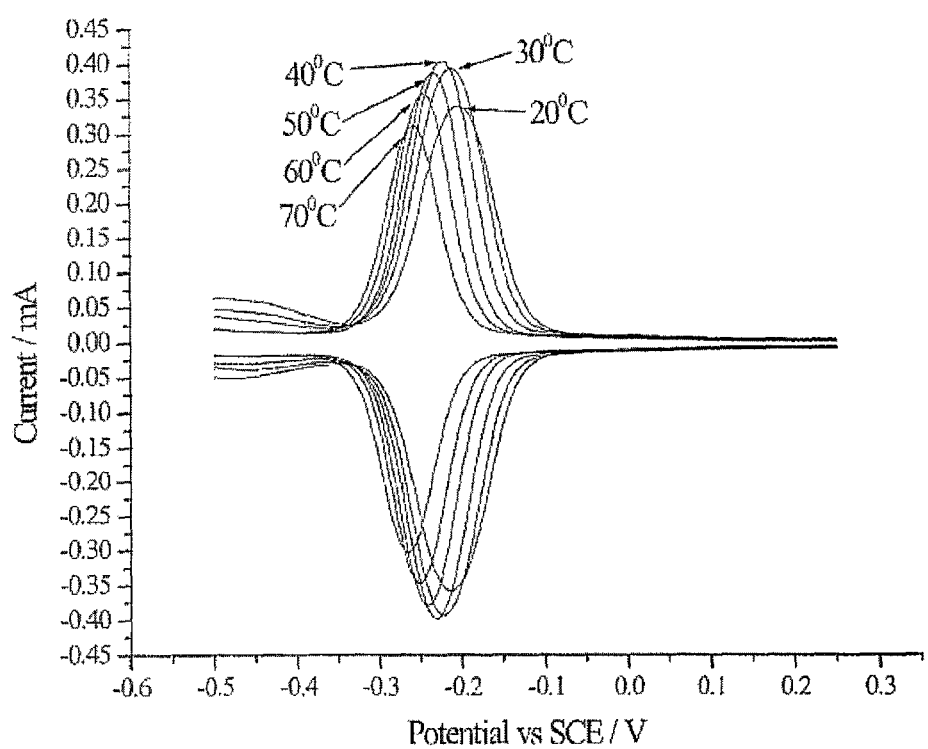
FIG. 39B is an overlaid square wave voltammogram of MWCNT-NQ agglomerates on bppg, both in pH 6.8 buffer at varying temperatures (20, 30, 40, 50, 60 and 70° C.).

Having established, using cyclic voltammetry in Example 2 above, that a stable, electrochemically almost reversible system is observed for both MWCNT-PAQ and MWCNT-NQ agglomerates over the entire pH range from pH 1 to pH 12, square wave voltammetry was utilised as the electrochemical method of probing the system in all the studies detailed below. This has significant advantages as compared to conventional cyclic voltammetry, since it provides a means of carrying out a single sweep which produces a well-defined voltammetric peak due to PAQ and NQ having almost reversible electrode kinetic behaviour. This can therefore aid in the resolution of the MWCNT-PAQ and MWCNT-NQ reduction waves, especially at higher pH where oxygen reduction may compete at a similar potential to that of the redox process of interest. Square wave voltammograms were recorded for MWCNT-PAQ and MWCNT-NQ agglomerates in a range of pH solutions (pH 1, 0.1M HCl; pH 4.6, 0.1M acetic acid+0.1M sodium acetate; pH 6.8, 0.025 M Na$_2$HPO$_4$+0.025 M KH$_2$PO$_4$; pH 9.2, 0.05 M disodium tetraborate; pH 12 0.01M sodium hydroxide) and are overlaid in FIGS. 38A and 38B respectively. It is apparent from FIGS. 38A and 38B that as the pH is increased the peak potential of MWCNT-PAQ and MWCNT-NQ shifts to more negative potentials as expected. This behaviour is consistent with that observed for PAQ crystals abrasively immobilised on a bppg electrode.

The corresponding plot of peak potential against pH reveals a linear response from pH 1 to pH 12 with a gradient of 55.2 and 53.2 mV/pH unit for MWCNT-PAQ and MWCNT-NQ respectively, which is reproducible upon repetitive electrode preparations as described earlier. This is close to a Nernstian response as given by the equation discussed earlier and is again consistent with previous studies on carbon powder.

Example 12

Voltammetric Response of Agglomerates to pH at Elevated Temperature

The effect of temperature on the voltammetric response of the agglomerates was investigated in order to determine whether the materials might be used as suitable pH probes for high-temperature environments.

One factor to be noted while studying the effect of temperature on the system is how the pH of the solution varies with temperature as the dissociation constants of the components in the buffer solution vary with temperature. To this end three IUPAC buffers (pH 4.6, pH 6.8 and pH 9.2) were utilised that have a known set of pHs at a given temperature. The error due to using pH 1 and pH 12 solutions of dilute HCl or NaOH respectively for high-temperature studies is negligible as the pH variation with temperature of all buffers is small and these are the extremities of the plot.

Square wave voltammograms were recorded for each pH studied in the range pH 1 to pH 12 over the temperature range 20-70° C. for both MWCNT-PAQ and MWCNT-NQ. Note that the upper limit of this temperature range was limited by the onset of bubble formation on the electrode as the temperature approached the boiling point of the solution. FIGS. 15A and 15B show the overlaid square wave voltammograms of MWCNT-PAQ and MWCNT-NQ respectively over the temperature range 20-70° C. in pH 6.8 IUPAC buffer. Similar responses were obtained at every other pH studied. There is a shift of the peak potential to more negative values with increasing temperature which can be attributed in part to a combination of changes in the SCE reference couple, the temperature dependence of the formal potential ($E_f^o$) and the temperature term in the Nernstian equation discussed earlier. It is worth noting that the peak current initially increases with temperature, but then decreases steadily after 30° C. In order to investigate the stability of the agglomerates at elevated temperatures cyclic voltammetry was employed at every temperature studied in the range 20-70° C. Five hundred scans were performed at each temperature on the abrasively immobilised MWCNT agglomerates at a scan rate of 200 mV s$^{-1}$ and every fifth scan recorded, corresponding to a time interval of ca. 35 seconds. In every case a single, reversible and almost symmetrical wave was observed corresponding to the MWCNT-PAQ or MWCNT-NQ agglomerate as described earlier. From these voltammograms the peak area was measured, which is proportional to the amount of the electroactive species remaining on the surface of the electrode in the form of MWCNT agglomerates. From a plot of peak area against time (not shown) it was apparent that although the signal remains stable for 500 scans over ca. 1 hour at 20° C., at temperatures above 30° C. there is a decrease in the magnitude of the signal. This behaviour is in contrast to chemically adsorbed anthraquinone on graphite particles, where the magnitude of the signal increases steadily with increasing temperature, but is in agreement with earlier studies of PAQ physically adsorbed onto the surface of graphite particles. This would suggest that the decrease in signal observed at elevated temperatures for MWCNT-PAQ and MWCNT-NQ agglomerates is due to partial dissolution of the agglomerates. However, even at 70° C. after 500 scans (ca. 1 hour) an appreciable signal, ca. 10% of the original value, still remains.

Figure 40:
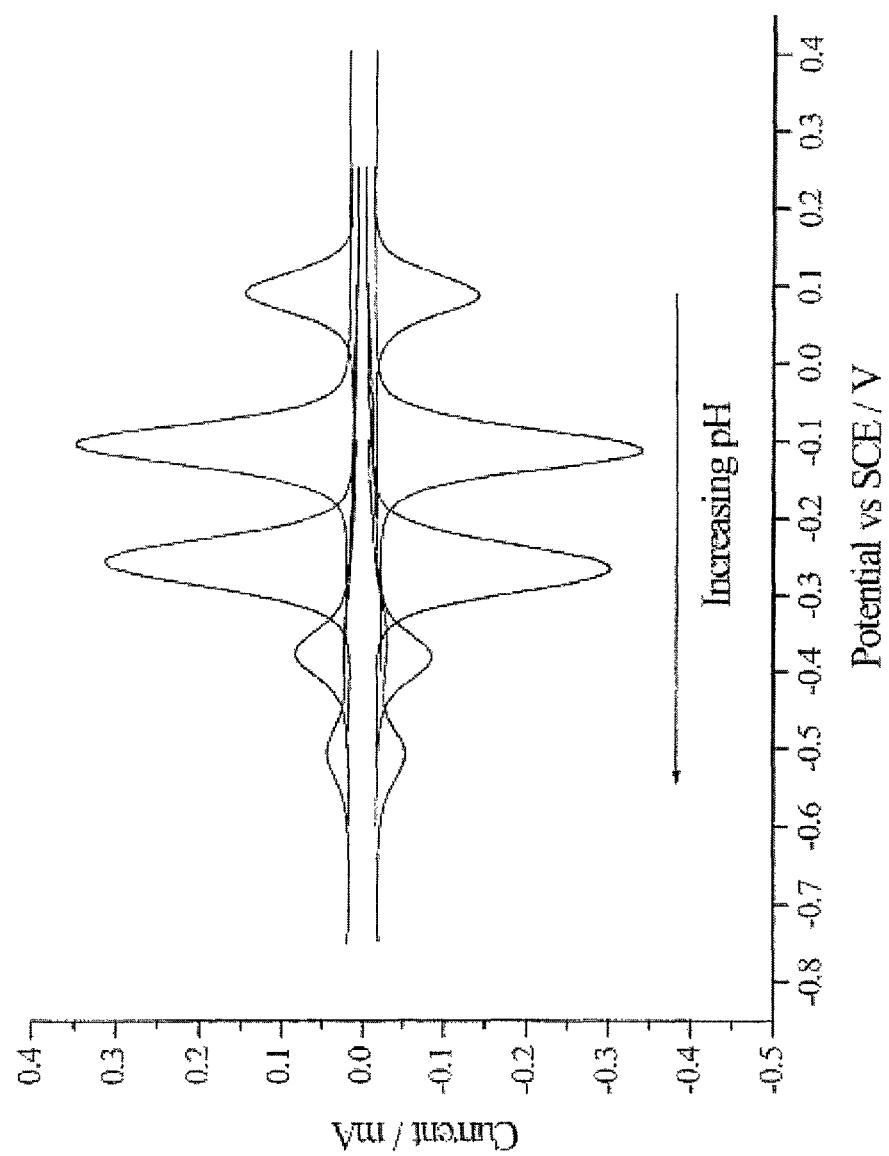
FIG. 40 is overlaid oxidative and reductive square wave voltammograms of MWCNT-NQ agglomerates in a range of buffers (pH 1.0, pH 4.6, pH 6.8, pH 9.2 and pH 12.0) at 70° C.

FIG. 40 shows the overlaid square wave voltammogram for NQ at 70° C. showing that an analytically useful response may be obtained at this elevated temperature.

A plot of peak potential vs. pH at each temperature studied yielded a straight line, with $R^2$ values not less than 0.998, for both MWCNT-PAQ and MWCNT-NQ agglomerates, the gradients of which are given in Table 6. The theoretical gradient as predicted by the Nernst equation is also given in Table 6 for comparison. As can be seen the variation of the gradient of peak potential with pH is not Nernstian and indeed is relatively insensitive of temperature varying by ca 3 mV/pH unit over a temperature range of 50° C. This is advantageous in that it not only demonstrates that these agglomerates may be used as pH sensors at elevated temperatures, but also that they are not greatly affected by quite significant changes in temperature.

TABLE 6

Experimental gradients of plots of peak potential against pH at each temperature studied for abrasively immobilised MWCNT-PAQ and MWCNT-NQ agglomerates.

| Temperature | Theoretical gradient | Experimental Gradient (mV/pH unit) | |
| --- | --- | --- | --- |
| (K) | (mV/pH unit) | MWCNT-PAQ | MWCNT-NQ |
| 293 | 58.1 | 55.2 | 53.2 |
| 303 | 60.1 | 55.4 | 53.4 |
| 313 | 62.1 | 56.5 | 53.7 |
| 323 | 64.1 | 56.7 | 53.9 |
| 333 | 66.1 | 56.9 | 54.9 |
| 343 | 68.1 | 57.0 | 56.6 |

As shown in Examples 11 and 12, a linear response of peak potential to pH is observed for both MWCNT-PAQ and MWCNT-NQ agglomerates over the entire pH range and temperature range studied. Furthermore, a comparison of the gradients of a plot of peak potential against pH at each temperature reveals that both MWCNT-PAQ and MWCNT-NQ agglomerates are relatively insensitive to the effects of temperature changes. Such a property is advantageous for pH measurement where samples are obtained at a range of different temperatures.

DETAILED DESCRIPTION OF THE FOURTH PREFERRED ASPECT OF THE INVENTION

According to a fourth preferred aspect of the invention, the electrode comprises a layer on a substrate of a composition of the carbon and the redox-active compound, the layer having an edge formed by cutting through the layer to expose carbon and redox-active compound.

Figure 41:
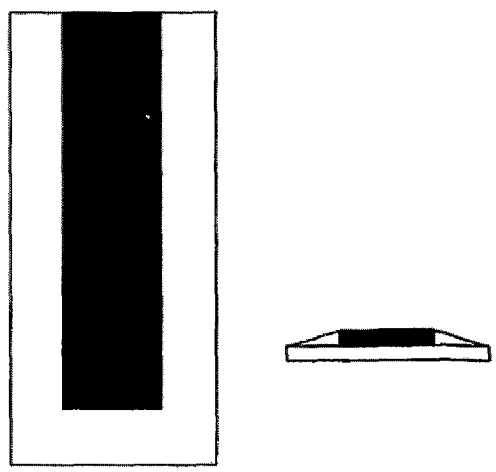
FIG. 41 is a schematic of a print, laminate and cut (PLC) electrode in accordance with the fourth preferred aspect of the present invention.
Figure 42:
FIG. 42 shows a micrographic of the PLC electrode.

An electrode of the fourth preferred aspect of the invention can be made by first printing onto a substrate using a carbon based inked mixed with crystals if whichever chemical is to be used for the analysis. The printed electrode is then laminated and shaped into a strip, as shown in FIG. 41. The electrode is activated by cutting the end off the strip, with a scissors, to reveal a cross section of the print. This cross section will then have a carbon (ink) and crystals of the chemical that was mixed with the ink, exposed at its surface, as shown in FIG. 42.

When the cut electrode is then dipped into solution, reactions can be induced to happen at the triple phase boundary between the carbon, the solid crystals and the analyte solution.

Figure 43:
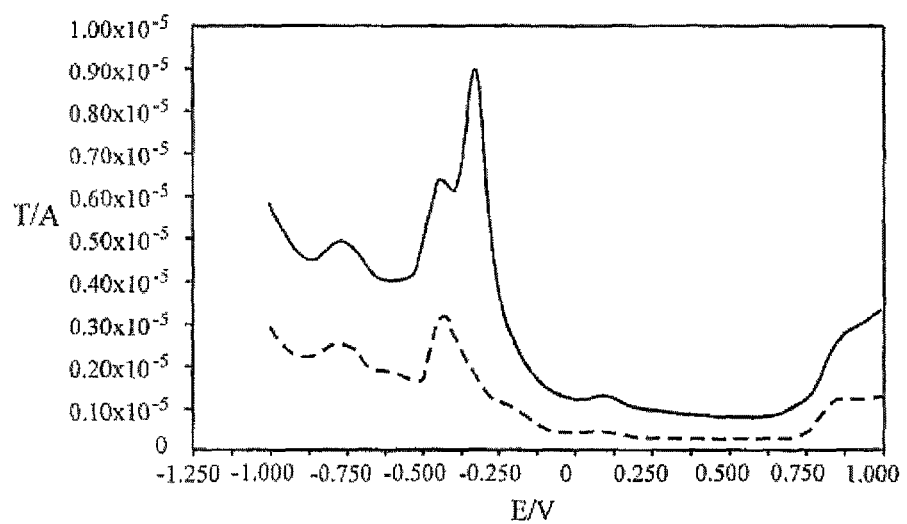
FIG. 43 shows the first scan of an uncut electrode (lower plot) and the first scan of the same electrode after it has been "cut" (upper plot).
Figure 44:
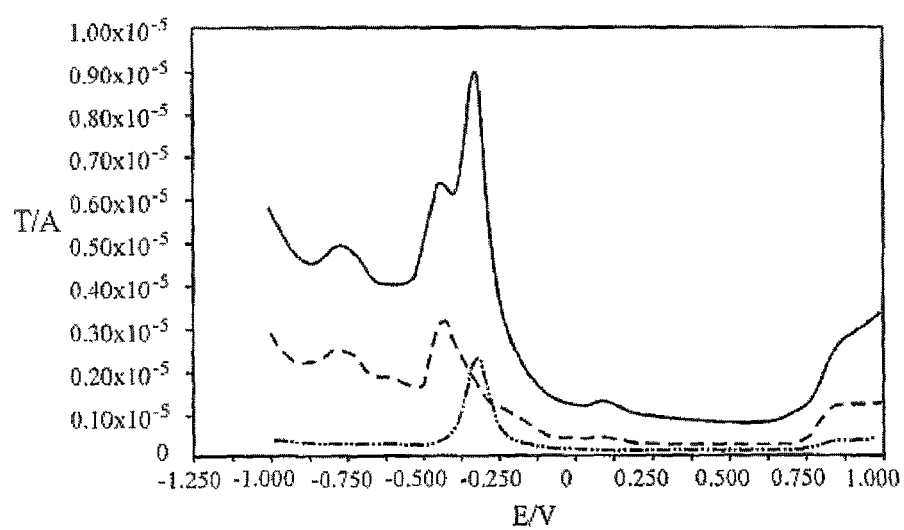
FIG. 44 shows the same data as FIG. 43, with the square wave voltammagram (SWV) generated from a laminated cut electrode (lowest plot).

The increased sensitivity associated with the "cut" electrode can be seen in FIGS. 43 and 44. FIG. 43 shows a Square Wave Voltammagram (SWV) recorded using a printed electrode (lower line). The figure also shows that the SWV recorded with the same electrode after the end had been cut off (upper line). The sharp peak visible on the SWV for the cut electrode (upper line) is due to the exposed crystals in contact with the solution.

When the printed electrodes have been laminated there is no surface of the electrode exposed. However when the end is cut off the electrode strip, the exposed surface (see FIG. 41) produces a SWV like the one presented in FIG. 44, the lowest line. Also shown in FIG. 44 are the curves from FIG. 43 for comparison. The plot also demonstrates the cleaner signal achieved with the laminated and cut electrode.

It will be apparent to those skilled in the art that modifications may be made to the invention as described above without departing from the scope of the claims below.

The invention claimed is:

1. A method for preparing an electrode for use in an electrochemical sensor, said method comprising modifying carbon with a chemically sensitive redox active material wherein the material is a single redox active species or two redox active species, with the proviso that the material that is two redox active species does not include anthraquinone, phenanthrenequinone or N,N=-diphenyl-p-phenylenediamine (DPPD), and wherein the electrode is operable over an entire pH range of 1 to 12.

2. A method according to claim 1, wherein the step of modifying the carbon comprises one or more of the following methods:
  1) derivatisation via physical adsorption of the chemically sensitive redox active material; and
  2) physical mixing with the chemically sensitive redox active material and a binder.

3. The method according to claim 1, further comprising the step of applying the carbon modified with the chemically sensitive redox active material to a substrate.

4. The method according to claim 3, wherein the step of applying comprises abrasively immobilising the composition on the surface of the substrate.

5. A method for preparing an electrode for use in an electrochemical sensor as claimed in claim 2, said method comprising modifying carbon with a single chemically sensitive redox active material selected from an anthraquinone, phenanthrenequinone or N,N-diphenyl-p-phenylenediamine (DPPD).

6. An electrode for use in an electrochemical sensor, said electrode comprising carbon and a redox-active compound wherein the redox-active compound is a single redox active compound or two redox active compounds with the proviso that if two redox active compounds are present, then the compounds are not selected from anthraquinone, phenanthrenequinone or N,N'-diphenyl-p-phenylenediamine (DPPD), and wherein the electrode is operable over an entire pH range of 1 to 12.

7. The electrode according to claim 6, wherein the redox active compound is not anthraquinone, phenanthrenequinone or N,N'-diphenyl-p-phenylenediamine.

8. The electrode according to claim 6, wherein the redox active compound is a chemically sensitive compound.

9. The electrode according to claim 6, comprising carbon modified with a redox'active material, wherein the redox active material is a chemically sensitive material which undergoes an irreversible chemical reaction when the electrode is subjected to cyclic voltammetry.

10. The electrode according to claim 9, wherein the product of the irreversible chemical reaction displays reversible electrochemistry when the electrode is subjected to cyclic voltammetry.

11. The electrode according to claim 6, wherein the chemically sensitive redox active compound is sensitive to the concentration of protons.

12. The electrode according to claim 9, wherein the chemically sensitive redox active material undergoes polymerization when subjected to cyclic voltammetry.

13. The electrode according to claim 12, wherein the chemically sensitive redox active material has a nitro group substituent.

14. The electrode according to claim 6, wherein the electrode comprises a single redox active compound selected from the group consisting of anthraquinone, phenanthrenequinone or N,N'-diphenyl-p-phenylenediamine.

15. The electrode according to claim 6, wherein the chemically sensitive redox active material is physically adsorbed to the carbon.

16. An electrochemical sensor comprising an electrode as claimed in claim 6.

17. An electrode for use in a electrochemical sensor, said electrode comprising carbon and a single redox-active compound selected from anthraquinone, phenanthrenequinone or N,N'-diphenyl-p-phenylenediamine (DPPD);
   wherein the chemically sensitive redox active material is physically adsorbed to the carbon; and
   wherein the electrode is operable over an entire pH range of 1 to 12.

18. A method for preparing an electrode for use in an electrochemical sensor, said method comprising modifying carbon with a single chemically sensitive redox active material selected from the group consisting of anthraquinone, phenanthrenequinone or N,N-diphenyl-p-phenylenediamine (DPPD); and wherein the step of modifying the carbon comprises one or more of the following methods:
   1) derivatisation via physical adsorption of the chemically sensitive redox active material; and
   2) physical mixing with the chemically sensitive redox active material and a binder; and
   wherein the electrode is operable over an entire pH range of 1 to 12.

19. A method according to claim 17, wherein the step of modifying the carbon comprises derivatisation via physical adsorption of the chemically sensitive redox active material.

20. An electrochemical sensor comprising an electrode as claimed in claim 17.

* * * * *